US012751942B2

(12) United States Patent
Steiner et al.

(10) Patent No.: US 12,751,942 B2
(45) Date of Patent: Oct. 6, 2026

(54) METHODS OF TREATING INFLUENZA AND POXVIRUS VIRAL INFECTIONS

(71) Applicant: VERU INC., Miami, FL (US)

(72) Inventors: Mitchell S. Steiner, Germantown, TN (US); Kester Gary Barnette, Denver, NC (US)

(73) Assignee: VERU INC., Miami, FL (US)

( * ) Notice: Subject to any disclaimer, the term of this patent is extended or adjusted under 35 U.S.C. 154(b) by 0 days.

(21) Appl. No.: 18/132,285

(22) Filed: Apr. 7, 2023

(65) Prior Publication Data

US 2023/0321045 A1 Oct. 12, 2023

Related U.S. Application Data

(60) Provisional application No. 63/456,943, filed on Apr. 4, 2023, provisional application No. 63/394,260, filed on Aug. 1, 2022, provisional application No. 63/328,504, filed on Apr. 7, 2022.

(51) Int. Cl.

| | |
|---|---|
| ***A61K 31/4174*** | (2006.01) |
| ***A61K 31/4164*** | (2006.01) |
| ***A61P 31/20*** | (2006.01) |

(52) U.S. Cl.

CPC ...... *A61K 31/4174* (2013.01); *A61K 31/4164* (2013.01); *A61P 31/20* (2018.01)

(58) Field of Classification Search

CPC .. A61K 31/4164; A61K 31/4174; A61P 31/20
See application file for complete search history.

(56) References Cited

U.S. PATENT DOCUMENTS

| | | | | |
|---|---|---|---|---|
| 8,940,291 B2 | 1/2015 | Bell et al. | | |
| 10,369,205 B2 | 8/2019 | Agrawal et al. | | |
| 11,648,236 B2 * | 5/2023 | Steiner | ................. | A61K 31/706 514/397 |
| 2002/0094991 A1 | 7/2002 | Gallaher | | |
| 2009/0012107 A1 | 1/2009 | Aman et al. | | |
| 2019/0092755 A1 | 3/2019 | Miller et al. | | |
| 2023/0348433 A1 * | 11/2023 | Bird | ..................... | C07D 403/04 |

FOREIGN PATENT DOCUMENTS

| | | |
|---|---|---|
| WO | WO 00/09114 A1 | 2/2000 |
| WO | WO 2010/030582 A2 | 3/2010 |
| WO | WO-2012/064654 A1 | 5/2012 |
| WO | WO 2021/203100 A9 | 10/2021 |

OTHER PUBLICATIONS

Magano "Recent synthetic approaches to oseltamivir phosphate (Tamiflu) for the treatment of influenza", Tetrahedron, 67, 7875-7899 (Year: 2011).*

Kumari et. al. "Antiviral Approaches against Influenza Virus", Clinical Microbiology Reviews (Year: 2023).*

Cohen et. al. "The Microtubule Inhibitor Podofilox Inhibits an Early Entry Step of Human Cytomegalovirus", Viruses, 8, 295 (Year: 2016).*

Deng et. al. "An Orally Available Tubulin Inhibitor, VERU-111, Suppresses Triple-Negative Breast Cancer Tumor Growth and Metastasis and Bypasses Taxane Resistance", Mol Cancer Ther, 19(2), 348-363 (Year: 2020).*

Montealegre-Gomez et. al. ("Colchicine: A potential therapeutic tool against COVID-10. Experience of 5 patients", Reumatol. Clin., 17, 371-375 (Year: 2021).*

Oliva M. et al., "Effect of Clinically Used Microtubule Targeting Drugs on Viral Infection and Transport Function", Int. J. Mol. Sci., 2022, vol. 23, pp. 1-22, abstract; p. 3, para. 2-3, p. 4, para 1, Figure 2B.

International Search Report dated Jul. 7, 2023 in respect of International Application No. PCT/US23/17943.

Al-Horani, Rami A et al.: "Potential Anti-SARS-COV-2 Therapeutics That Target the Post-Entry Stages of the Viral Life Cycle: A Comprehensive Review", Viruses 2020, 12, 1092; DOI: 10.3390/v12101092. Point 4.6; p. 17.

Erez, Noam et al.: "Induction of cell-cell fusion by ectromelia virus is not inhibited by its fusion inhibitory complex", Virology Journal 2009, 6:151; Doi: 10.1186/1743-422X-6-151. Abstract; p. 6; figure 4; p. 4, left-hand col. paragraph 1, right-hand col. paragraph 3; p. 8, right-hand col. paragraph 1.

European Search Report dated Nov. 21, 2025, in respect of European Application No. 23785468.2.

* cited by examiner

*Primary Examiner* — Jeffrey H Murray
*Assistant Examiner* — Daniel John Burkett
(74) *Attorney, Agent, or Firm* — Mark S. Cohen; PEARL COHEN LLP

(57) ABSTRACT

The present invention relates to methods of treating specific viral infections, such as an Orthomyxoviridae infection, in a subject in need thereof by administering to the subject a formulation having a therapeutically effective amount of a compound of Formula (I):

(I)

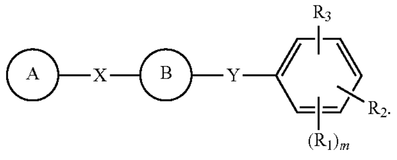

18 Claims, 11 Drawing Sheets

METHODS OF TREATING INFLUENZA AND POXVIRUS VIRAL INFECTIONS

CROSS REFERENCE TO RELATED APPLICATIONS

This application claims the benefit of priority of US Provisional Application Nos. 63/328,504, filed Apr. 7, 2022; 63/394,260, filed Aug. 1, 2022; and 63/456,943, filed Apr. 4, 2023, hereby incorporated by reference.

FIELD OF THE INVENTION

The present invention is directed to methods of treating specific viral infections, using compounds having cytoskeleton disruptor activity, and formulations including the compounds with pharmaceutical acceptable excipients and/or additional cytoskeleton disruptor compounds.

BACKGROUND OF THE INVENTION

Over the last century or two, numerous viral epidemics have posed serious global public health risks including epidemics and pandemics in which millions of otherwise healthy individuals became infected by viral pathogens and died. Unfortunately, until relatively recently, the development of antiviral agents was difficult and treatment for many viral illnesses was mostly directed to ameliorating symptoms and keeping patients isolated until symptoms resolved. Most prominently in recent times was the ongoing global pandemic of severe acute respiratory syndrome coronavirus-2 (SARS-CoV-2) which emerged in 2019. Additionally, there are many other families of viruses that are characterized by endemic status or occasional/seasonal epidemics and pandemics. The instant invention is directed to broad spectrum indirect antiviral agents capable of treating not just SARS-CoV-2 (WO2021/0203100), but also the treatment of multiple viral pathogens of the Orthomyxoviridae (flu viruses such as influenza) and Poxviridae (Poxviruses such as Monkey Pox or smallpox) virus families. The virology of these two families of viruses is described below.

Orthomyxoviridae is a family of negative-sense RNA viruses. It includes seven genera: Alphainfluenzavirus (influenza A), Betainfluenzavirus (influenza B), Deltainfluenzavirus (influenza D), Gammainfluenzavirus (influenza C), Isavirus, Thogotovirus, and Quaranjavirus. The first four genera contain viruses that cause influenza in birds and mammals, including humans. Common symptoms of the influenza virus infections include fever, headaches, and fatigue which are the result of the huge amounts of proinflammatory cytokines and chemokines (such as interferon or tumor necrosis factor) produced from influenza-infected cells. In contrast to the rhinovirus that causes the common cold, influenza does cause tissue damage because it triggers an over-reactive inflammatory response. This massive immune response might produce a life-threatening 'cytokine storm' which causes tissue damage, respiratory distress, multi-organ failure, and death. This effect has been proposed to be the cause of the unusual lethality of both the H5N1 avian influenza, and the 1918 pandemic H1N1 strain. The 1918 flu pandemic was truly global, spreading even to the Arctic and remote Pacific islands. The unusually severe disease killed between two and twenty percent of those infected, as opposed to the more usual flu epidemic mortality rate of 0.1%. Another unusual feature of this pandemic was that it mostly killed young adults, with 99% of pandemic influenza deaths occurring in people under 65, and more than half in young adults 20 to 40 years old. This is unusual since influenza is normally most deadly to the very young (under age 2) and the very old (over age 70). The total mortality of the 1918-1919 pandemic is not known, but it is estimated that 2.5% to 5% of the world's population was killed. As many as 25 million may have been killed in the first 25 weeks. In contrast, HIV/AIDS has killed 25 million in its first 25 years. Later flu pandemics were not so devastating. They included the 1957 Asian flu (type A, H2N2 strain), the 1968 Hong Kong flu (type A, H3N2 strain) and the 1977 Russian flu (type A, H1N1 strain), but even these smaller outbreaks killed millions of people. In later pandemics, antibiotics were available to control secondary infections and this may have helped reduce mortality compared to the Spanish flu of 1918. Influenza type B does not mutate as rapidly of type A, and therefore, does not typically cause pandemic infections but rather is frequently associated with seasonal epidemics. Nonetheless, the cost associated with annual flu epidemics from loss of productivity and life is tremendous.

Influenza (flu) infections are typically limited in scope and severity by the immune system in immunocompetent patients, and flu virus is cleared by 5-10 days. This rapid immune clearance can limit the effectiveness of antivirals on severity of symptoms and length of infection. However, certain patient populations are at risk for complications associated with the influenza infection that can lead to hospitalization and death. The most common complication is pneumonia which can either be primary viral pneumonia, secondary bacterial pneumonia, or a mixture of the two. Other complications affect musculoskeletal, cardiac, or neurologic systems and can include myocarditis, pericarditis, myositis, rhabdomyolysis, and encephalitis. Persons at risk of complications include unvaccinated infants aged 12-24 months, impregnated persons in $2^{nd}$ or $3^{rd}$ trimesters, persons with chronic pulmonary diseases such as asthma, cystic fibrosis, or chronic obstructive pulmonary disease, persons with hemodynamically significant cardiac disease, persons with vascular disease such as sickle-cell anemia, persons with immunosuppressive disorders, persons with chronic renal dysfunction or cancer, persons with neuromuscular disorders, seizure disorders or cognitive dysfunction which may compromise handling of respiratory secretions, adults >65 years old, or residents of long-term care institutions. Vaccination is recommended for the general population and especially emphasized as important for the at risk population, as a preventative measure. However, vaccine effectiveness varies for any given influenza season due to antigenic drift from the vaccine strains considered during vaccine preparation; e.g., in 2014-15 flu season, CDC estimated only 23% effectiveness whereas the effectiveness of most years' vaccines are substantially higher.

Direct antiviral agents have been approved for influenza. Oseltamivir (Tamiflu®) is an FDA approved drug used to treat type A or type B influenza infections. If caught within the first 48 hours of symptom onset, oral oseltamivir decreases severity and length of infection, with the greatest benefit when therapy is started in the first 24 hours of symptom onset. Oseltamivir has also been used for prophylaxis in contacts of flu patients. Oseltamivir is an inhibitor of the influenza virus release from an infected cell that works by inhibiting one of the key surface proteins of the influenza virus, the neuraminidase, which in turn reduces the ability of the virus to infect other respiratory cells. Members of the neuraminidase inhibitor (NAI) family include oral oseltamivir, inhaled zanamivir, and intravenous peramivir. Emergence of NAI-resistance is concerning because of the limited options for influenza treatment, as indicated by the global spread of NAI-resistant type A (H1N1) viruses in the 2008-2009 influenza season. Another antiviral agent, approved in 2018, oral baloxavir marboxil (Xofluza) is a polymerase acidic (PA) endonuclease inhibitor indicated for the treatment of acute uncomplicated influenza in patients 12 years of age and older who have been symptomatic for no more than 48 hours. It is not an NAI agent and instead inhibits the PA protein, an influenza virus-specific enzyme in the viral RNA polymerase complex required for viral gene transcription, resulting in inhibition of influenza virus replication. In one randomized controlled trial, baloxavir had greater efficacy than oseltamivir in adolescents and adults with influenza B virus infection. Similar to NAI use, the emergence of resistance to PA inhibitors has been observed clinically and resistant viruses have mutations in the PA protein. None of the treatment-emergent substitutions associated with reduced susceptibility to baloxavir were identified in virus from pre-treatment respiratory specimens in the clinical studies. Amantadine and rimantadine are an older class of agents approved to prevent or treat influenza type A in patients 17 years or older. Though poorly understood, these agents are believed to inhibit the function of the viral M2 protein and thereby block an early step in the viral replicative cycle. In January 2017, due to high levels of resistance to currently circulating Influenza A viruses, the Centers for Disease Control and Prevention currently (and still valid in 2023) recommends against using amantadine and rimantadine to treat Influenza A. Ribavirin has also been used historically but is no longer recommended. Choice of therapy depends upon whether influenza A or B, approved age groups, local resistance patterns, and contraindications.

These three classes of influenza antivirals are each direct targeting antiviral agents because they bind to viral proteins (NA, PA, or M2, respectively) to exert their efficacy. Binding to viral target protein makes direct antiviral agents susceptible to the emergence of resistance based on mutations of the virus in response to the selective pressures of antiviral use. Indirect antivirals, such as the colchicine binding site inhibitors (CBSI) of tubulin of the current invention, bind to a host target protein whose function is conserved. In general, and certainly for the CBSI's of this invention, mutant host cells likely would not be viable and, consequently, indirect antiviral agents are not as susceptible to the selective pressures that lead to direct antiviral resistance. Moreover, an indirect antiviral agent does bind competitively with or otherwise antagonize the efficacy of a direct antiviral agent, so the use of indirect anti-influenza agents would not be contraindicated with use of existing anti-influenza agents.

Though inflammation in the lungs causes pathology in influenza infections, anti-inflammatory agents devoid of antiviral activity such corticosteroids have limited utility. Most studies have reported that corticosteroid therapy adversely influences influenza-related outcomes. E.g., during the 2009 influenza pandemic, 37% to 55% of the patients admitted to ICUs in Europe received corticosteroids (such as dexamethasone) as part of their treatment. Nonetheless, in a recent meta-analysis report, evidence from observational studies have suggested that corticosteroid therapy for presumed influenza-associated complications was associated with increased mortality.

Poxviridae is a family of double-stranded DNA viruses that includes such pathogens as smallpox (Variola). Smallpox has been declared to be eradicated worldwide and so immunization of smallpox has waned, and correspondingly, a variety of non-variola *Orthopoxvirus* infections such as Monkeypox, aka Mpox, have recently increased in incidence. *Orthopoxviruses* (OPXVs) belonging to the Poxviridae family that infect humans are variola virus (smallpox), vaccinia virus (cowpox) (the virus in the smallpox vaccine called ACAM2000 and the smallpox/monkeypox vaccine called Jynneos), monkeypox virus, horsepox, camelpox, Akhmeta virus and Alaskapox virus. Variola virus, the etiologic cause of smallpox, is the only one that affects humans exclusively, while the others are zoonotic infections that can also be transmitted person-to-person. Poxvirus infections may be localized to the skin or disseminated. The initial site of infection may be the skin, a mucosal surface, or the respiratory tract.

Monkeypox virus belongs to the *Orthopoxvirus* genus of the Poxviridae family. *Orthopoxviruses*, such as monkeypox, can also cause serious clinical illness including, but not limited to encephalitis, severe inflammatory response syndrome, respiratory failure, painful head and neck lymph node swelling with or without associated airway and/or swallowing compromise, extensive dermal disruption during rash phase, and/or other septic syndromes. Since the worldwide eradication of smallpox, the other *Orthopoxviruses* or non-variola *Orthopoxvirus* (NV-OPXV) infections are emerging as a growing public health concern given the potential for spread through international travel, especially among populations that have not been previously vaccinated, and delayed recognition of NV-OPXV infections by healthcare professional who may be less familiar with these infections.

Recent cases of human monkeypox (MPox) in countries outside of west and central Africa underscore the risk of spread of MPox from beyond its normal endemic region and the potential for sustained local transmission. Monkeypox is a disease of global public health importance as it not only affects countries in west and central Africa, but the rest of the world. In 2003, the first monkeypox outbreak outside of Africa was in the United States of America and was linked to contact with infected pet prairie dogs. These pets had been housed with Gambian pouched rats and dormice that had been imported into the country from Ghana. This outbreak led to over 70 cases of monkeypox in the U.S. Monkeypox has also been reported in travelers from Nigeria to Israel in September 2018, to the United Kingdom in September 2018, December 2019, May 2021 and May 2022, to Singapore in May 2019, and to the United States of America in July and November 2021. In May 2022, multiple cases of monkeypox were identified in several non-endemic countries. Studies are currently underway to further understand the epidemiology, sources of infection, and transmission patterns. Before April 2022, monkeypox virus infection in humans was seldom reported outside African regions where it is endemic. Currently, cases are occurring worldwide.

The pathology of Mpox is characterized by an incubation period (interval from infection to onset of symptoms) of usually from 6 to 13 days but can range from 5 to 21 days. The infection can be divided into two periods: (1) The invasion period (lasts between 0-5 days) characterized by fever, intense headache, lymphadenopathy (swelling of the lymph nodes), back pain, myalgia (muscle aches) and intense asthenia (lack of energy). Lymphadenopathy is a distinctive feature of Mpox compared to other diseases that may initially appear similar (chickenpox, measles, smallpox); and (2) The skin eruption period usually begins within 1-3 days of appearance of fever. The rash tends to be more concentrated on the face and extremities rather than on the trunk. It affects the face (in 95% of cases), and palms of the hands and soles of the feet (in 75% of cases). Also affected are oral mucous membranes (in 70% of cases), genitalia (30%), and conjunctivae (20%), as well as the cornea. The rash evolves sequentially from macules (lesions with a flat base) to papules (slightly raised firm lesions), vesicles (lesions filled with clear fluid), pustules (lesions filled with yellowish fluid), and crusts which dry up and fall off. The number of lesions varies from a few to several thousand. In severe cases, lesions can coalesce until large sections of skin slough off. The case fatality ratio of Mpox has historically ranged from 0 to 11% in the general population and has been higher among young children. In recent times, the case fatality ratio has been around 3-6%.

Clinical care for Mpox should be fully optimized to alleviate symptoms, manage complications and prevent long-term sequelae. Patients should be offered fluids and food to maintain adequate nutritional status. Secondary bacterial infections should be treated as indicated. An antiviral agent known as tecovirimat that was developed for smallpox was licensed by the European Medicines Agency (EMA) for monkeypox in 2022 based on data in animal and human studies. It is not yet widely available. Tecovirimat inhibits the function of a major envelope protein required for the production of extracellular virus. The drug prevents the virus from leaving an infected cell, hindering the spread of the virus within the body. While the effectiveness of tecovirimat in treating human non-variola *Orthopoxvirus* infections, including Mpox, has not been evaluated, it may be reasonable to anticipate potential treatment benefit based on animal efficacy data that supported FDA-approval for smallpox treatment and limited clinical uses of tecovirimat in the treatment of NV-OPXV infected individuals to date. Tecovirimat has been shown to be effective against various *Orthopoxviruses* in multiple animal challenge models. Tecovirimat was approved for smallpox under the FDA's Animal Rule, which allows efficacy findings from adequate and well-controlled animal studies to support an FDA approval when it is not feasible or ethical to conduct efficacy trials in humans. Given the lack of well tested pharmacotherapy for non-variola *Orthopoxvirus* infections including Mpox and their increasing incidence worldwide including in non-endemic regions, there is a dire need to discover new pharmacotherapeutics for these non-variola *Orthopoxvirus* infections.

Viruses have efficient mechanisms that take control of their host's cellular machinery to carry out viral replication, assembly, and to exit (egress) from the cell to spread infectious virions. Given the spatial distances between the point of virion entry at the plasma membrane to the location in the cell where DNA or RNA replication (nucleus) and viral assembly occur in the endoplasmic reticulum and Golgi, and then the newly generated virions have to travel back out to the plasma membrane to egress out of the cell, it is no surprise that the virus's most critical initial task is to hijack the host's internal transportation system, the cytoskeleton. The cytoskeleton is composed of three major types of protein filaments: microfilaments (actin), microtubules (tubulin), and intermediate filaments. The principal ones involved in viral replication and trafficking (transport) are microtubules and microfilaments since these are two main filament systems involved in intracellular transport.

Microtubules are important for cell shape, transport, motility, and cell division. Microtubules are dynamic long polar fibers/filaments that result from the polymerization of α and β tubulin heterodimer subunits with a positive end located at the plasma membrane and a minus end facing the nucleus at the microtubule organizing center (MTOC). From the MTOC, microtubule fibers radiate out from the nuclear area towards the periphery of the cell. Microtubules are dynamic network systems, meaning that, they undergo rapid polymerization adding α and β tubulin subunits heterodimers together to create a growing polymer chain, and subsequent rapid depolymerization (remove α and β tubulin subunits heterodimers) to deconstruct and shrink the polymer chain. This "dynamic" growing and shrinking ability of microtubules serves the constantly changing transportation requirements of the cell. Large macromolecules, like viruses, engage with specialized motor proteins (kinesins and dyneins). Kinesins and dyneins attach, carry, and move the virus cargo up and down these microtubule tracks, like train cars, to travel long distance to reach the different compartments within the cell.

As many human and animal viruses originated from other mammals and most eukaryotic cells contain microtubules, there appears to be a conserved microtubule dependent coronavirus replication across species. Furthermore, viruses may have evolved microtubule-binding motifs or similar amino acid sequences complementary to motifs in kinesins and dyneins for successful trafficking interactions. Examples like Mouse Hepatitis Virus CoV use microtubules for neuronal spread and the Feline Infectious Peritonitis Virus (FIPV) is transported by microtubules toward the MTOC. For the porcine transmissible gastroenteritis virus (TGEV), upregulation of both α and β tubulin subunits occurs after infection. Thus, focusing on the cytoskeleton network as a drug target with the goal of impairing intracellular trafficking and disrupting virus and host interactions may be an effective way to treat viral infections.

Viruses are obligate intracellular parasites and therefore, depend solely on the cellular machinery for membrane trafficking, nuclear import and export, and gene expression. Incoming viral particles move from the cell surface to intracellular sites of viral transcription and replication. During assembly and egress, subviral nucleoprotein complexes and virions travel back to egress the plasma membrane. Because diffusion of large molecules is severely restricted in the cytoplasm, viruses use ATP-hydrolyzing molecular motors of the host for propelling along the microtubules, which are the intracellular highways.

Microtubules are cytoskeletal filaments consisting of α- and β-tubulin heterodimers and are involved in a wide range of cellular functions, including shape maintenance, vesicle transport, cell motility, and division. Tubulin is the major structural component of the microtubules and a verified target for a variety of antiviral drugs. Compounds that are able to interfere with microtubule-tubulin equilibrium in cells are effective in the treatment of viruses as a virus generally uses microtubules as a source of transportation within the cell. Other compounds that interfere with microtubule-tubulin equilibrium in cells, such as paclitaxel and vinblastine, are limited by their toxicity.

Drugs that target the cytoskeleton, especially the microtubule components are important therapeutic agents for cancer and inflammation. The clinical activity of these compounds is dictated by the location that these compounds bind on the α and β-tubulin heterodimers that compose the microtubule filament. Three major binding sites on α and β-tubulin subunits have been identified as taxanes-, vinca alkaloid-, and colchicine-binding sites. Such drugs are commonly classified into two major categories: microtubule-stabilizing (e.g., taxanes) and microtubule-destabilizing, or depolymerizing agents (e.g., vinca alkaloids and colchicine).

Colchicine has a narrow therapeutic index with no clear distinction between nontoxic, toxic, and lethal doses. Metabolically, colchicine is eliminated via P-glycoprotein (P-gp;

also known as Multi-Drug Resistance 1 (MDR1) protein). Drug-drug interactions are common with CYP3A4 and P-glycoprotein inhibitors which can increase colchicine blood concentrations to toxic levels leading to colchicine poisoning and death. Life-threatening and fatal toxicities have been observed when colchicine is administered with P-gp or strong CYP3A4 inhibitors even at approved therapeutic doses. Additional serious toxicities including myelosuppression, disseminated intravascular coagulation, and cell damage in renal, hepatic, circulatory, and central nervous systems have been observed with approved therapeutic doses of colchicine. These observed serious adverse events limit the clinical use of colchicine.

The antiviral activity of combretastatin, colchicine, and colchicine derivatives and their selected prodrugs against DENV and ZIKV in cell culture was observed at low micromolar and sub-micromolar concentrations. A major problem with taxanes, as with many biologically active natural products, is its lipophilicity and lack of solubility in aqueous systems. This leads to the use of emulsifiers like Cremophor EL and Tween 80 in clinical preparations, which leads to serious hypersensitivity reactions.

Nocodazole is a synthetic compound identified in a screen for anthelminthic agents. Nocodazole is a microtubule depolymerization agent as it binds to free tubulin heterodimers and prevents them from incorporating into microtubules. It has not been used clinically because of poor bioavailability and high toxicity.

The cellular and viral solution to master intracellular trafficking is an organized network or filaments including microtubules. Cells require microtubules for long-term normal physiology, and viruses are obligate intracellular parasites that completely depend on the physiology of the host cell. Thus, it is no surprise that Orthomyxoviridae and Poxviridae viral life cycles require microtubules for efficient replication. The viral binding sites on microtubulin might provide new targets for antiviral therapy. The inventions of this application address a novel method of interfering with microtubules of the cytoskeleton to prevent Orthomyxoviridae and Poxviridae virus intracellular transportation, replication, and egress.

SUMMARY OF THE INVENTION

The invention encompasses methods of treating an Orthomyxoviridae infection in a subject in need thereof by administering to the subject a formulation having a therapeutically effective amount of a compound of Formula (I):

(I)

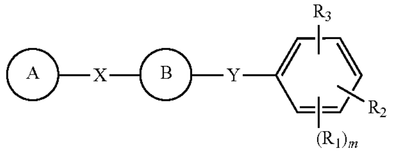

wherein

A is phenyl, indolyl, or indazolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole or benzimidazole, optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond or NH;

Y is a bond or —C═O; and m is 1-3, or a pharmaceutically acceptable salt, hydrate, polymorph, or isomer thereof.

In an embodiment of the invention, the methods of treating an Orthomyxoviridae infection encompass compounds of Formula I wherein A is phenyl or indolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole, optionally substituted with at least one of $(C_1\text{-}C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond or NH;

Y is a bond or —C═O; and m is 1-3, or a pharmaceutically acceptable salt, hydrate, polymorph, or isomer thereof.

In another embodiment of the invention, the methods of treating an Orthomyxoviridae infection encompass compounds of Formula I wherein A is phenyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole, optionally substituted with at least one of $(C_1\text{-}C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond or NH;

Y is a bond or —C═O; and m is 1-3, or a pharmaceutically acceptable salt, hydrate, polymorph, or isomer thereof.

In yet another embodiment of the invention, the methods of treating an Orthomyxoviridae infection encompass compounds of Formula I wherein A is indolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is a bond or —C═O; and m is 1-3, or a pharmaceutically acceptable salt, hydrate, polymorph, or isomer thereof.

An embodiment of the invention, the methods of treating an Orthomyxoviridae infection encompass compounds of Formula I wherein A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond;

Y is —C═O; and m is 1-3, or a pharmaceutically acceptable salt, hydrate, polymorph, or isomer thereof.

Another embodiment of the invention encompasses methods of treating an Orthomyxoviridae infection in a subject in need thereof by administering to the subject a formulation having a therapeutically effective amount of a compound of the Formula VII:

(VII)

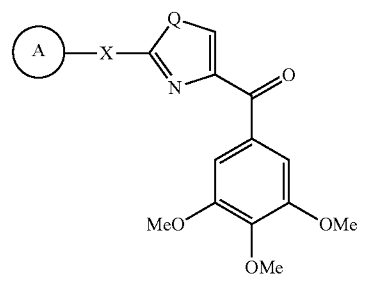

wherein

X is a bond or NH;

Q is S or NH; and

A is a phenyl, indolyl, or indazolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof. In yet another embodiment, the method encompasses compounds of Formula VII wherein Q is S. In another embodiment of the invention, the method encompasses compounds of Formula VII wherein X is NH. In yet another embodiment of the invention, the method encompasses compounds of Formula VII, wherein X is a bond; Q is NH; and A is an indolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

An embodiment of the invention encompasses methods of treating an Orthomyxoviridae infection in a subject in need thereof by administering to the subject a formulation having a therapeutically effective amount of a compound of the Formula VII(c):

VII(c)

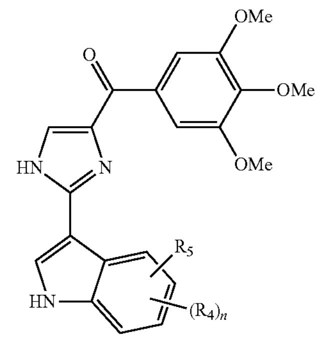

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, polymorph, or isomer thereof.

Another embodiment of the invention, encompasses methods of treating an Orthomyxoviridae infection in a subject in need thereof by administering to the subject a formulation having a therapeutically effective amount of a compound 17ya represented:

(17ya)

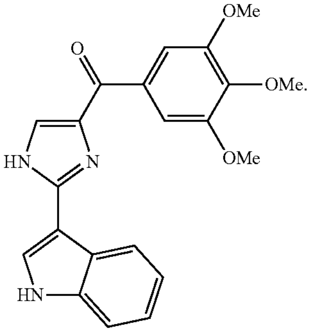

Yet another embodiment of the invention encompasses methods of treating Orthomyxoviridae infections wherein said Orthomyxoviridae infection is caused by an influenza virus. In another embodiment, the influenza virus is influenza A. In one of these embodiments, the influenza A virus has the serotype H1N1. In one of these embodiments, the influenza A virus has the serotype H2N2. In one of these embodiments, the influenza A virus has the serotype H3N2. In one of these embodiments, the influenza A virus has the serotype H5N1. In one of these embodiments, the influenza A virus has the serotype H7N7. In one of these embodiments, the influenza A virus has the serotype H7N9. In one of these embodiments, the influenza A virus has the serotype H1N2 infects pigs and humans. In others of these embodiments, the influenza A virus has at least one of the serotypes of H9N2, H7N2, H7N3, H10N7, or others as known by the skilled artisan.

In another embodiment, the influenza virus is influenza B. In some embodiments, the influenza B viruses are further classified into one of two lineages: B/Yamagata and B/Victoria. In one of these embodiments, the influenza B virus is classified as lineage B/Yamagata. In one of these embodiments, the influenza B virus is classified as lineage B/Victoria. In another embodiment, the influenza virus is influenza D. In another embodiment, the influenza virus is influenza C.

A further embodiment of the invention encompasses methods of treating a subject with an influenza infection at risk for influenza complications such as unvaccinated infants aged 12-24 months, persons with chronic pulmonary diseases such as asthma, cystic fibrosis, or chronic obstructive pulmonary disease, persons with hemodynamically significant cardiac disease, persons with vascular disease such as sickle-cell anemia, persons with immunosuppressive disorders, persons with chronic renal dysfunction or cancer, persons with neuromuscular disorders, seizure disorders or cognitive dysfunction which may compromise handling of respiratory secretions, adults >65 years old, or residents of long-term care institutions. Another embodiment of the invention encompasses methods wherein treating a subject with influenza infection reduces mortality. Another embodiment of the invention encompasses methods wherein treating a subject with influenza infection at risk for complications reduces mortality. Another embodiment of the invention encompasses methods wherein treating a subject with influenza infection reduces morbidity. Another embodiment of the invention encompasses methods wherein treating a subject with influenza infection at risk for pneumonia reduces morbidity. Another embodiment of the invention encompasses methods wherein treating a subject with influenza infection reduces risk of developing pneumonia. Another embodiment of the invention encompasses methods of treating a subject with influenza infection with viral pneumonia. Another embodiment of the invention encompasses methods wherein treating a subject with influenza infection reduces mortality or complication in subjects >65 years of age. Another embodiment of the invention encompasses prophylactic treatment influenza. In one embodiment, an influenza infection is prevented or lessened in severity in a close contact following exposure to an individual with an initial influenza infection.

Yet another embodiment of the invention, the methods further comprise at least one additional therapy. An embodiment of the method further comprises a second antiviral therapy such as a neuraminidase inhibitor, an M2 inhibitor, a PA inhibitor, oseltamivir (Tamiflu), zanamivir (Relenza), laninamivir (Inavir), peramivir, rimantadine, amantadine, baloxavir marboxil (Xofluza), ribavirin, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. An embodiment of the method further comprises an additional therapy such as an NAI or PA inhibitor, and/or dexamethasone or other corticosteroids. Yet another embodiment of the methods includes a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

The invention further encompasses methods of treating a Poxviridae infection in a subject in need thereof by administering to the subject a formulation having a therapeutically effective amount of a compound of Formula (I)

(I)

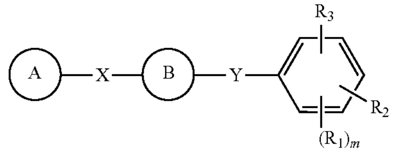

wherein

A is phenyl, indolyl, or indazolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole or benzimidazole, optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond or NH;

Y is a bond or —C═O; and m is 1-3, or a pharmaceutically acceptable salt, hydrate, polymorph, or isomer thereof.

In an embodiment of the invention, the methods of treating a Poxviridae infection encompass compounds of Formula I wherein A is phenyl or indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is a bond or —C═O; and m is 1-3, or a pharmaceutically acceptable salt, hydrate, polymorph, or isomer thereof.

In another embodiment of the invention, the methods of treating a Poxviridae infection encompass compounds of Formula I wherein A is phenyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is a bond or —C═O; and m is 1-3, or a pharmaceutically acceptable salt, hydrate, polymorph, or isomer thereof.

In yet another embodiment of the invention, the methods of treating a Poxviridae infection encompass compounds of Formula I wherein A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond or NH;

Y is a bond or —C═O; and m is 1-3, or a pharmaceutically acceptable salt, hydrate, polymorph, or isomer thereof.

An embodiment of the invention, the methods of treating a Poxviridae infection encompass compounds of Formula I wherein A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

B is an imidazole, optionally substituted with at least one of ($C_1$-$C_4$)alkyl;

$R_1$, $R_2$ and $R_3$ are independently at least one of hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

X is a bond;

Y is —C═O; and m is 1-3, or a pharmaceutically acceptable salt, hydrate, polymorph, or isomer thereof.

Another embodiment of the invention encompasses methods of treating a Poxviridae infection in a subject in need thereof by administering to the subject a formulation having a therapeutically effective amount of a compound of the Formula VII:

(VII)

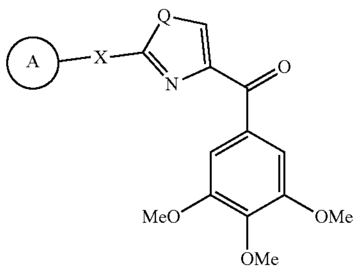

wherein

X is a bond or NH;

Q is S or NH; and

A is a phenyl, indolyl, or indazolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof. In yet another embodiment, the method encompasses compounds of Formula VII wherein Q is S. In another embodiment of the invention, the method encompasses compounds of Formula VII wherein X is NH. In yet another embodiment of the invention, the method encompasses compounds of Formula VII, wherein X is a bond; Q is NH; and A is an indolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

An embodiment of the invention encompasses methods of treating a Poxviridae infection in a subject in need thereof by administering to the subject a formulation having a therapeutically effective amount of a compound of the Formula VII(c):

VII(c)

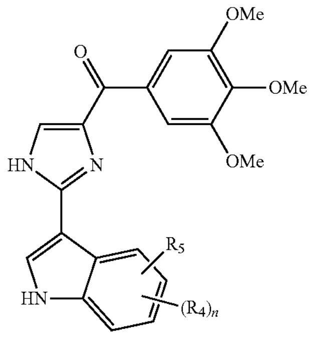

wherein $R_4$ and $R_5$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, OC(O)$CF_3$, —$OCH_2Ph$, —NHCO—($C_1$-$C_4$)alkyl, COOH, —C(O)Ph, C(O)O—($C_1$-$C_4$)alkyl, C(O)H, —C(O)$NH_2$ or $NO_2$; and n is 1-4; or a pharmaceutically acceptable salt, hydrate, polymorph, or isomer thereof.

Another embodiment of the invention, encompasses methods of treating a Poxviridae infection in a subject in need thereof by administering to the subject a formulation having a therapeutically effective amount of a compound 17ya represented:

(17ya)

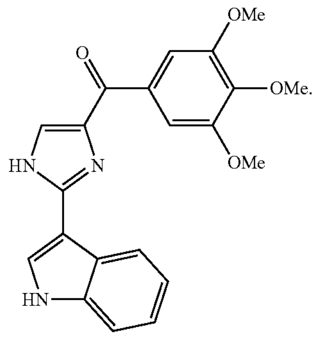

Yet another embodiment of the invention encompasses methods of treating Poxviridae infections wherein the viral infection is caused by a virus of the *Orthopoxvirus* genus. In one of these embodiments, the *Orthopoxvirus* is smallpox. In one of these embodiments, the *Orthopoxvirus* is Monkeypox. In one of these embodiments, the *Orthopoxvirus* is a vaccinia virus. In one of these embodiments, the *Orthopoxvirus* is any one of coxpox horsepox, camelpox, Akhmeta virus, and Alaskapox, or other *Orthopoxviruses* as known by the skilled artisan.

A further embodiment of the invention encompasses methods of treating the symptoms of a Poxviridae infection such as encephalitis, severe inflammatory response syndrome, respiratory failure, painful head and neck lymph node swelling, extensive dermal eruption, and septic syndromes.

Yet another embodiment of the invention, the methods further comprise at least one additional therapy. An embodiment of the method further comprises a second antiviral therapy such as a neuraminidase inhibitor, an M2 inhibitor, a PA inhibitor, oseltamivir (Tamiflu), zanamivir (Relenza), laninamivir (Inavir), peramivir, rimantadine, amantadine, baloxavir marboxil (Xofluza), ribavirin, tecovirimat, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. An embodiment of the method further comprises an additional therapy such as tecovirimat. Yet another embodiment of the methods includes a second antiviral therapy that is at least one of tecovirimat, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

An embodiment of the invention encompasses methods wherein the compound of the invention is administered in an amount of about 1 mg to about 100 mg. Another embodiment of the invention encompasses methods wherein the compound of the invention is administered in an amount of about 4 to about 90 mg. Another embodiment of the invention encompasses methods wherein the compound of the invention is administered in an amount of about 9 mg to about 18 mg. Another embodiment of the invention encompasses methods wherein the compound of the invention is administered in an amount of about 4 mg to about 45 mg. In yet another embodiment of the method encompasses at least one pharmaceutically acceptable excipient.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A illustrates the effect of Compound 17ya on percent bodyweight change (%) days after post-H1N1 administration. FIG. 2B illustrates the effect of Compound 17ya on bodyweight (g) days after post-H1N1 administration.

FIG. 3A illustrates the effect on total cell count of Compound 17ya, vehicle, dexamethasone, and oseltamivir. FIG. 3B illustrates the effect on neutrophil count of Compound 17ya, vehicle, dexamethasone, and oseltamivir. FIG. 3C illustrates the effect on mononuclear cells of Compound 17ya, vehicle, dexamethasone, and oseltamivir.

FIG. 3D illustrates the effect on lymphocytes of Compound 17ya, vehicle, dexamethasone, and oseltamivir. FIG. 3E illustrates the effect on eosinophils of Compound 17ya, vehicle, dexamethasone, and oseltamivir. The following abbreviations are used: s.e.m. is the standard error of the mean. $^{+++}p<0.001$ when compared to the vehicle/vehicle group. $p<0.01$, $*p<0.001$ when compared to the vehicle/H1N1 group.

FIG. 4A illustrates the effect on TNFα (pg/mL) of Compound 17ya, vehicle, dexamethasone, and oseltamivir. FIG. 4B illustrates the effect on IFN-γ of Compound 17ya, vehicle, dexamethasone, and oseltamivir. FIG. 4C illustrates the effect on IL-6 of Compound 17ya, vehicle, dexamethasone, and oseltamivir. FIG. 4D illustrates the effect on KC of Compound 17ya, vehicle, dexamethasone, and oseltamivir. FIG. 4E illustrates the effect on IP-10 of Compound 17ya, vehicle, dexamethasone, and oseltamivir. The following abbreviations are used: s.e.m. is the standard error of the mean. $+++p<0.001$ when compared to the vehicle/vehicle group. $*\ p<0.05$, $\ p<0.01$, $*\ p<0.001$, when compared to the vehicle/H1N1 challenged group.

DETAILED DESCRIPTION OF THE INVENTION

Figure 1:
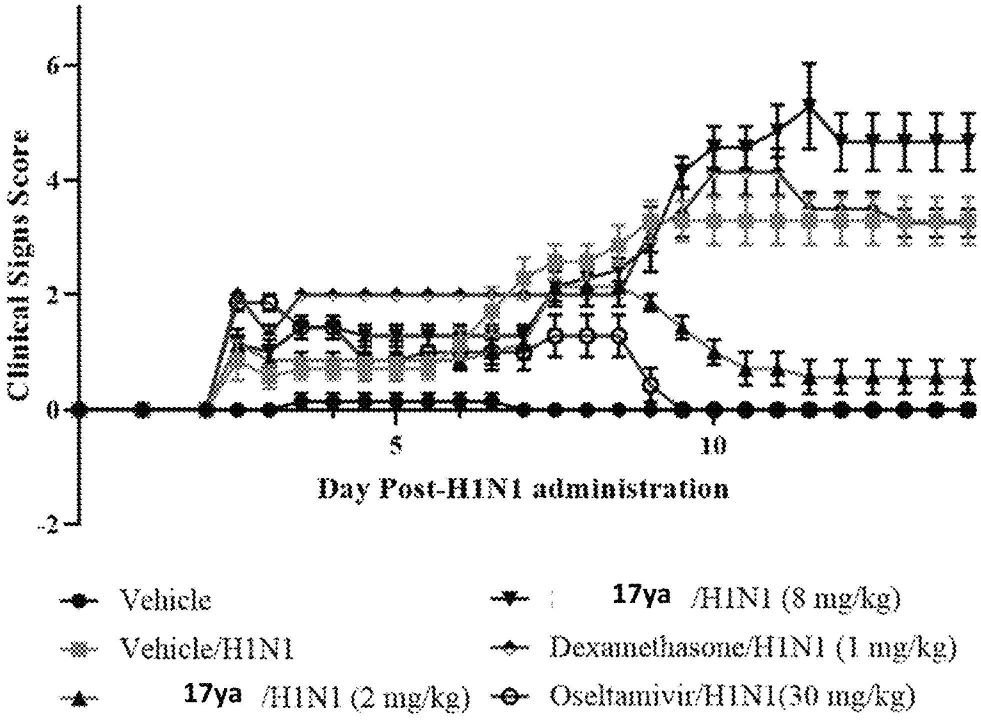
FIG. 1 illustrates the clinical sign score over the post H1N1 administration period in mice.

Microtubule based macromolecule intracellular transport is a critical aspect of viral replication. For viral infection, expression of viral proteins alters the organization of these microtubular networks to serve their need to replicate and spread infectious virion. Microtubules not only facilitate infection, but microtubules are actively manipulated by viruses. Furthermore, cytoskeleton disruptor agents suppress viral infection. Not to be limited by theory, the invention is based, in part, on the fact that tubulin interacts with the cytoplasmic domains of Orthomyxoviridae and Poxviridae proteins. The reduction in infectious virus titer may follow by treatment with a drug that causes microtubule depolymerization, mainly because there is less cytoplasmic proteins present at the assembly site due to impaired cytoplasmic protein microtubule transport and that the incorporation process of cytoplasmic proteins itself into virions is tubulin dependent. Furthermore, disruption of microtubule trafficking impaired the egress out of the cell of these poorly assembled virion with less cytoplasmic proteins, making them less infectious. A microtubule depolymerizing agent may be effective in treating viral infection by disrupting microtubule trafficking which is critical for the virus replication cycle.

The present invention is directed to antiviral therapy for Orthomyxoviridae or Poxviridae infections based upon the disruption of the cytoskeleton disruptor activity of the claimed compounds that interrupts the intracellular microtubules trafficking network. Intended to overcome the disadvantages of the prior art, including but not limited to toxicity, the methods are directed to compounds specifically activated within Orthomyxoviridae or Poxviridae virus-infected cell or within those cells that are preferably targeted by the virus. Not to be limited by theory, the invention is based upon Orthomyxoviridae or Poxviridae virus reliance on the host cell machinery for successful replication. For instance, an Orthomyxoviridae or Poxviridae virus uses the host secretory pathway during their replication cycle. The vesicular transport on secretory pathways is mostly mediated by microtubules and the corresponding motor proteins. The disruption of microtubules leads to decreased replication, reduced amount of released infectious particles, and decreased virus yield. Consequently, the virus load is reduced, thereby establishing an antiviral therapy. To address the need for novel, rapidly acting antiviral compounds for Orthomyxoviridae and Poxviridae infections, the inventors proposed a method of treating virus infections by the administration of the compounds described below.

In a particular embodiment, the compounds of the invention are orally bioavailable non-colchicine molecules that bind the "colchicine binding site" of α and β tubulin and inhibits tubulin polymerization into microtubules at low nanomolar concentrations. These colchicine binding site inhibitors (CBSIs) have a broad scope of structures but generally possess predominantly indolyl, phenyl, or indazolyl A-rings (leftmost ring in Formula I), direct bond or amino linkers (X) between A- and B-rings, imidazole, thiazole, or benzimidazole B-rings, predominantly methanone linkers (Y) between the B-ring and C-ring (rightmost ring in Formula I), and substituted phenyl C-rings. The compounds used in the methods are neither a substrate for multidrug resistance proteins (MDRs) including P-gp, MRPs, and BCRP, nor CYP3A4. The compounds used in the methods also decrease the transcription of βI, βIII, and βIV-tubulin isoforms (Li 2012). Further, the compounds used in the methods of the invention have good safety as they do not cause significant neurotoxicity, neutropenia, or myelosuppression and are well tolerated. As outlined herein, CBSI's of the invention including Compound 17ya show promise in treating non-variola Orthopoxvriuses due to their ability to prevent the microtubule network necessary for viral cell entry, trafficking in the cells, viral replication, viral egress, etc. As outlined herein, Compound 17ya and CBSIs of this invention show promise in treating Orthomyxoviruses and Poxviridae infections due to their ability to prevent the microtubule network necessary for viral cell entry, trafficking in the cells, viral replication, viral egress, etc.

The indirect antivirals agents of this invention bind to a conserved host target which also suggests broad antiviral efficacy across diverse families of viruses as has been demonstrated for coronaviruses previously, and now members of the Orthomyxoviridae and Poxviridae families of pathogenic viruses. An advantage of indirect antiviral agents regarding the lack of selective pressures with their use is operative regardless of whether the viral infection is an influenza infection or other member of the Orthomyxoviridae family, or Mpox or other member of the Poxviridae family, or any other virus susceptible to the colchicine binding site inhibitors of this invention.

The three FDA approved classes of influenza antivirals are each direct targeting antiviral agents because they bind to viral proteins (NA, PA, or M2, respectively) to exert their efficacy. Binding to viral target protein makes direct antiviral agents susceptible to the emergence of resistance based on mutations of the virus in response to the selective pressures of antiviral use. Indirect antivirals, such as the colchicine binding site inhibitors (CBSI) of tubulin of the current invention, bind to a host target protein whose function is conserved. In general, and certainly for the CBSI's of this invention, mutant host cells likely would not be viable and, consequently, indirect antiviral agents are not as susceptible to the selective pressures that lead to direct antiviral resistance. Moreover, an indirect antiviral agent does bind competitively with or otherwise antagonize the efficacy of a direct antiviral agent, so the use of indirect anti-influenza agents would not be contraindicated with use of existing anti-influenza agents.

Further, the methods encompassed by the invention include compounds capable of influencing microtubule dynamics such that the compounds could be administered in sub-cytotoxic concentrations as systemic antiviral agents. This is in strong contrast to colchicine and other tubulin polymerization destabilizers used as antiviral drugs which possess high systemic toxicity.

The invention encompasses methods of treating an Orthomyxoviridae infection in a subject in need thereof by administering to the subject a formulation having a therapeutically effective amount of a compound of Formula (I)

(I)

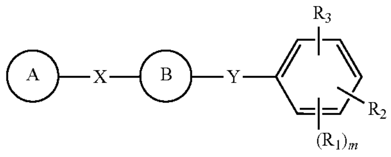

wherein

A is phenyl, indolyl, or indazolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole, thiazole, or benzimidazole, optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond, NH, $(C_1\text{-}C_4)$alkyl, O, or S;

Y is a bond, —C═O, —C═S, $SO_2$, SO or S; and m is 1-3, or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of Formula (II):

II

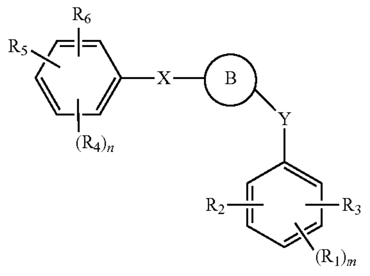

wherein

B is an imidazole, thiazole, or benzimidazole, optionally independently substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$, $R_3$, $R_4$, $R_5$ and $R_6$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond, NH, or $(C_1\text{-}C_4)$alkyl;

Y is a bond or —C═O;

n is 1-3; and m is 1-3; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of Formula (III):

(III)

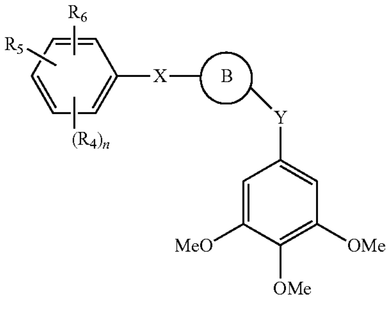

wherein

B is an imidazole, thiazole or benzimidazole, optionally independently substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_4$, $R_5$ and $R_6$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, $—OCH_2Ph$, —NHCO—$(C_1$-$C_4)$alkyl, COOH, —C(O)Ph, C(O)O—$(C_1$-$C_4)$alkyl, C(O)H, $—C(O)NH_2$ or $NO_2$;

X is a bond or NH;

Y is —C═O; and n is 1-3; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of Formula (IV):

(IV)

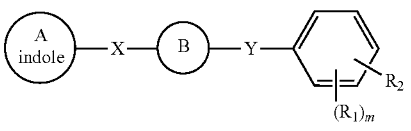

wherein ring A is an indolyl, optionally substituted with at least one of $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, $—CH_2CN$, $NH_2$, hydroxyl, $OC(O)CF_3$, $—OCH_2Ph$, —NHCO—$(C_1$-$C_4)$ alkyl, COOH, —C(O)Ph, C(O)O—$(C_1$-$C_4)$alkyl, C(O) H, $—C(O)NH_2$ or $NO_2$;

B is an imidazole or benzimidazole, optionally independently substituted with at least one of $(C_1$-$C_4)$alkyl, halo$(C_1$-$C_4)$alkyl, O—$(C_1$-$C_4)$alkyl, O-halo$(C_1$-$C_4)$alkyl, F, Cl, Br, I, CN, $—CH_2CN$, hydroxyl, or $NO_2$;

$R_1$ and $R_2$ are independently at least one of hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, $—CH_2CN$, $NH_2$, hydroxyl, $OC(O)CF_3$, $—OCH_2Ph$, —NHCO—$(C_1$-$C_4)$alkyl, COOH, —C(O)Ph, C(O)O—$(C_1$-$C_4)$alkyl, C(O)H, $—C(O)NH_2$ or $NO_2$;

X is a bond or NH;

Y is a bond or —C═O; and m is 1-4; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of Formula IV(a):

IV(a)

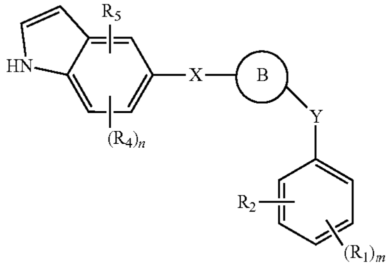

B is an imidazole or benzimidazole, optionally independently substituted with at least one of $(C_1$-$C_4)$alkyl, halo$(C_1$-$C_4)$alkyl, O—$(C_1$-$C_4)$alkyl, O-halo$(C_1$-$C_4)$alkyl, F, Cl, Br, I, CN, $—CH_2CN$, hydroxyl, or $NO_2$;

$R_1$, $R_2$, $R_4$ and $R_5$ are independently hydrogen, $(C_1$-$C_4)$ alkyl, halo$(C_1$-$C_4)$alkyl, O—$(C_1$-$C_4)$alkyl, O—$(C_1$-$C_4)$ haloalkyl, $(C_1$-$C_4)$alkylamino, amino$(C_1$-$C_4)$alkyl, F, Cl, Br, I, CN, $—CH_2CN$, $NH_2$, hydroxyl, $OC(O)CF_3$, $—OCH_2Ph$, —NHCO—$(C_1$-$C_4)$alkyl, COOH, —C(O) Ph, C(O)O—$(C_1$-$C_4)$alkyl, C(O)H, $—C(O)NH_2$ or $NO_2$;

X is a bond or NH;

Y is a bond or —C═O;

n is 1-2; and m is 1-4; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of Formula (V):

(V)

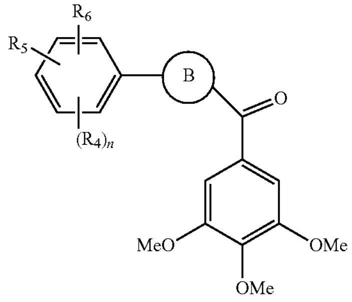

B is an imidazole or benzimidazole, optionally independently substituted with at least one of $(C_1$-$C_4)$alkyl, halo$(C_1$-$C_4)$alkyl, O—$(C_1$-$C_4)$alkyl, O-halo$(C_1$-$C_4)$alkyl, F, Cl, Br, I, CN, $—CH_2CN$, hydroxyl, or $NO_2$;

$R_4$, $R_5$ and $R_6$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, $—CH_2CN$, $NH_2$, hydroxyl, $OC(O)CF_3$, $—OCH_2Ph$, —NHCO—$(C_1$-$C_4)$alkyl, COOH, —C(O) Ph, C(O)O—$(C_1$-$C_4)$alkyl, C(O)H, $—C(O)NH_2$ or $NO_2$;

n is 1-3; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of the Formula (VI):

(VI)

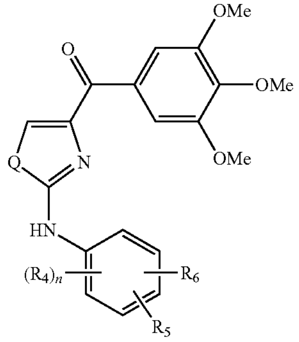

wherein $R_4$, $R_5$ and $R_6$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

Q is S or NH; and n is 1-3; or a pharmaceutically acceptable salt, hydrate, polymorph, or isomer thereof.

Preferably, the variables for the compounds of Formula (VI) are $R_4$, $R_5$ and $R_6$ are independently hydrogen, ($C_1$-$C_4$) alkyl, halo($C_1$-$C_4$)alkyl, O—($C_1$-$C_4$)alkyl, O($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; Q is S or NH; and n is 1-3; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of the Formula VI in the following Table 1A:

TABLE 1A

| Formula VI | Compound | $R_4$ | $R_5$ | $R_6$ | Q |
|---|---|---|---|---|---|
| 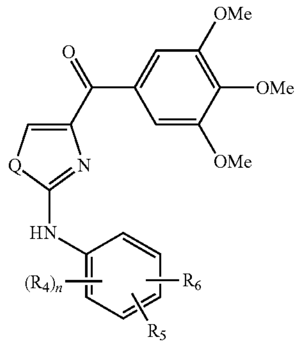 | 5e | H n = 1 | H | H | N |

The invention also encompasses methods of treating an Orthomyxoviridae infection in a subject in need thereof by administering to the subject a formulation having a therapeutically effective amount of a compound of the Formula VII:

(VII)

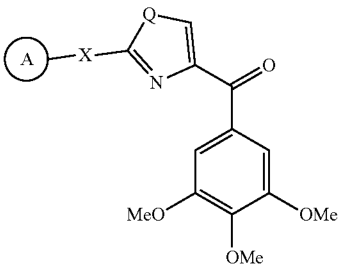

wherein

X is a bond, NH or S;

Q is S or NH; and

A is a phenyl, indolyl, or indazolyl ring optionally substituted with at least one of ($C_1$-$C_4$)alkyl, halo($C_1$-$C_4$) alkyl, O—($C_1$-$C_4$)alkyl, O—($C_1$-$C_4$)haloalkyl, ($C_1$-$C_4$) alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; or a pharmaceutically acceptable salt, hydrate, polymorph, or isomer thereof.

Examples of compounds of Formula VII include, but are not limited to, (2-(phenylamino)-1H-imidazol-4-yl)(3,4,5-trimethoxyphenyl)methanone (5e), (2-(phenylamino)-1H-imidazol-4-yl)(3,4,5-trimethoxyphenyl)methanone hydrochloride salt (5He), and (2-(1H-indol-3-yl)-1H-imidazol-4-yl)(3,4,5-trimethoxyphenyl)methanone (17ya).

Preferably, the variables in the compounds of Formula VII are X is a bond; Q is NH; and A is an indolyl ring optionally substituted with at least one of ($C_1$-$C_4$)alkyl, halo($C_1$-$C_4$) alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of the Formula VII(a):

VII(a)

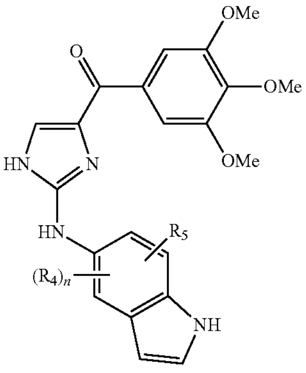

wherein $R_4$ and $R_5$ are independently hydrogen, ($C_1$-$C_4$) alkyl, halo($C_1$-$C_4$)alkyl, O—($C_1$-$C_4$)alkyl, O—($C_1$-$C_4$) haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; and n is 1-4; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of the Formula VII(b):

VII(b)

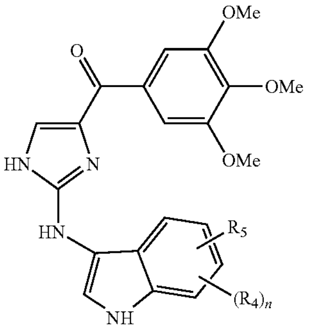

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

The invention also encompasses methods of treating an Orthomyxoviridae infection in a subject in need thereof by administering to the subject a formulation having a therapeutically effective amount of a compound of the Formula VII(c):

VII(c)

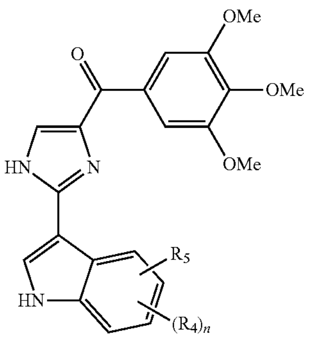

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof. Examples of compounds of Formula VII(c) include, but are not limited to, (2-(1H-indol-3-yl)-1H-imidazol-4-yl)(3,4,5-trimethoxyphenyl)methanone (17ya).

The invention also encompasses methods of treating an Orthomyxoviridae infection in a subject in need thereof by administering to the subject a formulation having a therapeutically effective amount of a compound of the Formula VII(c):

VII(c)

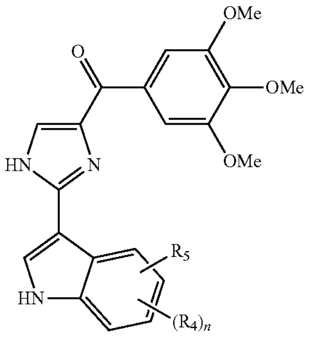

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, F, Cl, Br, I, or CN; and n is 1-4; or a pharmaceutically acceptable salt, hydrate, polymorph, or isomer thereof. Examples of compounds of Formula VII(c) include, but are not limited to, (2-(1H-indol-3-yl)-1H-imidazol-4-yl)(3,4,5-trimethoxyphenyl)methanone (17ya).

The invention also encompasses methods of treating an Orthomyxoviridae infection in a subject in need thereof by administering to the subject a formulation having a therapeutically effective amount of a compound of the Formula 17ya:

(17ya)

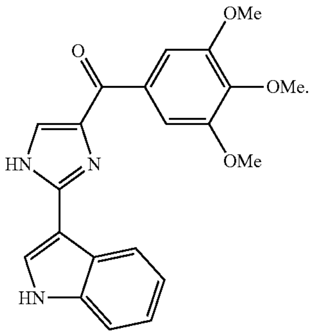

The invention also encompasses methods of treating an Orthomyxoviridae infection in a subject in need thereof by administering to the subject a formulation having a therapeutically effective amount of a compound of the Formula in the following Table 1B:

TABLE 1B
| compound | Structure |
|---|---|
| 8 | 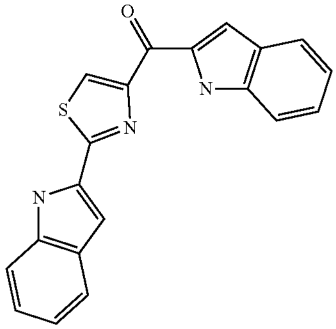 [SMILES: O=C(c1csc(-c2cc3ccccc3[nH]2)n1)c1cc2ccccc2[nH]1] |
| 9 | 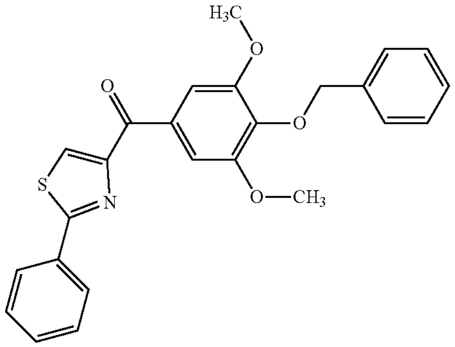 [SMILES: COc1cc(C(=O)c2csc(-c3ccccc3)n2)cc(OC)c1OCc1ccccc1] |
| 10 | 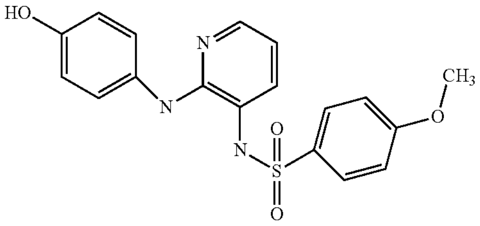 [SMILES: COc1ccc(S(=O)(=O)Nc2cccnc2Nc2ccc(O)cc2)cc1] |
| 11 | 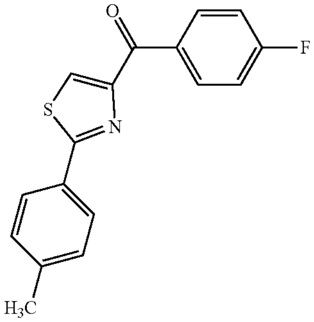 [SMILES: Cc1ccc(-c2nc(C(=O)c3ccc(F)cc3)cs2)cc1] |
| 12 | 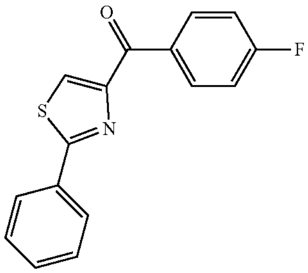 [SMILES: O=C(c1ccc(F)cc1)c1csc(-c2ccccc2)n1] |
TABLE 1B-continued
| compound | Structure |
|---|---|
| 13 | 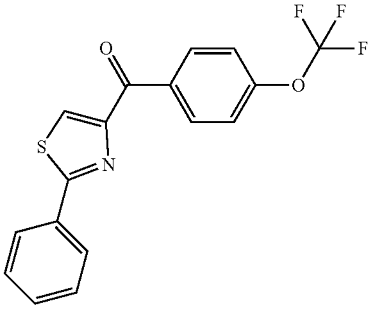 [SMILES: O=C(c1ccc(OC(F)(F)F)cc1)c1csc(-c2ccccc2)n1] |
| 14 | 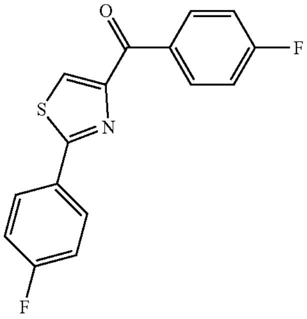 [SMILES: O=C(c1ccc(F)cc1)c1csc(-c2ccc(F)cc2)n1] |
| 16 | 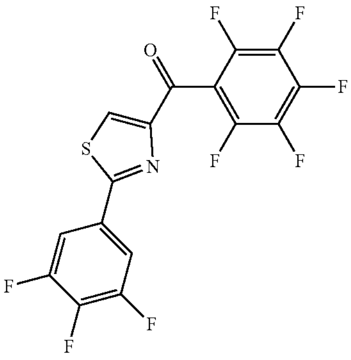 [SMILES: O=C(c1csc(-c2cc(F)c(F)c(F)c2)n1)c1c(F)c(F)c(F)c(F)c1F] |
| 17 | 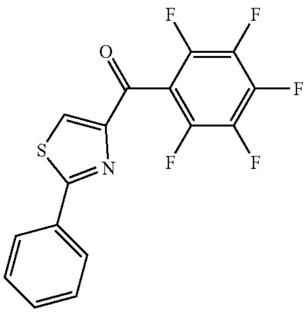 [SMILES: O=C(c1csc(-c2ccccc2)n1)c1c(F)c(F)c(F)c(F)c1F] |

TABLE 1B-continued
| compound | Structure |
|---|---|
| 18 | 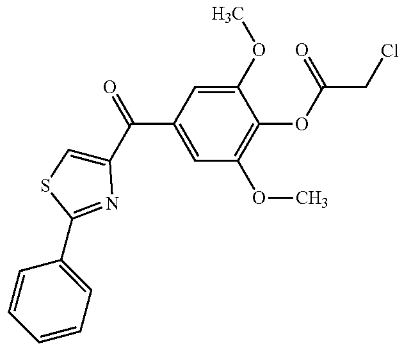 [SMILES: COc1cc(C(=O)c2csc(-c3ccccc3)n2)cc(OC)c1OC(=O)CCl] |
| 19 | 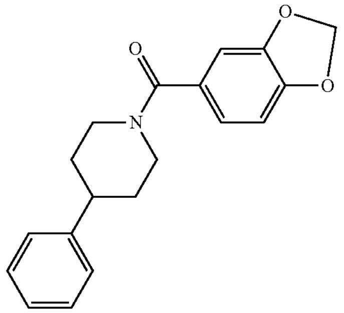 [SMILES: O=C(c1ccc2c(c1)OCO2)N1CCC(c2ccccc2)CC1] |
| 20 | 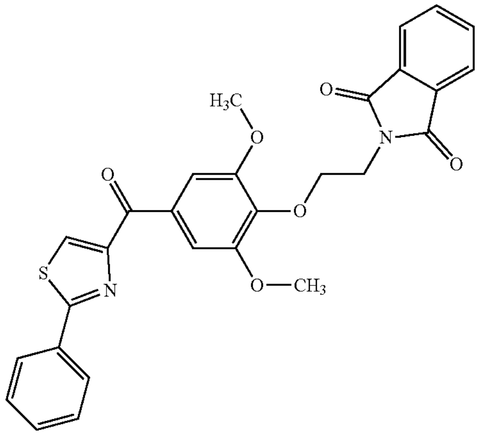 [SMILES: COc1cc(C(=O)c2csc(-c3ccccc3)n2)cc(OC)c1OCCN1C(=O)c2ccccc2C1=O] |
| 21 | 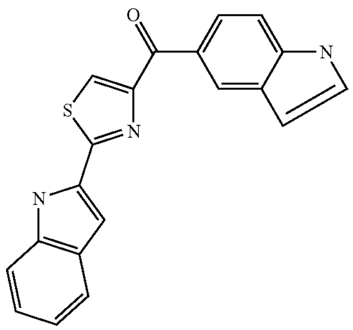 [SMILES: O=C(c1ccc2[nH]ccc2c1)c1csc(-c2cc3ccccc3[nH]2)n1] |
TABLE 1B-continued
| compound | Structure |
|---|---|
| 22 | 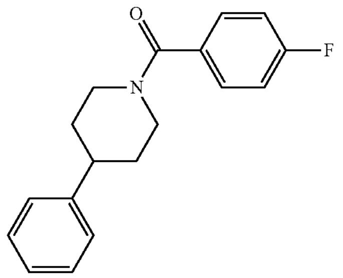 [SMILES: O=C(c1ccc(F)cc1)N1CCC(c2ccccc2)CC1] |
| 23 | 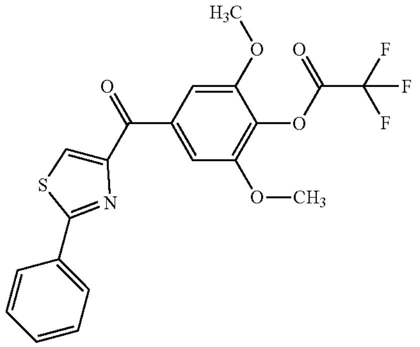 [SMILES: COc1cc(C(=O)c2csc(-c3ccccc3)n2)cc(OC)c1OC(=O)C(F)(F)F] |
| 24 | 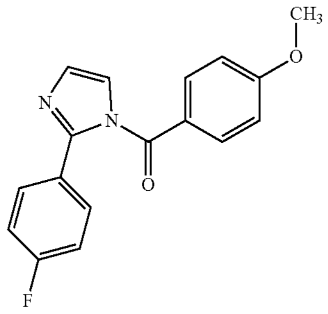 [SMILES: COc1ccc(C(=O)n2ccnc2-c2ccc(F)cc2)cc1] |
| 25 | 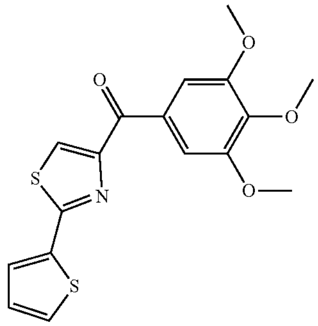 [SMILES: COc1cc(C(=O)c2csc(-c3cccs3)n2)cc(OC)c1OC] |
| 26 | 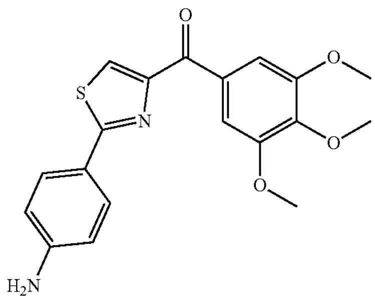 [SMILES: COc1cc(C(=O)c2csc(-c3ccc(N)cc3)n2)cc(OC)c1OC] |

TABLE 1B-continued
| compound | Structure |
|---|---|
| 27 | 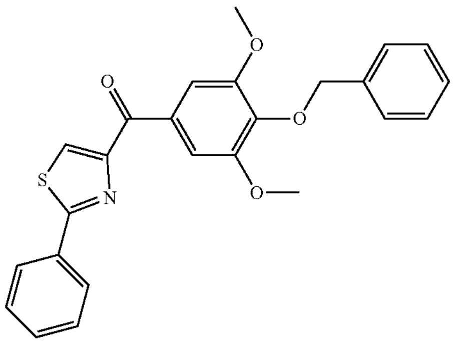 [SMILES: COc1cc(C(=O)c2csc(-c3ccccc3)n2)cc(OC)c1OCc1ccccc1] |
| 28 | 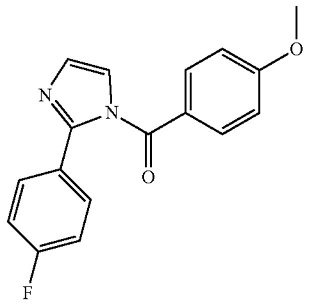 [SMILES: COc1ccc(C(=O)n2ccnc2-c2ccc(F)cc2)cc1] |
| 29 | 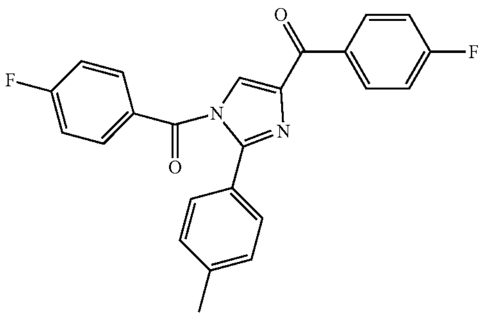 [SMILES: Cc1ccc(-c2nc(C(=O)c3ccc(F)cc3)cn2C(=O)c2ccc(F)cc2)cc1] |
| 30 | 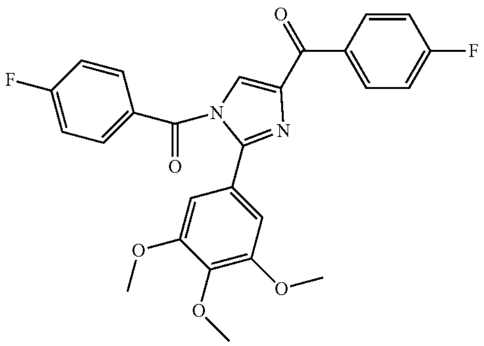 [SMILES: COc1cc(-c2nc(C(=O)c3ccc(F)cc3)cn2C(=O)c2ccc(F)cc2)cc(OC)c1OC] |
TABLE 1B-continued
| compound | Structure |
|---|---|
| 32 | 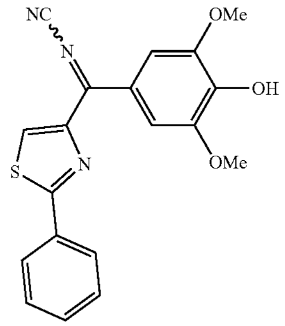 [SMILES: COc1cc(C(=NC#N)c2csc(-c3ccccc3)n2)cc(OC)c1O] |
| 33 | 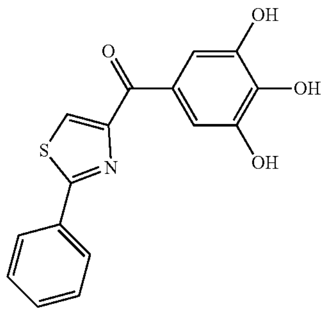 [SMILES: O=C(c1cc(O)c(O)c(O)c1)c1csc(-c2ccccc2)n1] |
| 34 | 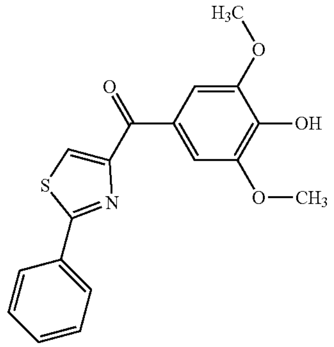 [SMILES: COc1cc(C(=O)c2csc(-c3ccccc3)n2)cc(OC)c1O] |
| 35 | 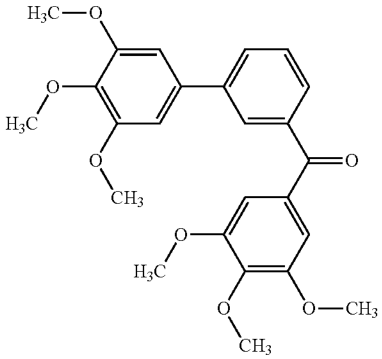 |

TABLE 1B-continued
| compound | Structure |
|---|---|
| 40 | 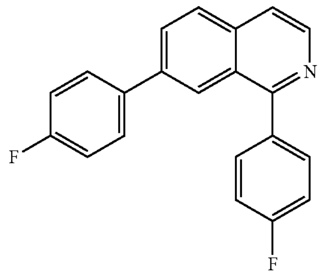 [SMILES: Fc1ccc(-c2ccc3ccnc(-c4ccc(F)cc4)c3c2)cc1] |
| 41 | 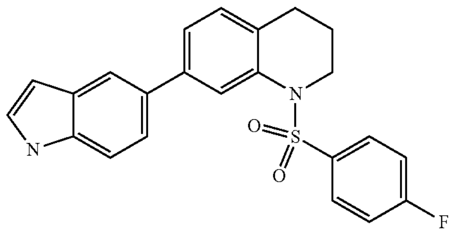 [SMILES: O=S(=O)(c1ccc(F)cc1)N1CCCc2ccc(-c3ccc4[nH]ccc4c3)cc21] |
| 42 | 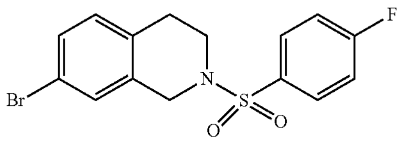 [SMILES: O=S(=O)(c1ccc(F)cc1)N1CCc2ccc(Br)cc2C1] |
| 43 | 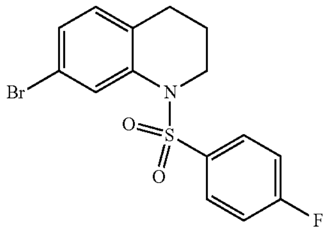 [SMILES: O=S(=O)(c1ccc(F)cc1)N1CCCc2ccc(Br)cc21] |
| 44 | 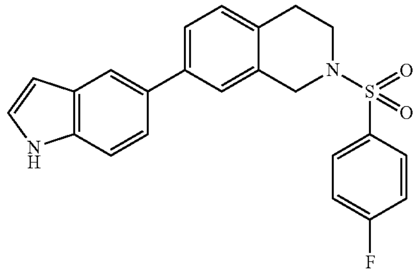 [SMILES: O=S(=O)(c1ccc(F)cc1)N1CCc2ccc(-c3ccc4[nH]ccc4c3)cc2C1] |
| 45 | 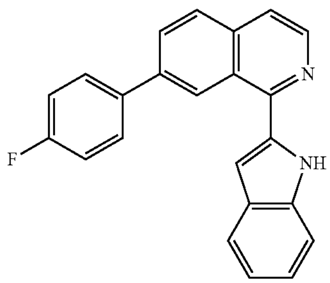 [SMILES: Fc1ccc(-c2ccc3ccnc(-c4cc5ccccc5[nH]4)c3c2)cc1] |
TABLE 1B-continued
| compound | Structure |
|---|---|
| 46 | 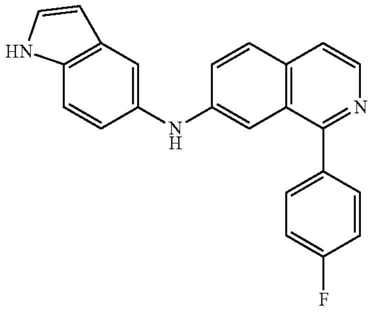 [SMILES: Fc1ccc(-c2nccc3ccc(Nc4ccc5[nH]ccc5c4)cc23)cc1] |
| 47 | 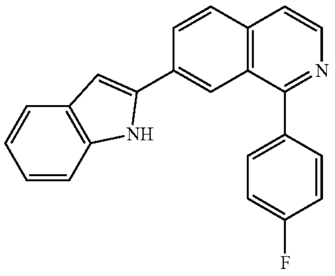 [SMILES: Fc1ccc(-c2nccc3ccc(-c4cc5ccccc5[nH]4)cc23)cc1] |
| 48 | 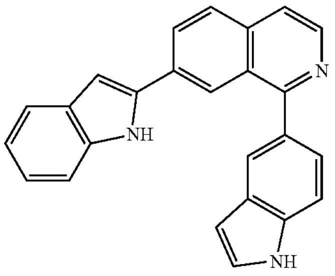 [SMILES: c1ccc2[nH]c(-c3ccc4ccnc(-c5ccc6[nH]ccc6c5)c4c3)cc2c1] |
| 49 | 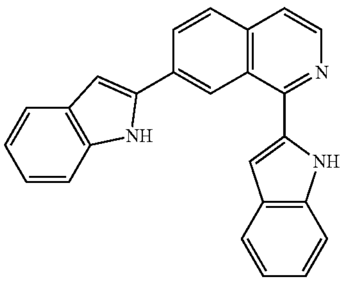 [SMILES: c1ccc2[nH]c(-c3ccc4ccnc(-c5cc6ccccc6[nH]5)c4c3)cc2c1] |
| 50 | 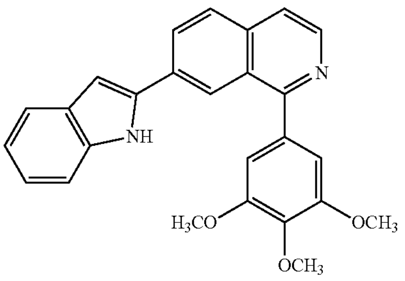 [SMILES: COc1cc(-c2nccc3ccc(-c4cc5ccccc5[nH]4)cc23)cc(OC)c1OC] |

TABLE 1B-continued

| compound | Structure |
|---|---|
| 51 | 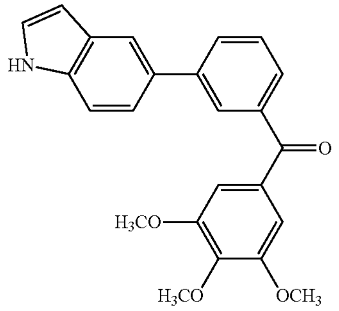 [SMILES: COc1cc(C(=O)c2cccc(-c3ccc4[nH]ccc4c3)c2)cc(OC)c1OC] |
| 52 | 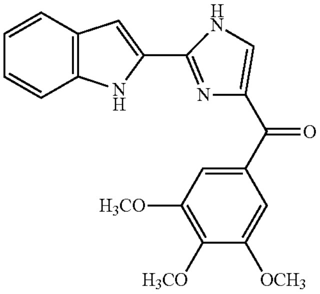 [SMILES: COc1cc(C(=O)c2c[nH]c(-c3cc4ccccc4[nH]3)n2)cc(OC)c1OC] |
| 53 | 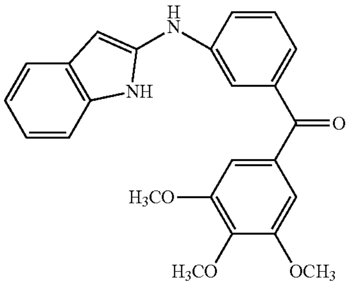 [SMILES: COc1cc(C(=O)c2cccc(Nc3cc4ccccc4[nH]3)c2)cc(OC)c1OC] |
| 54 | 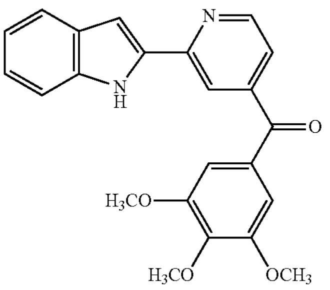 [SMILES: COc1cc(C(=O)c2ccnc(-c3cc4ccccc4[nH]3)c2)cc(OC)c1OC] |

The invention also encompasses methods of treating an Orthomyxoviridae infection in a subject in need thereof by administering to the subject a formulation having a therapeutically effective amount of a compound of the Formula XIII:

(XIII)

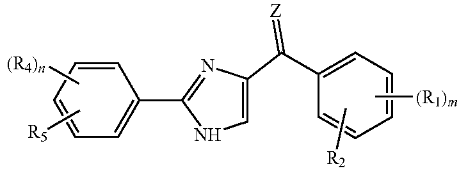

wherein

Z is O;

$R_1$ and $R_4$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_2$ and $R_5$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer.

The invention also encompasses methods of treating an Orthomyxoviridae infection in a subject in need thereof by administering to the subject a formulation having a therapeutically effective amount of a compound of the Formula XIV:

(XIV)

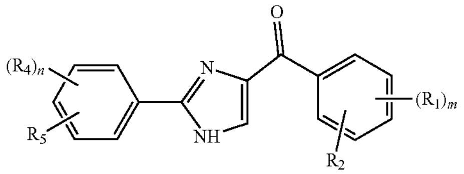

wherein $R_1$ and $R_4$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_2$ and $R_5$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO-alkyl, COOH, —C(O)Ph, C(O)O—$(C_1$-$C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer thereof.

Non limiting examples of compounds of formula XIV are selected from: (2-phenyl-1H-imidazol-4-yl)(3,4,5-trimethoxyphenyl)methanone (12aa), (4-fluorophenyl)(2-phenyl-1H-imidazol-4-yl)methanone (12af), (2-(4-fluorophenyl)-1H-imidazol-4-yl)(3,4,5-trimethoxyphenyl) methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl) methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl) methanone (12dc), (2-(4-chlorophenyl)-1H-imidazol-4-yl) (3,4,5-trimethoxyphenyl)methanone (12fa), (2-(4-chlorophenyl)-1H-imidazol-4-yl)(4-fluorophenyl) methanone (12fb), (2-(4-chlorophenyl)-1H-imidazol-4-yl) (4-hydroxy-3,5-dimethoxyphenyl)methanone (12fc), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(3,4-dimethoxyphenyl)-1H-imidazol-4-yl)(3,4,5-trimethoxyphenyl)methanone (12 ha), (2-(4-(benzyloxy)phenyl)-1H-imidazol-4-yl)(4-fluorophenyl)methanone (12jb), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating an Orthomyxoviridae infection in a subject in need thereof by administering to the subject a formulation having a therapeutically effective amount of a compound of the Formula XIVa:

(XIVa)

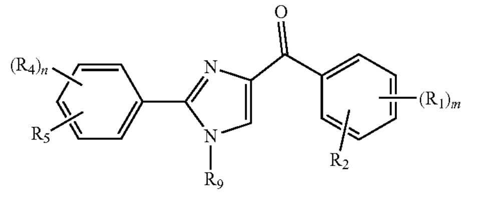

wherein $R_1$ and $R_4$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2$CN, $NH_2$, hydroxyl, OC(O)$CF_3$, —$OCH_2$Ph, —NHCO—$(C_1\text{-}C_4)$alkyl, COOH, —C(O) Ph, C(O)O—$(C_1\text{-}C_4)$alkyl, C(O)H, —C(O)$NH_2$ or $NO_2$;

$R_2$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2$CN, $NH_2$, hydroxyl, OC(O)$CF_3$, —$OCH_2$Ph, —NHCO—$(C_1\text{-}C_4)$alkyl, COOH, —C(O) Ph, C(O)O—$(C_1\text{-}C_4)$alkyl, C(O)H, —C(O)$NH_2$ or $NO_2$;

$R_9$ is H, linear or branched alkyl, aryl, $CH_2$Ph, benzyl, haloalkyl, aminoalkyl, $OCH_2$Ph, $SO_2$-Aryl, —(C═O)-Aryl or OH, optionally substituted with at least one of hydrogen, hydroxyl, an aliphatic straight- or branched-chain $C_1$ to $C_{10}$ hydrocarbon, alkoxy, haloalkoxy, aryloxy, nitro, cyano, alkyl-CN, halo (e.g., F, Cl, Br, I), haloalkyl, dihaloalkyl, trihaloalkyl, COOH, C(O)Ph, C(O)-alkyl, C(O)O-alkyl, C(O)H, C(O)$NH_2$, —OC(O) $CF_3$, $OCH_2$Ph, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof;

m is an integer between 1-4; and n is an integer between 1-4;

or a pharmaceutically acceptable salt, hydrate, polymorph, or isomer thereof.

Non limiting examples of compounds of formula XIVa are selected from: (4-fluorophenyl)(2-phenyl-1-(phenylsulfonyl)-1H-imidazol-4-yl)methanone (11af), (4-fluorophenyl)(2-(4-methoxyphenyl)-1-(phenylsulfonyl)-1H-imidazol-4-yl)methanone (11cb), (4-fluorophenyl)(1-(phenylsulfonyl)-2-(p-tolyl)-1H-imidazol-4-yl)methanone (11db), (2-(4-chlorophenyl)-1-(phenylsulfonyl)-1H-imidazol-4-yl)(4-fluorophenyl)methanone (11fb), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11 ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba), (1-benzyl-2-(p-tolyl)-1H-imidazol-4-yl)(3,4,5-trimethoxyphenyl)methanone (12daa), (1-methyl-2-(p-tolyl)-1H-imidazol-4-yl)(3,4,5-trimethoxyphenyl)methanone (12dab), and (4-fluorophenyl)(2-(4-methoxyphenyl)-1-methyl-1H-imidazol-4-yl)methanone (12cba).

The invention also encompasses methods of treating an Orthomyxoviridae infection in a subject in need thereof by administering to the subject a formulation having a therapeutically effective amount of a compound of the Formula XV:

(XV)

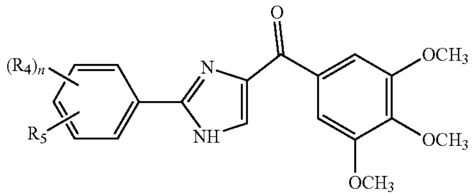

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2$CN, $NH_2$, hydroxyl, OC(O)$CF_3$, —$OCH_2$Ph, —NHCO—$(C_1\text{-}C_4)$alkyl, COOH, —C(O) Ph, C(O)O—$(C_1\text{-}C_4)$alkyl, C(O)H, —C(O)$NH_2$ or $NO_2$; and n is 1-4; or a pharmaceutically acceptable salt, hydrate, polymorph, or isomer thereof.

Non limiting examples of compounds of formula XV are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (3,4,5-trimethoxyphenyl)(2-(3,4,5-trimethoxyphenyl)-1H-imidazol-4-yl)methanone (12ea), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(3,4-dimethoxyphenyl)-1H-imidazol-4-yl)(3,4,5-trimethoxyphenyl)methanone (12 ha), (2-(2-(trifluoromethyl)phenyl)-1H-imidazol- 4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating an Orthomyxoviridae infection in a subject in need thereof by administering to the subject a formulation having a therapeutically effective amount of a compound of the Formula XVI:

(XVI)

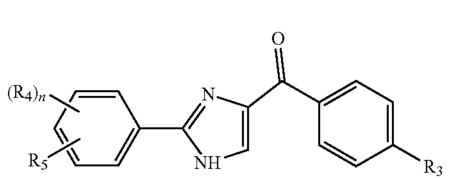

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_3$ is I, Br, Cl, or F; and n is 1-4; or a pharmaceutically acceptable salt, hydrate, polymorph, or isomer.

Non limiting examples of compounds of formula XVI are selected from: (4-fluorophenyl)(2-phenyl-1H-imidazol-4-yl)methanone (12af), (4-fluorophenyl)(2-(4-methoxyphenyl)-1H-imidazol-4-yl)methanone (12cb), (4-fluorophenyl)(2-(p-tolyl)-1H-imidazol-4-yl)methanone (12db), 4-fluorophenyl)(2-(3,4,5-trimethoxyphenyl)-1H-imidazol-4-yl)methanone (12eb), (2-(4-chlorophenyl)-1H-imidazol-4-yl)(4-fluorophenyl)methanone (12fb), (2-(4-(dimethylamino)phenyl)-1H-imidazol-4-yl)(4-fluorophenyl)methanone (12gb), and (2-(4-(benzyloxy)phenyl)-1H-imidazol-4-yl)(4-fluorophenyl)methanone (12jb).

The invention also encompasses methods of treating an Orthomyxoviridae infection in a subject in need thereof by administering to the subject a formulation having a therapeutically effective amount of a compound of the Formula XVII:

(XVII)

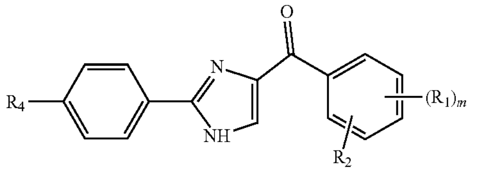

wherein $R_4$ is H, O—$(C_1\text{-}C_4)$alkyl, I, Br, Cl, F, $(C_1\text{-}C_4)$alkyl, halo$(C_1\text{-}C_4)$alkyl, amino$(C_1\text{-}C_4)$alkyl, $OCH_2Ph$, OH, CN, $NO_2$, —NHCO—$(C_1\text{-}C_4)$alkyl, COOH, C(O)O—$(C_1\text{-}C_4)$alkyl or C(O)H;

wherein $R_1$ and $R_2$ are independently H, O-alkyl, I, Br, Cl, F, $(C_1\text{-}C_4)$alkyl, halo$(C_1\text{-}C_4)$alkyl, amino$(C_1\text{-}C_4)$alkyl, $OCH_2Ph$, OH, CN, $NO_2$, —NHCO—$(C_1\text{-}C_4)$alkyl, COOH, C(O)O—$(C_1\text{-}C_4)$alkyl or C(O)H; and m is 1-4; or a pharmaceutically acceptable salt, hydrate, polymorph, or isomer thereof.

Non limiting examples of compounds of formula XVII are selected from: (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(3,4,5-trihydroxyphenyl)methanone (13fa), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating an Orthomyxoviridae infection in a subject in need thereof by administering to the subject a formulation having a therapeutically effective amount of a compound of the Formula XVII represented by the structure of formula 12fb:

(12fb)

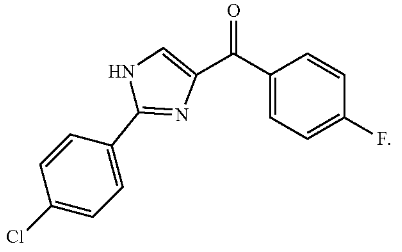

The invention also encompasses methods of treating an Orthomyxoviridae infection in a subject in need thereof by administering to the subject a formulation having a therapeutically effective amount of a compound of the Formula XVII represented by the structure of formula 12cb:

(12cb)

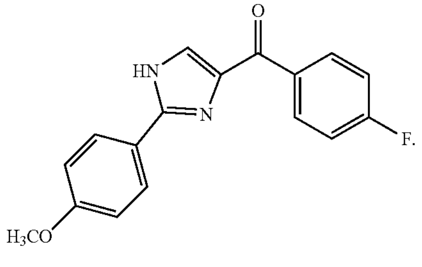

Non limiting examples of compounds are selected from: (4-methoxyphenyl)(2-phenyl-1H-imidazol-1-yl)methanone (12aba), (2-phenyl-1H-imidazol-1-yl)(3,4,5-trimethoxyphenyl)methanone (12aaa), 2-phenyl-1-(phenylsulfonyl)-1H-imidazole (10a), 2-(4-nitrophenyl)-1-(phenylsulfonyl)-1H-imidazole (10x), and 2-(4-(benzyloxy)phenyl)-1-(phenylsulfonyl)-1H-imidazole (10j).

The invention also encompasses methods of treating an Orthomyxoviridae infection in a subject in need thereof by administering to the subject a formulation having a therapeutically effective amount of a compound of the Formula XIX:

(XIX)

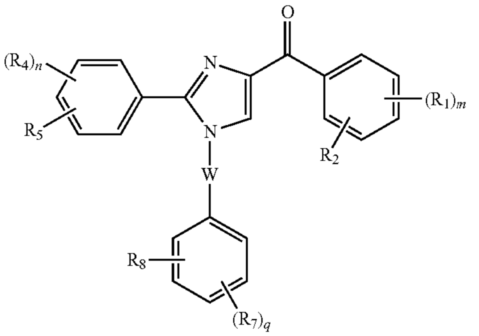

wherein

W is C═O, C═S, $SO_2$, or S═O;

$R_1$, $R_4$ and $R_7$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

$R_2$, $R_5$ and $R_8$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

m is 1-4;

n is 1-4; and q is 1-4;

or its pharmaceutically acceptable salt, hydrate, polymorph, or isomer.

Non limiting examples of compounds of formula XIX are selected from: (2-(4-(dimethylamino)phenyl)-1-((4-methoxyphenyl)sulfonyl)-1H-imidazol-4-yl)(3,4,5-trimethoxyphenyl)methanone (11gaa), (2-(4-bromophenyl)-1-(phenylsulfonyl)-1H-imidazol-4-yl)(3,4,5-trimethoxyphenyl)methanone (11la), (4-fluorophenyl)(2-(4-methoxyphenyl)-1-(phenylsulfonyl)-1H-imidazol-4-yl)methanone (11cb), (2-(4-chlorophenyl)-1-(phenylsulfonyl)-1H-imidazol-4-yl)(4-fluorophenyl)methanone (11fb), (4-fluorophenyl)(2-phenyl-1-(phenylsulfonyl)-1H-imidazol-4-yl)methanone (11af), (4-fluorophenyl)(1-(phenylsulfonyl)-2-(p-tolyl)-1H-imidazol-4-yl)methanone (11db), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11 ha), (2-(4-(benzyloxy)phenyl)-1-(phenylsulfonyl)-1H-imidazol-4-yl)(4-fluorophenyl)methanone (11jb), and (2-(4-(dimethylamino)phenyl)-1-((4-methoxyphenyl)sulfonyl)-1H-imidazol-4-yl)(4-fluorophenyl)methanone (12gba).

The invention also encompasses methods of treating an Orthomyxoviridae infection in a subject in need thereof by administering to the subject a formulation having a therapeutically effective amount of a compound of the Formula XIX represented by the structure of formula 11cb:

(11cb)

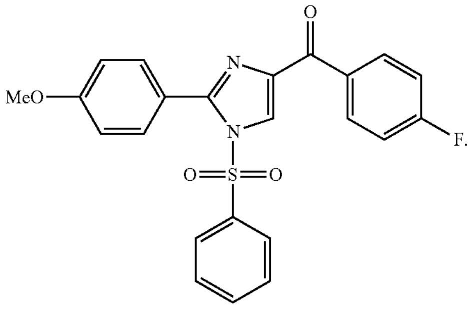

The invention also encompasses methods of treating an Orthomyxoviridae infection in a subject in need thereof by administering to the subject a formulation having a therapeutically effective amount of a compound of the Formula XIX represented by the structure of formula 11fb:

(11fb)

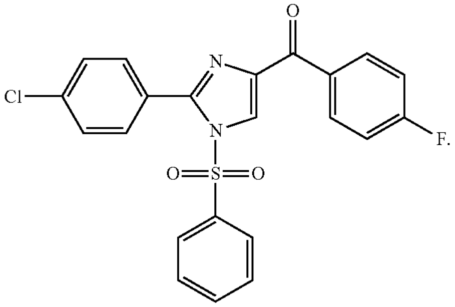

The invention also encompasses methods of treating an Orthomyxoviridae infection in a subject in need thereof by administering to the subject a formulation having a therapeutically effective amount of a compound of the Formula XX:

(XX)

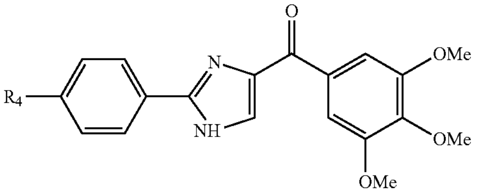

wherein $R_4$ is independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)

O—($C_1$-$C_4$)alkyl, C(O)H, —C(O)$NH_2$ or $NO_2$; or a pharmaceutically acceptable salt, hydrate, polymorph, or isomer.

Non limiting examples of compounds of formula XX are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating an Orthomyxoviridae infection in a subject in need thereof by administering to the subject a formulation having a therapeutically effective amount of a compound of the Formula XX represented by the structure of formula 12da:

(12da)

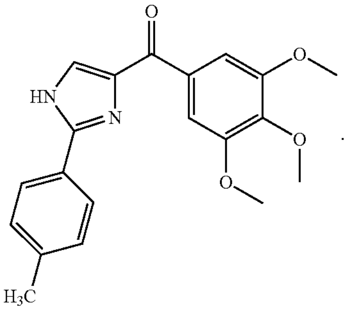

The invention also encompasses methods of treating an Orthomyxoviridae infection in a subject in need thereof by administering to the subject a formulation having a therapeutically effective amount of a compound of the Formula XX represented by the structure of formula 12fa:

(12fa)

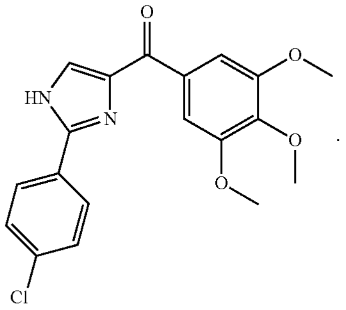

The invention also encompasses methods of treating an Orthomyxoviridae infection in a subject in need thereof by administering to the subject a formulation having a therapeutically effective amount of a compound of the Formula XXI:

(XXI)

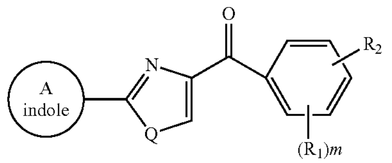

wherein

A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

Q is S or NH;

$R_1$ and $R_2$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and m is 1-4; or a pharmaceutically acceptable salt, hydrate, polymorph, or isomer thereof.

In one embodiment of the method, A ring of compound of formula XXI is substituted 5-indolyl. In another embodiment the substitution is —(C═O)-Aryl. In another embodiment, the aryl is 3,4,5-$(OCH_3)_3$-Ph. In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from: (5-(4-(3,4,5-trimethoxybenzoyl)-1H-imidazol-2-yl)-1H-indol-2-yl)(3,4,5-trimethoxyphenyl)methanone (15xaa); (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (2-(1H-indol-3-yl)-1H-imidazol-4-yl)(3,4,5-trimethoxyphenyl)methanone (17ya); (2-(1H-indol-2-yl)thiazol-4-yl)(3,4,5-trimethoxyphenyl)methanone (62a); and (2-(1H-indol-5-yl)thiazol-4-yl)(3,4,5-trimethoxyphenyl)methanone (66a).

A particularly preferred method of treating an Orthomyxoviridae infection of the invention uses at least one compound of formula XXI including (2-(1H-indol-1-yl)-1H-imidazol-4-yl)(3,4,5-trimethoxyphenyl)methanone; (2-(1H-indol-2-yl)-1H-imidazol-4-yl)(3,4,5-trimethoxyphenyl)methanone; (2-(1H-indol-3-yl)-1H-imidazol-4-yl)(3,4,5-trimethoxyphenyl)methanone (17ya); (2-(1H-indol-4-yl)-1H-imidazol-4-yl)(3,4,5-trimethoxyphenyl)methanone; (2-(1H-indol-5-yl)-1H-imidazol-4-yl)(3,4,5-trimethoxyphenyl)methanone; (2-(1H-indol-6-yl)-1H-imidazol-4-yl)(3,4,5-trimethoxyphenyl)methanone; or (2-(1H-indol-7-yl)-1H-imidazol-4-yl)(3,4,5-trimethoxyphenyl)methanone.

The invention also encompasses methods of treating an Orthomyxoviridae infection in a subject in need thereof by administering to the subject a formulation having a therapeutically effective amount of a compound of the Formula XXIa:

(XXIa)

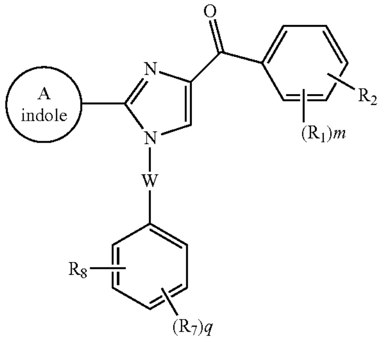

wherein

W is C═O, C═S, $SO_2$, or S═O;

A is indolyl optionally substituted with at least one of $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_1$ and $R_2$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

$R_7$ and $R_8$ are independently hydrogen, $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

m is 1-4; and q is 1-4; or a pharmaceutically acceptable salt, hydrate, polymorph, or isomer thereof.

Non limiting examples of compounds of formula XXIa are selected from: (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); and (1-(phenylsulfonyl)-2-(1-(phenylsulfonyl)-1H-indol-3-yl)-1H-imidazol-4-yl)(3,4,5-trimethoxyphenyl)methanone (17yaa).

The invention also encompasses methods of treating an Orthomyxoviridae infection in a subject in need thereof by administering to the subject a formulation having a therapeutically effective amount of a compound of the Formula XXII:

(XXII)

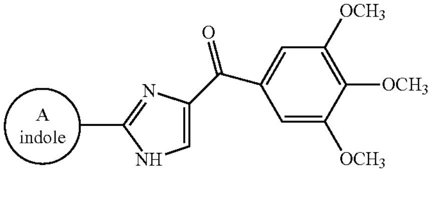

wherein

A is indolyl optionally substituted with at least one of $(C_1$-$C_4)$alkyl, halo$(C_1$-$C_4)$alkyl, O—$(C_1$-$C_4)$alkyl, O—$(C_1$-$C_4)$haloalkyl, $(C_1$-$C_4)$alkylamino, amino$(C_1$-$C_4)$alkyl, F, Cl, Br, I, CN, —$CH_2CN$, $NH_2$, hydroxyl, $OC(O)CF_3$, —$OCH_2Ph$, —NHCO—$(C_1$-$C_4)$alkyl, COOH, —C(O)Ph, C(O)O—$(C_1$-$C_4)$alkyl, C(O)H, —$C(O)NH_2$ or $NO_2$;

or a pharmaceutically acceptable salt, hydrate, polymorph, or isomer thereof.

In one embodiment of the method, A ring of compound of formula XXII is substituted 5-indolyl. In another embodiment the substitution is —(C═O)-Aryl. In another embodiment, the aryl is 3,4,5-$(OCH_3)_3$-Ph. In another embodiment, A ring of compound of formula XXII is 3-indolyl. Non limiting examples of compounds of formula XXII are selected from: (5-(4-(3,4,5-trimethoxybenzoyl)-1H-imidazol-2-yl)-1H-indol-2-yl)(3,4,5-trimethoxyphenyl)methanone (15xaa); and (2-(1H-indol-3-yl)-1H-imidazol-4-yl)(3,4,5-trimethoxyphenyl)methanone (17ya).

The invention also encompasses methods of treating an Orthomyxoviridae infection in a subject in need thereof by administering to the subject a formulation having a therapeutically effective amount of a compound of the Formula XXI or XXII represented by the structure of formula 17ya:

(17ya)

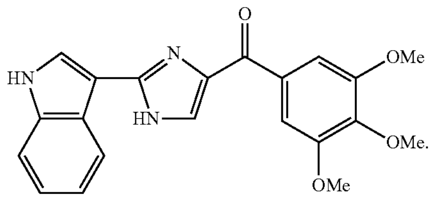

In one embodiment of the method, $R_4$ and $R_5$ of compounds of formula XIII-XVI are hydrogens. Non-limiting examples of compounds of formula XIII-XVI wherein $R_4$ and $R_5$ are hydrogens are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); and (2-phenyl-1H-imidazol-4-yl)(m-tolyl)methanone (12ai).

In other embodiments of the invention, the invention encompasses methods of treating Orthomyxoviridae infections wherein said Orthomyxoviridae infection is caused by an influenza virus. In another embodiment, the influenza virus is influenza A. In one of these embodiments, the influenza A virus has the serotype H1N1. In one of these embodiments, the influenza A virus has the serotype H2N2. In one of these embodiments, the influenza A virus has the serotype H3N2. In one of these embodiments, the influenza A virus has the serotype H5N1. In one of these embodiments, the influenza A virus has the serotype H7N7. In one of these embodiments, the influenza A virus has the serotype H1N2 that infects pigs and humans. In others of these embodiments, the influenza A virus has at least one of the serotypes of H9N2, H7N2, H7N3, H10N7, or others as known by the skilled artisan.

In another embodiment, the influenza virus is influenza B. In some embodiments, the influenza B viruses are further classified into one of two lineages: B/Yamagata and B/Victoria. In one of these embodiments, the influenza B virus is classified as lineage B/Yamagata. In one of these embodiments, the influenza B virus is classified as lineage B/Victoria. In another embodiment, the influenza virus is influenza D. In another embodiment, the influenza virus is influenza C.

A further embodiment of the invention encompasses methods of treating a subject with an influenza infection at risk for influenza complications. In some embodiments, subjects at risk for influenza complications include unvaccinated infants aged 12-24 months, persons with chronic pulmonary diseases such as asthma, cystic fibrosis, or chronic obstructive pulmonary disease, persons with hemodynamically significant cardiac disease, persons with vascular disease such as sickle-cell anemia, persons with immunosuppressive disorders, persons with chronic renal dysfunction or cancer, persons with neuromuscular disorders, seizure disorders or cognitive dysfunction which may compromise handling of respiratory secretions, adults >65 years old, or residents of long-term care institutions. Another embodiment of the invention encompasses methods wherein treating a subject with influenza infection reduces mortality. Another embodiment of the invention encompasses methods wherein treating a subject with influenza infection at risk for complications reduces mortality. Another embodiment of the invention encompasses methods wherein treating a subject with influenza infection reduces morbidity. In another embodiments, the influenza complication is pneumonia. Another embodiment of the invention encompasses methods wherein treating a subject with influenza infection at risk for pneumonia reduces morbidity. Another embodiment of the invention encompasses methods wherein treating a subject with influenza infection reduces risk of developing pneumonia. Another embodiment of the invention encompasses methods of treating a subject with influenza infection with viral pneumonia. Another embodiment of the invention encompasses methods wherein treating a subject with influenza infection reduces complication risk or mortality in subjects >65 years of age.

Yet another embodiment of the invention, the methods further comprise at least one additional therapy. An embodiment of the method further comprises a second antiviral therapy such as a neuraminidase inhibitor, an M2 inhibitor, a PA inhibitor, oseltamivir (Tamiflu), zanamivir (Relenza), laninamivir (Inavir), peramivir, rimantadine, amantadine, baloxavir marboxil (Xofluza), ribavirin, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. An embodiment of the method further comprises an additional therapy such as an NAI or PA inhibitor, and/or dexamethasone or other corticosteroids. Yet another embodiment of the methods includes a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

The invention encompasses methods of treating a Poxviridae infection in a subject in need thereof by administering to the subject a formulation having a therapeutically effective amount of a compound of Formula (I):

(I)

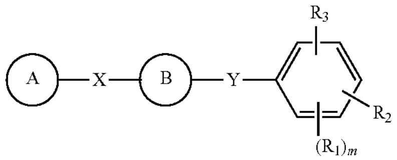

wherein

A is phenyl, indolyl, or indazolyl, optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

B is an imidazole, thiazole, or benzimidazole, optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond, NH, $(C_1\text{-}C_4)$alkyl, O, or S;

Y is a bond, —C═O, —C═S, $SO_2$, SO or S; and m is 1-3, or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of Formula (II):

II

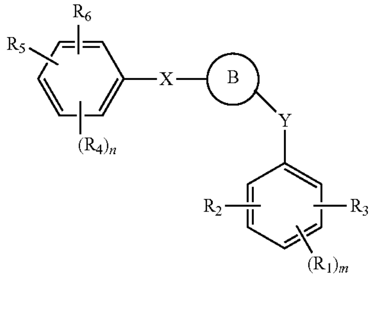

wherein

B is an imidazole, thiazole, or benzimidazole, optionally independently substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, F, Cl, Br, I, CN, —$CH_2CN$, hydroxyl, or $NO_2$;

$R_1$, $R_2$, $R_3$, $R_4$, $R_5$ and $R_6$ are independently at least one of hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, $—OCH_2Ph$, $—NHCO—(C_1\text{-}C_4)$alkyl, COOH, —C(O)Ph, $C(O)O—(C_1\text{-}C_4)$alkyl, C(O)H, $—C(O)NH_2$ or $NO_2$;

X is a bond, NH, or $(C_1\text{-}C_4)$alkyl;

Y is a bond or —C═O;

n is 1-3; and m is 1-3; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of Formula (III):

(III)

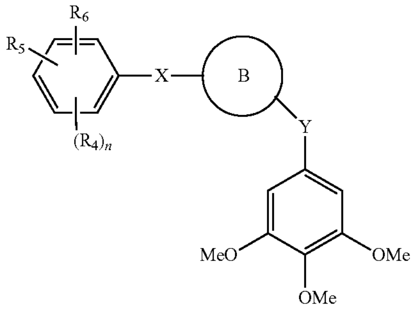

wherein

B is an imidazole, thiazole or benzimidazole, optionally independently substituted with at least one of $(C_1\text{-}C_4)$alkyl, halo$(C_1\text{-}C_4)$alkyl, $O—(C_1\text{-}C_4)$alkyl, O-halo$(C_1\text{-}C_4)$alkyl, F, Cl, Br, I, CN, $—CH_2CN$, hydroxyl, or $NO_2$;

$R_4$, $R_5$ and $R_6$ are independently at least one of hydrogen, $(C_1\text{-}C_4)$alkyl, halo$(C_1\text{-}C_4)$alkyl, $O—(C_1\text{-}C_4)$alkyl, $O—(C_1\text{-}C_4)$haloalkyl, $(C_1\text{-}C_4)$alkylamino, amino$(C_1\text{-}C_4)$alkyl, F, Cl, Br, I, CN, $—CH_2CN$, $NH_2$, hydroxyl, $OC(O)CF_3$, $—OCH_2Ph$, $—NHCO—(C_1\text{-}C_4)$alkyl, COOH, —C(O)Ph, $C(O)O—(C_1\text{-}C_4)$alkyl, C(O)H, $—C(O)NH_2$ or $NO_2$;

X is a bond or NH;

Y is —C═O; and n is 1-3; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of Formula (IV):

(IV)

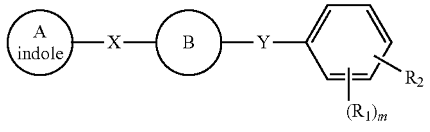

wherein ring A is an indolyl, optionally substituted with at least one of $(C_1\text{-}C_4)$alkyl, halo$(C_1\text{-}C_4)$alkyl, $O—(C_1\text{-}C_4)$alkyl, $O—(C_1\text{-}C_4)$haloalkyl, $(C_1\text{-}C_4)$alkylamino, amino$(C_1\text{-}C_4)$alkyl, F, Cl, Br, I, CN, $—CH_2CN$, $NH_2$, hydroxyl, $OC(O)CF_3$, $—OCH_2Ph$, $—NHCO—(C_1\text{-}C_4)$alkyl, COOH, —C(O)Ph, $C(O)O—(C_1\text{-}C_4)$alkyl, C(O)H, $—C(O)NH_2$ or $NO_2$;

B is an imidazole or benzimidazole, optionally independently substituted with at least one of $(C_1\text{-}C_4)$alkyl, halo$(C_1\text{-}C_4)$alkyl, $O—(C_1\text{-}C_4)$alkyl, O-halo$(C_1\text{-}C_4)$alkyl, F, Cl, Br, I, CN, $—CH_2CN$, hydroxyl, or $NO_2$;

$R_1$ and $R_2$ are independently at least one of hydrogen, $(C_1\text{-}C_4)$alkyl, halo$(C_1\text{-}C_4)$alkyl, $O—(C_1\text{-}C_4)$alkyl, $O—(C_1\text{-}C_4)$haloalkyl, $(C_1\text{-}C_4)$alkylamino, amino$(C_1\text{-}C_4)$alkyl, F, Cl, Br, I, CN, $—CH_2CN$, $NH_2$, hydroxyl, $OC(O)CF_3$, $—OCH_2Ph$, $—NHCO—(C_1\text{-}C_4)$alkyl, COOH, —C(O)Ph, $C(O)O—(C_1\text{-}C_4)$alkyl, C(O)H, $—C(O)NH_2$ or $NO_2$;

X is a bond or NH;

Y is a bond or —C═O; and m is 1-4; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of Formula IV(a):

IV(a)

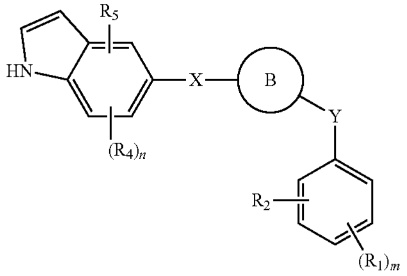

B is an imidazole or benzimidazole, optionally independently substituted with at least one of $(C_1\text{-}C_4)$alkyl, halo$(C_1\text{-}C_4)$alkyl, $O—(C_1\text{-}C_4)$alkyl, O-halo$(C_1\text{-}C_4)$alkyl, F, Cl, Br, I, CN, $—CH_2CN$, hydroxyl, or $NO_2$;

$R_1$, $R_2$, $R_4$ and $R_5$ are independently hydrogen, $(C_1\text{-}C_4)$alkyl, halo$(C_1\text{-}C_4)$alkyl, $O—(C_1\text{-}C_4)$alkyl, $O—(C_1\text{-}C_4)$haloalkyl, $(C_1\text{-}C_4)$alkylamino, amino$(C_1\text{-}C_4)$alkyl, F, Cl, Br, I, CN, $—CH_2CN$, $NH_2$, hydroxyl, $OC(O)CF_3$, $—OCH_2Ph$, $—NHCO—(C_1\text{-}C_4)$alkyl, COOH, —C(O)Ph, $C(O)O—(C_1\text{-}C_4)$alkyl, C(O)H, $—C(O)NH_2$ or $NO_2$; and X is a bond or NH;

Y is a bond or —C═O;

n is 1-2; and m is 1-4; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of Formula (V):

(V)

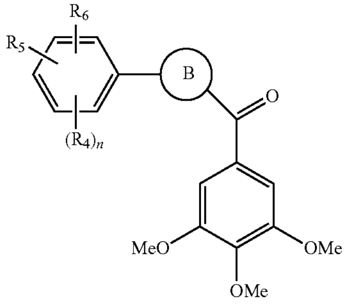

wherein

B is an imidazole or benzimidazole, optionally independently substituted with at least one of ($C_1$-$C_4$)alkyl, halo($C_1$-$C_4$)alkyl, O—($C_1$-$C_4$)alkyl, O-halo($C_1$-$C_4$)alkyl, F, Cl, Br, I, CN, —$CH_2$CN, hydroxyl, or $NO_2$;

$R_4$, $R_5$ and $R_6$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

n is 1-3; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of the Formula (VI):

(VI)

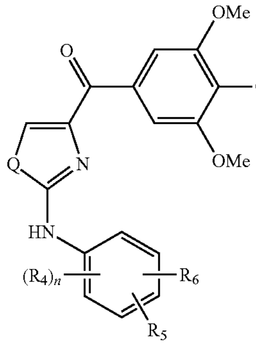

wherein $R_4$, $R_5$ and $R_6$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

Q is S or NH; and n is 1-3; or a pharmaceutically acceptable salt, hydrate, polymorph, or isomer thereof.

Preferably, the variables for the compounds of Formula (VI) are $R_4$, $R_5$ and $R_6$ are independently hydrogen, ($C_1$-$C_4$)alkyl, halo($C_1$-$C_4$)alkyl, O—($C_1$-$C_4$)alkyl, O($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; Q is S or NH; and n is 1-3; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of the Formula VI in the following Table 1A:

TABLE 1A

| Formula VI | Compound | $R_4$ | $R_5$ | $R_6$ | Q |
|---|---|---|---|---|---|
| 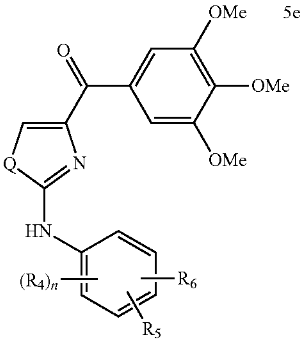 | 5e | H n = 1 | H | H | N |

The invention also encompasses methods of treating a Poxviridae infection in a subject in need thereof by administering to the subject a formulation having a therapeutically effective amount of a compound of the Formula VII:

(VII)

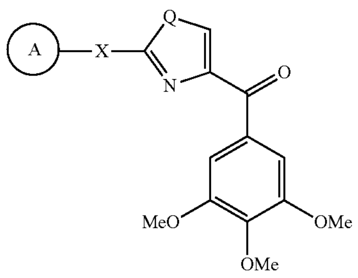

wherein

X is a bond, NH or S;

Q is S or NH; and

A is a phenyl, indolyl, or indazolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

Examples of compounds of Formula VII include, but are not limited to, (2-(phenylamino)-1H-imidazol-4-yl)(3,4,5-trimethoxyphenyl)methanone (5e), (2-(phenylamino)-1H-imidazol-4-yl)(3,4,5-trimethoxyphenyl)methanone hydrochloride salt (5He), and (2-(1H-indol-3-yl)-1H-imidazol-4-yl)(3,4,5-trimethoxyphenyl)methanone (17ya).

Preferably, the variables in the compounds of Formula VII are X is a bond; Q is NH; and A is an indolyl ring optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of the Formula VII(a):

VII(a)

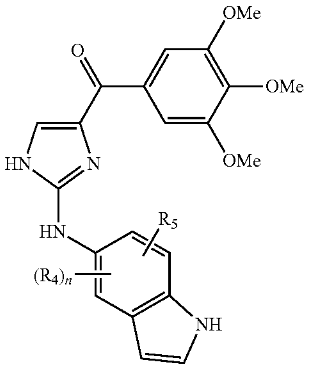

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of the Formula VII(b):

VII(b)

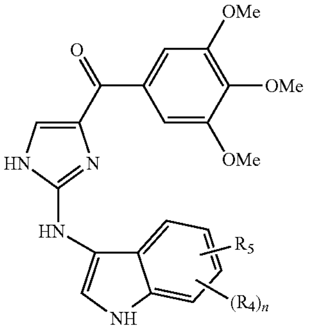

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

The invention also encompasses methods of treating a Poxviridae infection in a subject in need thereof by administering to the subject a formulation having a therapeutically effective amount of a compound of the Formula VII(c):

VII(c)

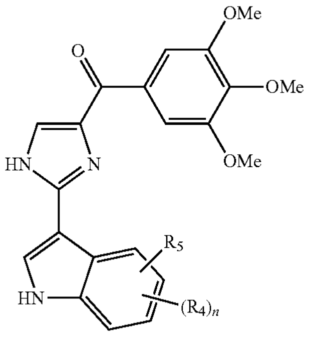

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof. Examples of compounds of Formula VII(c) include, but are not limited to, (2-(1H-indol-3-yl)-1H-imidazol-4-yl)(3,4,5-trimethoxyphenyl)methanone (17ya).

The invention also encompasses methods of treating a Poxviridae infection in a subject in need thereof by administering to the subject a formulation having a therapeutically effective amount of a compound of the Formula VII(c):

VII(c)

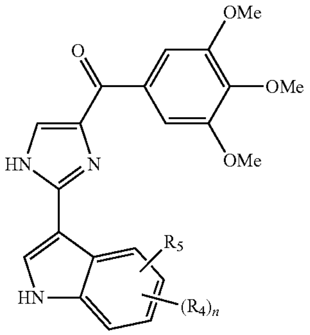

wherein $R_4$ and $R_5$ are independently hydrogen, $(C_1\text{-}C_4)$ alkyl, halo$(C_1\text{-}C_4)$alkyl, O—$(C_1\text{-}C_4)$alkyl, O—$(C_1\text{-}C_4)$ haloalkyl, F, Cl, Br, I, and CN; and n is 1-4; or a pharmaceutically acceptable salt, hydrate, polymorph, or isomer thereof. Examples of compounds of Formula VII(c) include, but are not limited to, (2-(1H-indol-3-yl)-1H-imidazol-4-yl)(3,4,5-trimethoxyphenyl)methanone (17ya).

The invention also encompasses methods of treating a Poxviridae infection in a subject in need thereof by administering to the subject a formulation having a therapeutically effective amount of a compound of the Formula 17ya:

(17ya)

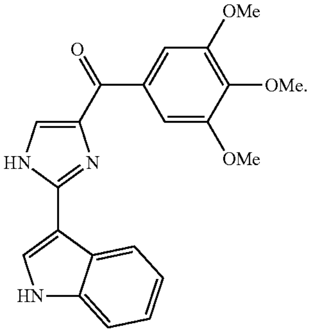

The invention also encompasses methods of treating a Poxviridae infection in a subject in need thereof by administering to the subject a formulation having a therapeutically effective amount of a compound of the Formula in the Table 1B above:

The invention also encompasses methods of treating a Poxviridae infection in a subject in need thereof by administering to the subject a formulation having a therapeutically effective amount of a compound of the Formula XIII:

(XIII)

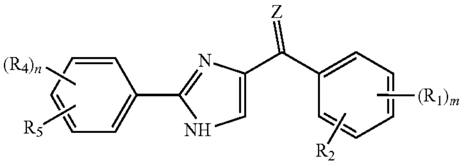

wherein

Z is O;

$R_1$ and $R_4$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_2$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer.

The invention also encompasses methods of treating a Poxviridae infection in a subject in need thereof by administering to the subject a formulation having a therapeutically effective amount of a compound of the Formula XIV:

(XIV)

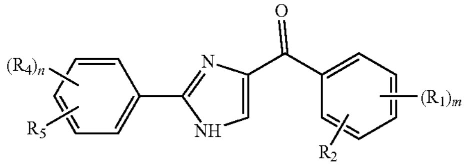

wherein $R_1$ and $R_4$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_2$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO-alkyl, COOH, —C(O)Ph, C(O)O—$(C_1\text{-}C_4)$alkyl, C(O)H, —$C(O)NH_2$ or $NO_2$;

m is an integer between 1-4; and n is an integer between 1-4;

or a pharmaceutically acceptable salt, hydrate, polymorph, or isomer thereof.

Non limiting examples of compounds of formula XIV are selected from: (2-phenyl-1H-imidazol-4-yl)(3,4,5-trimethoxyphenyl)methanone (12aa), (4-fluorophenyl)(2-phenyl-1H-imidazol-4-yl)methanone (12af), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(4-hydroxy-3,5-dimethoxyphenyl)methanone (12fc), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(3,4-dimethoxyphenyl)-1H-imidazol-4-yl)(3,4,5-trimethoxyphenyl)methanone (12 ha), (2-(4-(benzyloxy)phenyl)-1H-imidazol-4-yl)(4-fluorophenyl)methanone (12jb), (2-(4-bromophenyl)-1H-imidazol-4-yl)(3,4,5-trimethoxyphenyl)methanone (12la), and (2-(4-(trifluoromethyl)phenyl)-1H-imidazol-4-yl)(3,4,5-trimethoxyphenyl)methanone (12pa).

The invention also encompasses methods of treating a Poxviridae infection in a subject in need thereof by administering to the subject a formulation having a therapeutically effective amount of a compound of the Formula XIVa:

(XIVa)

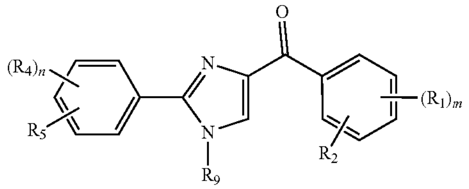

wherein $R_1$ and $R_4$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_2$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_9$ is H, linear or branched alkyl, aryl, $CH_2Ph$, benzyl, haloalkyl, aminoalkyl, $OCH_2Ph$, $SO_2$-Aryl, —(C═O)-Aryl or OH, optionally substituted with at least one of hydrogen, hydroxyl, an aliphatic straight- or branched-chain $C_1$ to $C_{10}$ hydrocarbon, alkoxy, haloalkoxy, aryloxy, nitro, cyano, alkyl-CN, halo (e.g., F, Cl, Br, I), haloalkyl, dihaloalkyl, trihaloalkyl, COOH, C(O)Ph, C(O)-alkyl, C(O)O-alkyl, C(O)H, $C(O)NH_2$, —OC(O)$CF_3$, $OCH_2Ph$, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof;

m is an integer between 1-4; and n is an integer between 1-4;

or a pharmaceutically acceptable salt, hydrate, polymorph, or isomer thereof.

Non limiting examples of compounds of formula XIVa are selected from: (4-fluorophenyl)(2-phenyl-1-(phenylsulfonyl)-1H-imidazol-4-yl)methanone (11af), (4-fluorophenyl)(2-(4-methoxyphenyl)-1-(phenylsulfonyl)-1H-imidazol-4-yl)methanone (11cb), (4-fluorophenyl)(1-(phenylsulfonyl)-2-(p-tolyl)-1H-imidazol-4-yl)methanone (11db), (2-(4-chlorophenyl)-1-(phenylsulfonyl)-1H-imidazol-4-yl)(4-fluorophenyl)methanone (11fb), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11 ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba), (1-benzyl-2-(p-tolyl)-1H-imidazol-4-yl)(3,4,5-trimethoxyphenyl)methanone (12daa), (1-methyl-2-(p-tolyl)-1H-imidazol-4-yl)(3,4,5-trimethoxyphenyl)methanone (12dab), and (4-fluorophenyl)(2-(4-methoxyphenyl)-1-methyl-1H-imidazol-4-yl)methanone (12cba).

The invention also encompasses methods of treating a Poxviridae infection in a subject in need thereof by administering to the subject a formulation having a therapeutically effective amount of a compound of the Formula XV:

(XV)

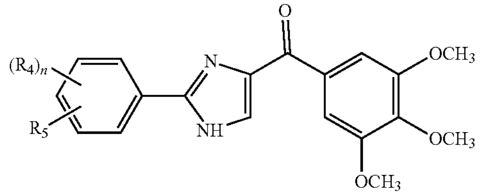

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

Non limiting examples of compounds of formula XV are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (3,4,5-trimethoxyphenyl)(2-(3,4,5-trimethoxyphenyl)-1H-imidazol-4-yl)methanone (12ea), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(3,4-dimethoxyphenyl)-1H-imidazol-4-yl)(3,4,5-trimethoxyphenyl)methanone (12 ha), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating a Poxviridae infection in a subject in need thereof by administering to the subject a formulation having a therapeutically effective amount of a compound of the Formula XVI:

(XVI)

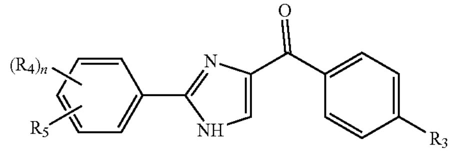

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

$R_3$ is I, Br, Cl, or F; and n is 1-4; or a pharmaceutically acceptable salt, hydrate, polymorph, or isomer.

Non limiting examples of compounds of formula XVI are selected from: (4-fluorophenyl)(2-phenyl-1H-imidazol-4-yl)methanone (12af), (4-fluorophenyl)(2-(4-methoxyphenyl)-1H-imidazol-4-yl)methanone (12cb), (4-fluorophenyl)(2-(p-tolyl)-1H-imidazol-4-yl)methanone (12db), 4-fluorophenyl)(2-(3,4,5-trimethoxyphenyl)-1H-imidazol-4-yl)methanone (12eb), (2-(4-chlorophenyl)-1H-imidazol-4-yl)(4-fluorophenyl)methanone (12fb), (2-(4-(dimethylamino)phenyl)-1H-imidazol-4-yl)(4-fluorophenyl)methanone (12gb), and (2-(4-(benzyloxy)phenyl)-1H-imidazol-4-yl)(4-fluorophenyl)methanone (12jb).

The invention also encompasses methods of treating a Poxviridae infection in a subject in need thereof by administering to the subject a formulation having a therapeutically effective amount of a compound of the Formula XVII:

(XVII)

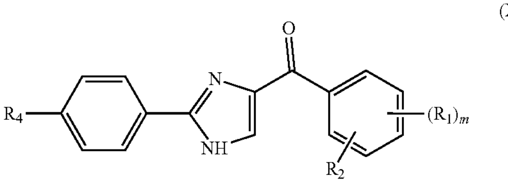

wherein $R_4$ is H, O—($C_1$-$C_4$)alkyl, I, Br, Cl, F, ($C_1$-$C_4$)alkyl, halo($C_1$-$C_4$)alkyl, amino($C_1$-$C_4$)alkyl, $OCH_2Ph$, OH, CN, $NO_2$, —NHCO—($C_1$-$C_4$)alkyl, COOH, C(O)O—($C_1$-$C_4$)alkyl or C(O)H;

wherein $R_1$ and $R_2$ are independently H, O-alkyl, I, Br, Cl, F, ($C_1$-$C_4$)alkyl, halo($C_1$-$C_4$)alkyl, amino($C_1$-$C_4$)alkyl, $OCH_2Ph$, OH, CN, $NO_2$, —NHCO—($C_1$-$C_4$)alkyl, COOH, C(O)O—($C_1$-$C_4$)alkyl or C(O)H; and m is 1-4; or a pharmaceutically acceptable salt, hydrate, polymorph, or isomer thereof.

Non limiting examples of compounds of formula XVII are selected from: (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(3,4,5-trihydroxyphenyl)methanone (13fa), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating a Poxviridae infection in a subject in need thereof by administering to the subject a formulation having a therapeutically effective amount of a compound of the Formula XVII represented by the structure of formula 12fb:

(12fb)

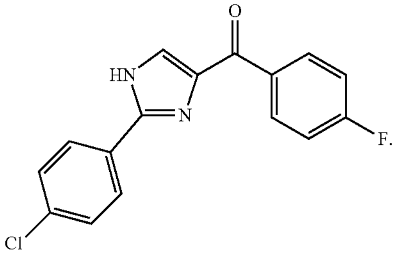

The invention also encompasses methods of treating a Poxviridae infection in a subject in need thereof by administering to the subject a formulation having a therapeutically effective amount of a compound of the Formula XVII represented by the structure of formula 12cb:

(12cb)

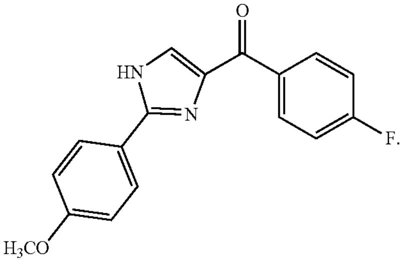

Non limiting examples of compounds are selected from: (4-methoxyphenyl)(2-phenyl-1H-imidazol-1-yl)methanone (12aba), (2-phenyl-1H-imidazol-1-yl)(3,4,5-trimethoxyphenyl)methanone (12aaa), 2-phenyl-1-(phenylsulfonyl)-1H-imidazole (10a), 2-(4-nitrophenyl)-1-(phenylsulfonyl)-1H-imidazole (10x), and 2-(4-(benzyloxy)phenyl)-1-(phenylsulfonyl)-1H-imidazole (10j).

The invention also encompasses methods of treating a Poxviridae infection in a subject in need thereof by administering to the subject a formulation having a therapeutically effective amount of a compound of the Formula XIX:

(XIX)

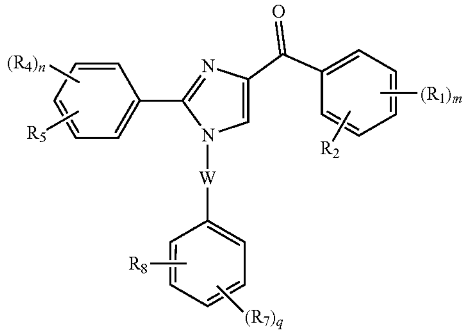

wherein

W is C═O, C═S, $SO_2$, or S═O;

$R_1$, $R_4$ and $R_7$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

$R_2$, $R_5$ and $R_8$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$;

m is 1-4;

n is 1-4; and q is 1-4;

or its pharmaceutically acceptable salt, hydrate, polymorph, or isomer.

Non limiting examples of compounds of formula XIX are selected from: (2-(4-(dimethylamino)phenyl)-1-((4-methoxyphenyl)sulfonyl)-1H-imidazol-4-yl)(3,4,5-trimethoxyphenyl)methanone (11gaa); (2-(4-bromophenyl)-1-(phenylsulfonyl)-1H-imidazol-4-yl)(3,4,5-trimethoxyphenyl)methanone (111a), (4-fluorophenyl)(2-(4-methoxyphenyl)-1-(phenylsulfonyl)-1H-imidazol-4-yl) methanone (11cb), (2-(4-chlorophenyl)-1-(phenylsulfonyl)-1H-imidazol-4-yl)(4-fluorophenyl)methanone (11fb), (4-fluorophenyl)(2-phenyl-1-(phenylsulfonyl)-1H-imidazol-4-yl)methanone (11af), (4-fluorophenyl)(1-(phenylsulfonyl)-2-(p-tolyl)-1H-imidazol-4-yl)methanone (11db), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11 ha), (2-(4-(benzyloxy)phenyl)-1-(phenylsulfonyl)-1H-imidazol-4-yl)(4-fluorophenyl)methanone (11jb), and (2-(4-(dimethylamino)phenyl)-1-((4-methoxyphenyl)sulfonyl)-1H-imidazol-4-yl)(4-fluorophenyl)methanone (12gba).

The invention also encompasses methods of treating a Poxviridae infection in a subject in need thereof by administering to the subject a formulation having a therapeutically effective amount of a compound of the Formula XIX represented by the structure of formula 11cb:

(11cb)

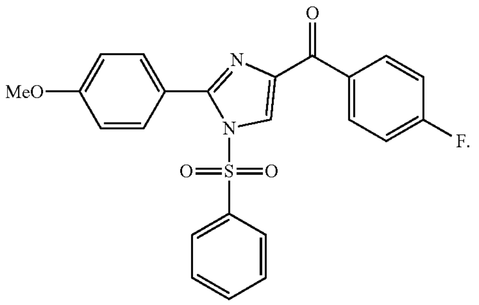

The invention also encompasses methods of treating a Poxviridae infection in a subject in need thereof by administering to the subject a formulation having a therapeutically effective amount of a compound of the Formula XIX represented by the structure of formula 11fb:

(11fb)

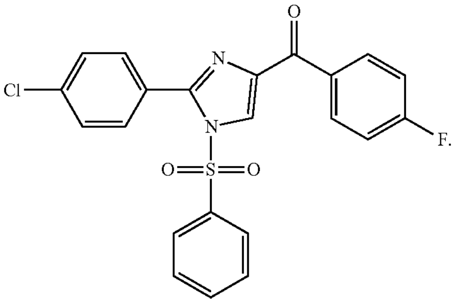

The invention also encompasses methods of treating a Poxviridae infection in a subject in need thereof by administering to the subject a formulation having a therapeutically effective amount of a compound of the Formula XX:

(XX)

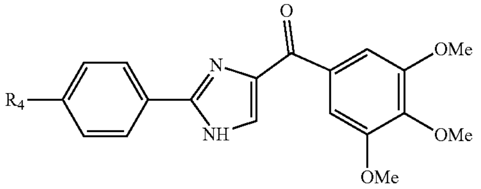

wherein $R_4$ is independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2CN$, $NH_2$, hydroxyl, $OC(O)CF_3$, —$OCH_2Ph$, —NHCO—($C_1$-$C_4$)alkyl, COOH, —C(O)Ph, C(O)O—($C_1$-$C_4$)alkyl, C(O)H, —$C(O)NH_2$ or $NO_2$; or a pharmaceutically acceptable salt, hydrate, polymorph, or isomer.

Non limiting examples of compounds of formula XX are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (121a), and (2-(4-(trifluoromethyl)phenyl)-1H-imidazol-4-yl)(3,4,5-trimethoxyphenyl)methanone (12pa).

The invention also encompasses methods of treating a Poxviridae infection in a subject in need thereof by administering to the subject a formulation having a therapeutically effective amount of a compound of the Formula XX represented by the structure of formula 12da:

(12da)

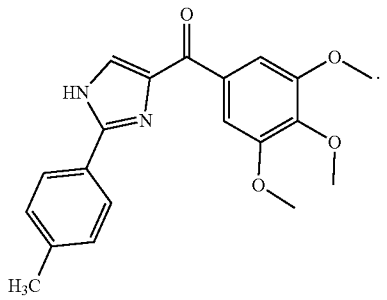

The invention also encompasses methods of treating a Poxviridae infection in a subject in need thereof by administering to the subject a formulation having a therapeutically effective amount of a compound of the Formula XX represented by the structure of formula 12fa:

(12fa)

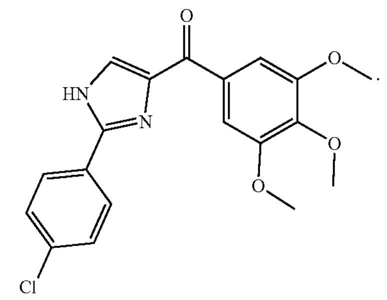

The invention also encompasses methods of treating a Poxviridae infection in a subject in need thereof by administering to the subject a formulation having a therapeutically effective amount of a compound of the Formula XXI:

(XXI)

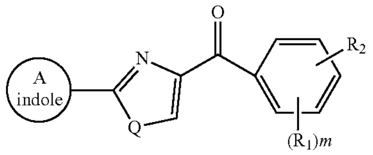

wherein

A is indolyl, optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

Q is S or NH;

$R_1$ and $R_2$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$; and m is 1-4; or a pharmaceutically acceptable salt, hydrate, polymorph, or isomer thereof.

In one embodiment of the method, A ring of compound of formula XXI is substituted 5-indolyl. In another embodiment the substitution is —(C═O)-Aryl. In another embodiment, the aryl is 3,4,5-$(OCH_3)_3$-Ph. In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from: (5-(4-(3,4,5-trimethoxybenzoyl)-1H-imidazol-2-yl)-1H-indol-2-yl)(3,4,5-trimethoxyphenyl)methanone (15xaa); (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (2-(1H-indol-3-yl)-1H-imidazol-4-yl)(3,4,5-trimethoxyphenyl)methanone (17ya); (2-(1H-indol-2-yl)thiazol-4-yl)(3,4,5-trimethoxyphenyl)methanone (62a); and (2-(1H-indol-5-yl)thiazol-4-yl)(3,4,5-trimethoxyphenyl)methanone (66a).

A particularly preferred method of treating a Poxviridae infection of the invention uses at least one compound of formula XXI including (2-(1H-indol-1-yl)-1H-imidazol-4-yl)(3,4,5-trimethoxyphenyl)methanone; (2-(1H-indol-2-yl)-1H-imidazol-4-yl)(3,4,5-trimethoxyphenyl)methanone; (2-(1H-indol-3-yl)-1H-imidazol-4-yl)(3,4,5-trimethoxyphenyl)methanone (17ya); (2-(1H-indol-4-yl)-1H-imidazol-4-yl)(3,4,5-trimethoxyphenyl)methanone; (2-(1H-indol-5-yl)-1H-imidazol-4-yl)(3,4,5-trimethoxyphenyl)methanone; (2-(1H-indol-6-yl)-1H-imidazol-4-yl)(3,4,5-trimethoxyphenyl)methanone; or (2-(1H-indol-7-yl)-1H-imidazol-4-yl)(3,4,5-trimethoxyphenyl)methanone.

The invention also encompasses methods of treating a Poxviridae infection in a subject in need thereof by administering to the subject a formulation having a therapeutically effective amount of a compound of the Formula XXIa:

(XXIa)

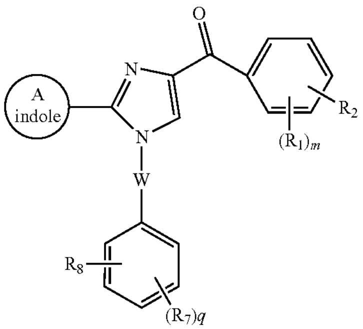

wherein

W is C═O, C═S, $SO_2$, or S═O;

A is indolyl optionally substituted with at least one of ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

$R_1$ and $R_2$ are independently hydrogen, ($C_1$-$C_4$)alkyl, halo($C_1$-$C_4$)alkyl, O—($C_1$-$C_4$)alkyl, O—($C_1$-$C_4$)haloalkyl, ($C_1$-$C_4$)alkylamino, amino($C_1$-$C_4$)alkyl, F, Cl, Br, I, CN, —$CH_2$CN, $NH_2$, hydroxyl, OC(O)$CF_3$, —$OCH_2$Ph, —NHCO—($C_1$-$C_4$)alkyl, COOH, —C(O)Ph, C(O)O—($C_1$-$C_4$)alkyl, C(O)H, —C(O)$NH_2$ or $NO_2$;

$R_7$ and $R_8$ are independently hydrogen, $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

m is 1-4; and q is 1-4; or a pharmaceutically acceptable salt, hydrate, polymorph, or isomer thereof.

Non limiting examples of compounds of formula XXIa are selected from: (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); and (1-(phenylsulfonyl)-2-(1-(phenylsulfonyl)-1H-indol-3-yl)-1H-imidazol-4-yl)(3,4,5-trimethoxyphenyl)methanone (17yaa).

The invention also encompasses methods of treating a Poxviridae infection in a subject in need thereof by administering to the subject a formulation having a therapeutically effective amount of a compound of the Formula XXII:

(XXII)

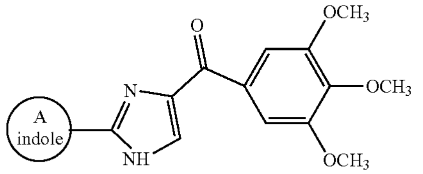

wherein

A is indolyl optionally substituted with at least one of $(C_1\text{-}C_4)$alkyl, halo$(C_1\text{-}C_4)$alkyl, O—$(C_1\text{-}C_4)$alkyl, O—$(C_1\text{-}C_4)$haloalkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

or a pharmaceutically acceptable salt, hydrate, polymorph, or isomer thereof.

In one embodiment of the method, A ring of compound of formula XXII is substituted 5-indolyl. In another embodiment the substitution is —(C═O)-Aryl. In another embodiment, the aryl is 3,4,5-$(OCH_3)_3$-Ph. In another embodiment, A ring of compound of formula XXII is 3-indolyl. Non limiting examples of compounds of formula XXII are selected from: (5-(4-(3,4,5-trimethoxybenzoyl)-1H-imidazol-2-yl)-1H-indol-2-yl)(3,4,5-trimethoxyphenyl)methanone (15xaa); and (2-(1H-indol-3-yl)-1H-imidazol-4-yl)(3,4,5-trimethoxyphenyl)methanone (17ya).

The invention also encompasses methods of treating a Poxviridae infection in a subject in need thereof by administering to the subject a formulation having a therapeutically effective amount of a compound of the Formula XXI or XXII represented by the structure of formula 17ya:

(17ya)

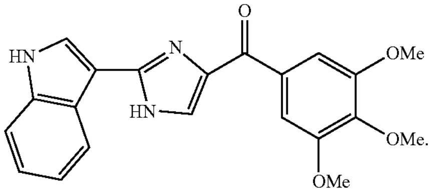

In one embodiment of the method, $R_4$ and $R_5$ of compounds of formula XIII-XVI are hydrogens. Non-limiting examples of compounds of formula XIII-XVI wherein $R_4$ and $R_5$ are hydrogens are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); and (2-phenyl-1H-imidazol-4-yl)(m-tolyl)methanone (12ai).

Yet another embodiment of the invention encompasses methods of treating Poxviridae infections wherein the viral infection is caused by an *Orthopoxvirus*. In one of these embodiments, the *Orthopoxvirus* is smallpox. In one of these embodiments, the *Orthopoxvirus* is Monkeypox. In one of these embodiments, the *Orthopoxvirus* is a vaccinia virus. In one of these embodiments, the *Orthopoxvirus* is any one of coxpox, horsepox, camelpox, Akhmeta virus, and Alaskapox, or other *Orthopoxviruses* as known by the skilled artisan.

A further embodiment of the invention encompasses methods of treating the symptoms of a Poxviridae infection such as encephalitis, severe inflammatory response syndrome, respiratory failure, painful head and neck lymph node swelling, extensive dermal eruption, and septic syndromes.

Yet another embodiment of the invention, the methods further comprise at least one additional therapy. An embodiment of the method further comprises a second antiviral therapy such as a neuraminidase inhibitor, an M2 inhibitor, a PA inhibitor, oseltamivir (Tamiflu), zanamivir (Relenza), laninamivir (Inavir), peramivir, rimantadine, amantadine, baloxavir marboxil (Xofluza), ribavirin, tecovirimat, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. An embodiment of the method further comprises an additional therapy such as tecovirimat. Yet another embodiment of the methods includes a second antiviral therapy that is at least one of tecovirimat, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

An embodiment of the invention encompasses methods wherein the compound of the invention is administered in an amount of about 1 mg to about 100 mg. Another embodiment of the invention encompasses methods wherein the compound of the invention is administered in an amount of about 4 to about 90 mg. Another embodiment of the invention encompasses methods wherein the compound of the invention is administered in an amount of about 9 mg to about 18 mg. Another embodiment of the invention encompasses methods wherein the compound of the invention is administered in an amount of about 4 mg to about 45 mg. In yet another embodiment of the method encompasses at least one pharmaceutically acceptable excipient.

In one embodiment of the method, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). As used herein, the term "substantially pure" refers to stereoisomer is at least about 95% pure in one isomer. Alternatively, the stereoisomer purity may be at least about 98% pure, and more preferably at least about 99% pure.

Compounds can also be in the form of a hydrate, which means that the compound further includes a stoichiometric or non-stoichiometric amount of water bound by non-covalent intermolecular forces.

The invention includes "pharmaceutically acceptable salts" of the compounds used in the method of the invention, which may be produced, by reaction of a compound of this invention with an acid or base. Certain compounds, particularly those possessing acid or basic groups, can also be in the form of a salt, preferably a pharmaceutically acceptable salt. As used herein, the term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds used in the method of the invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

Examples of organic salts of amines include, but are not limited to, aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

Examples of inorganic salts of carboxylic acids or hydroxyls may be selected from ammonium, alkali metals to include lithium, sodium, potassium, cesium; alkaline earth metals to include calcium, magnesium, aluminum; zinc, barium, cholines, quaternary ammoniums.

Examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

Typical salts include, but are not limited to, hydrofluoric, hydrochloric, hydrobromic, hydroiodic, boric, nitric, perchloric, phosphoric, sulfuric, acetate, citrate, maleate, malate, or mesylate. Preferred salts include hydrofluoric, hydrochloric, hydrobromic, hydroiodic, acetate, citrate, maleate, or mesylate. More preferred salts include hydrochloric, acetate, or maleate.

The salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of an existing salt for another ion or suitable ion-exchange resin.

The compounds used in the methods of the invention were synthesized using the methodology described in U.S. Pat. Nos. 8,592,465; 8,822,513; 9,029,408; 9,334,242; 9,447,049; and 10,301,285 and US publication No. 2020/24270, hereby incorporated by reference.

Pharmaceutical Composition

The methods of the invention include the administration of a pharmaceutical composition including a pharmaceutically acceptable carrier and at least one compound described herein. Typically, the pharmaceutical composition may include a compound or its pharmaceutically acceptable salt, and at least one pharmaceutically acceptable excipient. The term "pharmaceutically acceptable excipient" refers to any suitable adjuvants, carriers, excipients, flavorant, or stabilizers, and can be used in pharmaceutical formulations either in solid or liquid form. Such forms include, but are not limited to, tablets, capsules, powders, solutions, suspensions, or emulsions.

The amount of compound used in the method and the dosage regimen for treating a disease condition depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods.

Typically, the formulations have from about 0.01 to about 99 percent by weight of at least one compound by weight, preferably from about 20 to 75 percent of active compound(s), together with the adjuvants, carriers and/or excipients. While individual needs may vary, determination of optimal ranges of effective amounts of each component is within the skill of the art. Typical daily dosages include about 2 mg to about 200 mg or about 1 mg to about 100 mg or about 0.1 mg to about 1000 mg, preferred daily dosages include about 4 mg to about 90 mg, and the most preferred dosages include about 4 mg to about 80 mg of the compound. Other preferred dosages include the antiviral compound in an amount of about 4 mg to about 45 mg, or 9 mg to about 18 mg. Alternatively, a dose is from about 0.01 to 150 mg/kg body weight, preferably from about 1 mg to about 100 mg/kg body weight, and more preferably from about 2 to 50 mg/kg body weight, may be appropriate. The daily dose can be administered in one to four doses per day. Treatment regimen for the administration of the compounds of the present invention can also be determined readily by those with ordinary skill in art. That is, the frequency of administration and size of the dose can be established by routine optimization, preferably while minimizing any side effects.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of a compound, composition or formulation may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The methods may include "additional therapeutic agents" including, but are not limited to, immune therapies (e.g., interferon), therapeutic vaccines, antifibrotic agents, anti-inflammatory agents such as corticosteroids or NSAIDs, bronchodilators such as beta-2 adrenergic agonists and xanthines (e.g., theophylline), mucolytic agents, anti-muscarinics, anti-leukotrienes, inhibitors of cell adhesion (e.g., ICAM antagonists), anti-oxidants (e.g., N-acetylcysteine), cytokine agonists, cytokine antagonists, lung surfactants and/or antimicrobial and anti-viral agents (e.g., ribavirin and amantadine). The methods of the invention may also be used in combination with gene replacement therapy.

The methods of the invention may be administered in conjunction with other antiviral therapies to treat the infection or disease associated with the viral infection, e.g., combination therapy. Suitable antiviral agents contemplated for use in combination with the methods of the invention may include nucleoside and nucleotide reverse transcriptase inhibitors (NRTIs), non-nucleoside reverse transcriptase inhibitors (NNRTIs), protease inhibitors and other antiviral drugs. Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Other antiviral agents include, but are not limited to, neuraminidase inhibitors, hemagglutinin inhibitor, hydroxychloroquine, azithromycin, or medications that modulate the immune system or host cell factors such dexamethasone. Examples include, but are not limited to, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, and valaciclovir. An embodiment of the method further comprises an additional therapy such as a remdesivir and/or dexamethasone. An embodiment of the method further comprises an additional therapy such as casirivimab plus imdevimab. An embodiment of the method further comprises an additional therapy such as bamlanivimab.

The methods of treating Orthomyxoviridae or Poxviridae viral infections may further comprise other therapies. For example, the methods may include a second antiviral therapy such as a neuraminidase inhibitor, remdesivir, hydroxychloroquine, azithromycin, or hemagglutinin inhibitor. Other therapies included in the methods are medications that modulate the immune system or host cell factors such as dexamethasone; corticosteroids; an IL-6 inhibitor such as tocilizumab; interferons; an IL-1 inhibitor; or a kinase inhibitor such as baricitinib. The methods may further comprise an antibody therapy such as high titer COVID-19 convalescent plasma, IVIG, a monoclonal antibody therapy such as casirivimab plus imdevimab, bamlanivimab, or bamlanivimab plus etesevimab. The methods may further comprise tocilizumab or baricitinib. The methods may further comprise an additional therapy such as high titer convalescent plasma; IVIG; casirivimab plus imdevimab; bamlanivimab; or bamlanivimab plus etesevimab. The methods may include a second antiviral therapy that is at least one of favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir. The methods may include a second therapy that is at least one of vitamins C or D, zinc, famotidine, ivermectin, or angiotensin converting enzyme inhibitor (ACEI) or angiotensin receptor binding (ARB) agent.

The solid unit dosage forms can be of the conventional type. The solid form can be a capsule and the like, such as an ordinary gelatin type containing the compounds and a carrier. Carriers include, but are not limited to, lubricants and inert fillers such as, castor oil and similar materials, lactose, sucrose, or cornstarch. The formulations may be tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

The invention can be mixed at cold temperatures, room temperature, or elevated temperatures with a liquid carrier such as a fatty oil, castor oil, or other similar oil to manufacture tablets, capsules, and the like.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the formulation may include excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Typical compositions according to the present invention are prepared so that an oral dosage unit contains between about 1 mg and 100 mg of active compound, and preferred oral compositions contain between 1 mg and 50 mg of active compound.

The formulations may be orally administered with an inert diluent, or with an assimilable edible carrier, or they can be enclosed in hard or soft shell capsules, or they can be compressed into tablets, or they can be incorporated directly with the food of the diet. A preferred formulation is an oral formulation.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions used in the method of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The formulation may also be administered parenterally. Solutions or suspensions of these formulations can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the formulations may be in solution or suspension may be packaged in a pressurized aerosol container together with suitable propellants, for example, hydrocarbon propellants like propane, butane, or isobutane with conventional adjuvants. The formulations also may be administered in a non-pressurized form such as in a nebulizer or atomizer.

When administering the formulations in the methods of the invention, the formulations may be administered systemically or sequentially. Administration can be accomplished in any manner effective for delivering the compounds or the pharmaceutical compositions to the site of viral infection. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

The invention is directed to methods of treating Orthomyxoviridae and Poxviridae viral infections and anti-viral formulations with the compounds and formulations described above. The compounds and formulations thereof have utility in treating Orthomyxoviridae and Poxviridae viral infections by disrupting microtubule polymerization. The formulations may optionally comprise additional active ingredients, whose activity is useful for treating Orthomyxoviridae and Poxviridae viral infections, treat adverse effect associated with the compounds or dosages of a particular formulation, and/or delay or extend the release of the ingredients.

In particular, the methods of the invention may be used to treat infections caused by viruses including those of the superfamilies of Orthomyxoviridae and Poxviridae. Also, the methods of the invention may be used to treat infections caused by viruses including, but not limited to, influenza viruses including influenza A virus (IAV) and influenza B virus (IBV). IAV viruses are known to possess antigenic drift, a mutational process by which IAV presents as having different serotypes which vary from time to time. The serotypes represent antigenically distinct versions of hemagglutinin (H) and neuraminidase (N) viral surface proteins that are important for vaccine preparation and correlated with IAV infectious behavior. Often a particular seasonal epidemic is composed predominantly of one particular serotype or just a few serotypes. Preferably, the methods of the invention treat viral infections caused by HIN1.

The methods of the invention may be used to treat infections caused by Orthomyxoviruses such as the IAV serotypes HIN1, H2N2, H5N1, H3N2, and other seasonal variants from this family of influenza viruses. In one of these embodiments, the influenza A virus has the serotype HIN1. In one of these embodiments, the influenza A virus has the serotype H2N2. In one of these embodiments, the influenza A virus has the serotype H3N2. In one of these embodiments, the influenza A virus has the serotype H5N1. In one of these embodiments, the influenza A virus has the serotype H7N7. In one of these embodiments, the influenza A virus has the serotype H7N9. In one of these embodiments, the influenza A virus has the serotype H1N2. In others of these embodiments, the influenza A virus has at least one of the serotypes of H9N2, H7N2, H7N3, H10N7, or others as known by the skilled artisan.

The method of the invention may also be used to treat infections caused by influenza (flu) viruses including influenza A, influenza B, influenza D, or influenza C. Preferably, the method of the invention may be used to treat influenza B infections. In some embodiments, the influenza B viruses are further classified into one of two lineages: B/Yamagata and B/Victoria. In one of these embodiments, the influenza B virus is classified as lineage B/Yamagata. In one of these embodiments, the influenza B virus is classified as lineage B/Victoria. In another embodiment, the influenza virus is influenza D. In another embodiment, the influenza virus is influenza C.

The methods of the invention may be used to treat subjects with seasonal influenza virus infections. For example, influenza epidemics are typical annual events and occasionally are pandemic in scope. The methods of the invention may further be used to treat subjects with severe influenza virus infections at risk for complications. The methods of the invention may further be used to treat influenza infections complicated by pneumonia.

The methods of the invention may be used to prevent or treat viral pneumonia caused by influenza infections in patients at risk for complications. The methods of the invention may be used to prevent or treat complications of influenza in such high risk influenza patients such as unvaccinated infants aged 12-24 months, persons with chronic pulmonary diseases such as asthma, cystic fibrosis, or chronic obstructive pulmonary disease, persons with hemodynamically significant cardiac disease, persons with vascular disease such as sickle-cell anemia, persons with immunosuppressive disorders, persons with chronic renal dysfunction or cancer, persons with neuromuscular disorders, seizure disorders or cognitive dysfunction which may compromise handling of respiratory secretions, adults >65 years old, or residents of long-term care institutions.

Treatment of the subject with an influenza infection may reduce mortality. The methods of the invention encompass methods wherein treating a subject with influenza infection reduces mortality. The methods of the invention also encompass treating a subject with influenza infection at risk for complications that increases mortality. Another embodiment of the invention encompasses methods wherein treating a subject with influenza infection reduces morbidity. Another embodiment of the invention encompasses methods wherein treating a subject with influenza infection at risk for pneumonia reduces morbidity. Another embodiment of the invention encompasses methods wherein treating a subject with influenza infection reduces risk of developing pneumonia. Another embodiment of the invention encompasses methods wherein treating a subject with influenza infection with risk factors for developing complications of the infection reduces risk of developing pneumonia and mortality. Another embodiment of the invention encompasses methods wherein treating a subject with influenza infection with viral pneumonia. Another embodiment of the invention encompasses methods wherein treating a subject with influenza infection reduces mortality or complication in subjects >65 years of age. Another embodiment of the invention encompasses methods wherein treating a subject with influenza infection reduces mortality or respiratory failure when dosed in combination with influenza standard of care antivirals such as neuraminidase inhibitors, PA inhibitors, amantadine, rimantadine, ribavirin, corticosteroids, and the like. Another embodiment of the invention encompasses methods wherein treating a subject with influenza infection at high risk for acute respiratory distress syndrome (ARDS) or severe acute respiratory syndrome (SARS) reduces mortality or respiratory failure. Another embodiment of the invention encompasses methods wherein treating a subject with influenza infection at high risk for acute respiratory distress syndrome (ARDS) or severe acute respiratory syndrome (SARS) reduces mortality or respiratory failure when dosed in combination with Rapivab (peramivir), Relenza (zanamivir), Tamiflu (oseltamivir phosphate, also available as generic), Xofluza (baloxavir marboxil), amantadine, rimantadine, ribavirin, corticosteroids, and/or antibiotics.

The methods of the invention may be used to treat infections caused by an enveloped double-stranded DNA virus from the Poxviridae family. The methods of the invention may also be used prophylactically to prevent infections in subjects in contact subjects infected with a virus of the Poxviridae family. Preferably, the methods of the invention treat viral infections caused by a virus that belongs to the *Orthopoxvirus* genus of the Poxviridae family. Diseases associated with the *Orthopoxvirus* genus include smallpox, cowpox, horsepox, camelpox, and monkeypox. Preferably, the methods of the invention may be used to treat Monkeypox (Mpox). The methods of the invention may also be used to treat Variola viruses such as smallpox, Vaccinia viruses, or non variola *Orthopoxviruses*.

Methods of the invention can also be used to prevent or treat the symptoms of a Poxviridae infection such as encephalitis, severe inflammatory response syndrome, respiratory failure, painful head and neck lymph node swelling, extensive dermal eruption, and septic syndromes.

Yet another embodiment of the invention, the methods further comprise at least one additional therapy. An embodiment of the method further comprises a second antiviral therapy such as a neuraminidase inhibitor, an M2 inhibitor, a PA inhibitor, oseltamivir (Tamiflu), zanamivir (Relenza), laninamivir (Inavir), peramivir, rimantadine, amantadine, baloxavir marboxil (Xofluza), ribavirin, tecovirimat, remdesivir, hydroxychloroquine, azithromycin, or hemagglutinin inhibitor. An embodiment of the method further comprises medications that modulate the immune system or host cell factors such as dexamethasone or another corticosteroid, an IL-6 inhibitor such as tocilizumab, interferons, an IL-1 inhibitor, or a kinase inhibitor such as baricitinib. An embodiment of the method further comprises an additional therapy such as tecovirimat. Yet another embodiment of the methods includes a second antiviral therapy that is at least one of tecovirimat, favipiravir, lopinavir, ritonavir, remdesivir, janus kinase inhibitors, hydroxychloroquine, azithromycin, amantadine, rimantadine, ribavirin, idoxuridine, trifluridine, vidarabine, acyclovir, ganciclovir, foscarnet, zidovudine, didanosine, peramivir, zalcitabine, stavudine, famciclovir, oseltamivir, zanamivir, or valaciclovir.

The invention encompasses methods for treating Orthomyxoviridae and Poxviridae infections in a subject in need thereof comprising administering to the subject a formulation having a compound described herein or a pharmaceutically acceptable salt, hydrate, polymorph, or isomer thereof in a therapeutically effective amount to treat the viral infection. The methods include at least one of compound 12db, compound 11cb, compound 11fb, compound 12da, compound 12fa, compound 12fb, compound 12cb, compound 55, compound 66a, or compound 17ya. In a particular method, the method includes compound 17ya.

As used herein unless otherwise stated, the term "subject" or "patient" refers to any mammalian patient, including without limitation, humans, other primates, dogs, cats, horses, cows, sheep, pigs, rats, mice, bats, and other rodents. In particular, the subject is a human, and alternatively may be only male or only female.

When administering the compounds and formulations described herein, the formulations can be administered systemically or directly to a specific site where the viral infection is present. Administration may be accomplished in any manner effective for delivering the compounds or the pharmaceutical compositions to the viral infection site. Administration methods include, but are not limited to, oral, topical, transdermal, parenteral, subcutaneous, intravenous, intramuscular, intraperitoneal, intranasal, by intracavitary or intravesical instillation, intraocular, intraarterial, intralesional, or by application to the mucous membrane. Mucous membranes include those found in the nose, throat, and/or bronchial tubes, among others. Preferably, the formulation is administered orally. Administration may be simultaneous or sequential with additional antiviral compounds or formulations, or treatments used to address side effects associated with the compounds or dosages.

The following examples are presented in order to more fully illustrate the preferred embodiments of the invention. They should in no way, however, be construed as limiting the broad scope of the invention.

EXAMPLES

The Examples set forth below are for illustrative purposes only and are not intended to limit, in any way, the scope of the present invention.

Materials and Methods:

In Vitro Tubulin Polymerization Assay. Bovine brain tubulin (0.4 mg, >97% pure) (Cytoskeleton, Denver, CO) was mixed with 10 μM of the test compounds and incubated in 100 μL of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, VT). The spectrophotometer was set at 37° C. for tubulin polymerization. Compounds of the invention have demonstrated tubulin inhibition in this assay and other assays known to the skilled artisan.

Example 1

Compound 17Ya Significantly Reduced Key Cytokines Involved in Acute Respiratory Distress Syndrome (ARDS) in HIN1 Influenza Pulmonary Inflammation Murine ARDS Model An animal study was completed whose purpose was to evaluate the efficacy of Compound 17ya in the influenza H1N1 pulmonary inflammation mouse ARDS model. The details of the materials and methods are reported in Example 2 below, as well results and statistical significance thereof; whereas this abstract adds some further analysis of these results. Two hours before starting treatment, mice were administered H1N1 or saline via the intranasal route to induce a viral infection and inflammatory response in the lung followed by daily treatments with saline, Compound 17ya, dexamethasone (anti-inflammatory control), or oseltamivir (direct antiviral control).

Clinical signs and longitudinal lung function (Penh) were measured, bronchoalveolar lavage (BAL), which is washings from lungs, was collected to determine both amounts of inflammatory cells and levels of cytokines, and histopathologic examination of lungs was performed to evaluate inflammation.

Preclinical Study Results Highlights:

Compound 17ya treatment resulted in a statistically significant decrease in the total number of inflammatory cells (−53%) ($p<0.01$) in BAL fluid, including statistically significant reductions in both the innate and adaptive immune cells. In addition, Compound 17ya treatment showed a statistically significant reduction in key cytokines and chemokines in BAL fluid that are part of the cytokine storm responsible for the acute lung injury: Keratinocyte-derived chemokine (KC) (−38%; $p<0.01$), Interleukin-6 (IL-6) (−74%; $p<0.001$), TNF-α (−36%; $p<0.05$), Interferon-γ (INF-γ) (−84%; $p<0.001$), and CXCL-10 (−60%; $p<0.001$). In contrast, dexamethasone treatment did not demonstrate a statistically significant reduction in the total number of inflammatory cells in the BAL fluid. Dexamethasone also had a different effect from Compound 17ya on cytokine production in the BAL fluid. Dexamethasone treatment resulted in statistically significant reductions for IL-6 (−52%; $p<0.01$) and INF-γ (−81%; $p<0.001$), but no statistically significant changes for KC (+20%), TNF-α (−13%), and CXCL-10 (−8%).

Clinically, Compound 17ya treatment resulted in a reduction in the severity of lung inflammation (by histopathology) and a dose-dependent improvement of lung function (lower Penh vs untreated H1N1 infection). Oral administration of 2 mg/kg Compound 17ya resulted in the reduction of the clinical signs and body weight loss associated with H1N1 infection. From Day 11, four out of seven animals displayed no clinical signs associated with the induction of H1N1 infection. Whereas, oral administration of 1 mg/kg dexamethasone did not result in reduction of the clinical signs or body weight loss associated with H1N1 infection.

These data suggest that Compound 17ya has the potential to be an effective treatment for hospitalized influenza patients at high risk for ARDS and death. Pathogenesis and mortality rates for patients with hospitalized influenza ARDS are similar to COVID-19-associated ARDS, representing a high unmet need with very limited treatment options. According to CDC, the influenza burden estimates in the United States were up to 630,000 hospitalizations and up to 55,000 deaths in the past 6 months. Accordingly, Veru is planning a double-blind randomized placebo-controlled Phase 3 clinical trial evaluating Compound 17ya in hospitalized adult influenza patients at high risk for ARDS.

"Viral-induced acute respiratory distress syndrome is a leading cause of death in patients with COVID-19 and influenza and remains an unmet medical need worldwide," said Mitchell Steiner, M.D., Chairman, President and Chief Executive Officer of Veru. Compound 17ya as a host targeted antiviral and broad spectrum anti-inflammatory agent, has the potential to address the two most common causes of viral-induced ARDS: COVID-19 and influenza. Based on the preclinical data highlighted today, we plan to initiate a Phase 3 study of Compound 17ya in influenza patients at high risk for ARDS and potentially death."

Example 2

Evaluation of Compound 17ya with Influenza Model

This study evaluated the efficacy of Compound 17ya in a murine H1N1 pulmonary inflammation model. Intranasal administration of H1N1 successfully induced pulmonary inflammation in female Balb/c mice. Vehicle, Compound 17ya, dexamethasone, and oseltamivir were orally administered for comparison. Table 2 illustrates treatment groups and doses.

TABLE 2

Treatment Groups and Doses in Study.

| Group | Treatment* q.d. | Dose (mg/kg) | Dose concentration of free base (mg/mL) | Actual viral challenge (PFU/Dose)⁺ | Animal numbers Efficacy Cohort 1 Day 5⁺⁺ | Mortality Cohort 2 Day 14 |
|---|---|---|---|---|---|---|
| 1 | Vehicle | — | — | — | 1-8 | 49-55 |
| 2 | Vehicle | — | — | 96 | 9-16 | 56-62 |
| 3 | Compound 17ya | 2 | 0.2 | 96 | 17-24 | 63-69 |
| 4 | Compound 17ya | 8 | 0.8 | 96 | 25-32 | 70-76 |
| 5 | Dexamethasone | 1 | 0.1 | 96 | 33-40 | 77-83 |
| 6 | Oseltamivir** | 30 | 3 | 96 | 41-48 | 84-90 |

*Vehicle (5% DMSO in PBS), Compound 17ya, dexamethasone and oseltamivir were administered orally at a dose volume of 10 mL/kg from 2 h prior to virus administration on Day 0.
**Oseltamivir was administered twice daily from 2 h prior to virus administration on Day 0.
⁺H1N1 was administered intranasally, at a fixed dose volume of 50 μL per animal on Day 0.
⁺⁺Efficacy Animals were terminated on Day 5, Mortality Study animals were terminated on Day 14 (unless culled earlier for welfare reasons).

Groups 1 and 2 were administered a vehicle of 5% DMSO in PBS. Groups 3 and 4 were administered Compound 17ya HCl salt in either 0.22 mg/mL (Group 2) or 0.88 mg/mL (Group 3) in 5% DMSO in PBS. Group 5 was administered dexamethasone (0.1 mg/mL) in 0.5% HPMC/0.1% Tween 80 in distilled water. Group 6 was administered oseltamivir (3 mg/mL) in water for injection.

Female Balb/C mice were acclimatized for 14 days before Day 0, when they were randomized into study groups so that the group mean weights were approximately equal. The mice were fed a Teklad 2014C pelleted diet, which was non-restricted except during study procedures.

On Day 0, under recoverable anesthesia (isoflurane/oxygen mix) animals were inoculated with PBS (Group 1) or H1N1 (PR8) (Groups 2-6) by intranasal administration. All animals (1-90) were dosed with a fixed volume of 50 μL. From Day 1, all animals were weighed daily until termination, their body temperature was assessed twice daily and on Days 1, 3, 5, and 7 all animals in cohort 2 (49-90) had their lung function assessed by non-invasive whole body plethysmography for minute volume (MV), tidal volume (TV), respiratory rate (RR), and enhanced pause (penh).

On day 5, animals 1-48 were terminated and a brochoalveolar lavage (BAL) sample was taken. From the sample, a cell pellet was formed and then resuspended in 0.5 mL PBS and stored on wet ice prior to a total and differential cell count using a XT 2000iV (Sysmex UK Ltd). A total and differential cell count (including neutrophils, lymphocytes, eosinophils and mononuclear cells (includes monocytes and macrophages)) were reported as number of cells per animal. Thereafter, lungs were excised and weighed. The whole lung was then insufflated with 10% neutral buffered formalin for a minimum of 24 hours and the tissues were processed to paraffin blocks. Levels of cytokines interferon-gamma (IFN-γ), interleukin-6 (IL-6), interferon-gamma inducible protein of 10 kDa (IP-10), a chemokine receptor CXCR2 ligand (KC; a neutrophil attractant) and tumor necrosis factor-alpha (TNF-α) in the BAL fluid were analyzed using a Multiplex System (an ELISA) in singlet.

From Day −1 Animals 49-90 were assessed for bodyweight, body temperature, and clinical signs. On Day 14 any surviving animals had their clinical signs (including bodyweight and body temperature) assessed in the morning and were culled and discarded without further necropsy.

For data evaluation body weights, body temperatures and clinical observations were reported. For Longitudinal Lung Function, the respiratory rate (RR), tidal volume (TV), minute volume (MV), and penh (PENH) were reported from Days 1, 3 and 5. Respiratory parameters were reported for the following time points: 0, 11, 12, 13, 14, 15, 16, 17, 18, 19, 20 min post-recording start.

BAL fluid (BALF) total and differential cell counts were reported. Cells were classified as neutrophils, lymphocytes, eosinophils and mononuclear cells (includes monocytes and macrophages). The number of each cell type were recorded as million/animal. BALF cytokine levels were expressed as pg/mL.

Statistical Analysis: Body temperature, longitudinal lung function parameters (RR, TV, MV and PENH), BAL total and differential cell counts, BAL cytokines (IFN-γ, IL-6, IP-10, KC and TNF-α) and wet lung weights were analyzed, for each parameter and time point separately, using one-way analysis of variance (ANOVA). A rank transformation was applied to BAL total and differential cell counts and BAL cytokines data prior to analysis. Group comparisons were made for Groups 1, 3, 4, 5 and 6 against Group 2 (infected but treated with vehicle). For BAL total and differential cell counts, BAL cytokines and wet lung weight these tests were interpreted with 1-sided risk for a decreasing response from Group 2 (note, a decreasing response in Group 1 from Group 2 is equivalent to an increasing response in Group 2 from Group 1). For all other parameters these tests were interpreted with 2-sided risk.

Results

Clinical Signs. Intranasal administration of H1N1 resulted in adverse clinical signs, being observed from the afternoon of Day 2. These increased in incidence and severity throughout the experiment. Clinical signs included fast respiration, piloerection and hunched posture. No clinical signs were observed in the vehicle negative control group. A clinical sign score post H1N1 administration is illustrated in FIG. 1 for each treatment group.

Once daily oral administration of 2 mg/kg Compound 17ya resulted in the attenuation of the clinical signs associated with H1N1 infection with only mild clinical signs being observed from Day 2 and from Day 11 in only 3 of the 7 animals. Once daily oral administration of 8 mg/kg Compound 17ya resulted in an exacerbation of the clinical signs associated with H1N1 infection from Day 10. One out of the seven animals in this group had to be culled for welfare reasons on Day 12. Once daily oral administration of 1 mg/kg dexamethasone resulted in no attenuation of the clinical signs associated with H1N1 infection. Three out of the seven animals in this group had to be culled for welfare reasons on Day 11. Twice daily oral administration of 30 mg/kg oseltamivir resulted in the attenuation of the clinical signs associated with H1N1 infection with only mild clinical signs being observed (FIG. 1).

Figure 2A:
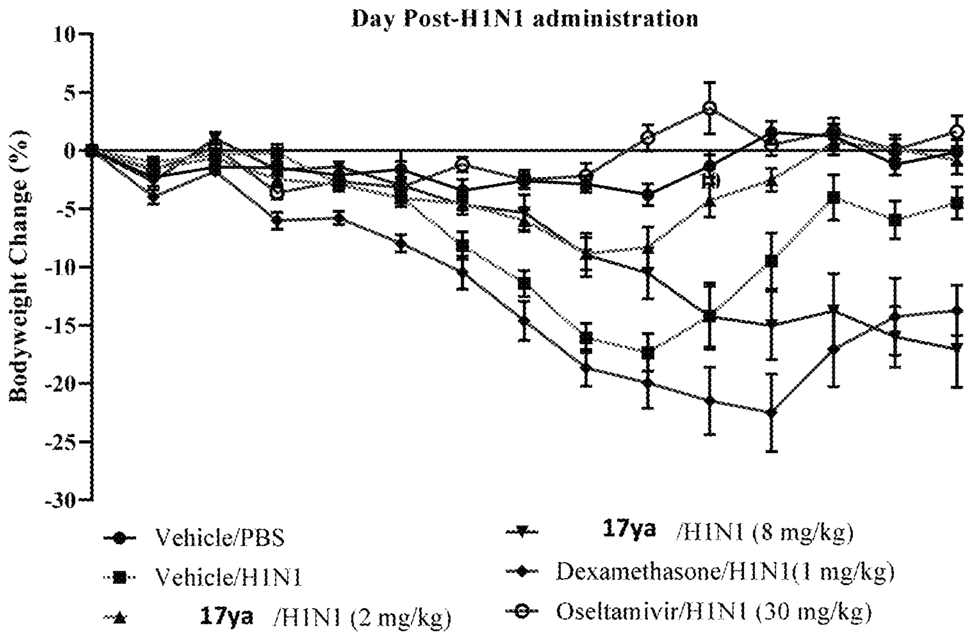
FIGS. 2A and 2B illustrate the effect of Compound 17ya on bodyweight gain in the H1N1 induced pulmonary inflammation model.
Figure 2B:
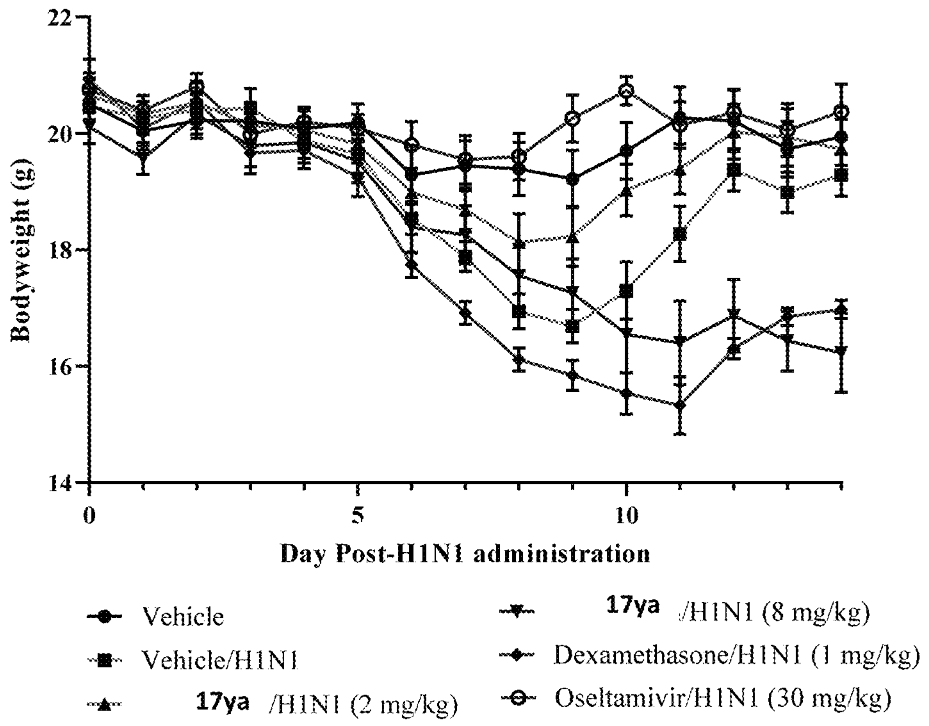

Body weight gain. Intranasal administration of H1N1 resulted in statistically significantly lower ($p<0.01$) body weight gain from Day 7 to 11 when compared to the vehicle control group. Once daily oral administration of 2 mg/kg Compound 17ya resulted in statistically significantly higher ($p<0.05$) body weight gain from Day 8 to 10 when compared to the H1N1 vehicle control group. Once daily oral administration of 8 mg/kg Compound 17ya resulted in statistically significantly lower ($p<0.05$) body weight from Day 11 when compared to the HIN1 vehicle control group. Once daily oral administration of 1 mg/kg dexamethasone resulted in statistically significantly lower ($p<0.05$) body weight from Day 10 when compared to the HIN1 vehicle control group. Twice daily oral administration of 30 mg/kg oseltamivir resulted in statistically significantly higher ($p<0.01$) body weight gain from Day 6 to Day 11 when compared to the HIN1 vehicle control group. FIGS. 2A and 2B illustrate the effect of Compound 17ya on bodyweight gain in the H1N1 induced pulmonary inflammation model.

Effect of Compound 17ya on BAL and Differential Cell Counts on Day 5. On Day 5 post induction of inflammation, administration of H1N1 resulted in statistically significantly ($p<0.001$) higher total BAL cells, neutrophils, eosinophils, mononuclear cells (macrophages) and lymphocytes when compared to the saline control group. Once daily oral administration of Compound 17ya at a dose of 2 mg/kg resulted in no statistically significant changes in BAL cells when compared to the H1N1 control group; however once daily oral administration of Compound 17ya at a dose of 8 mg/kg resulted in statistically significantly ($p<0.01$) lower BAL total cells, neutrophils, mononuclear cells, lymphocytes, and eosinophils when compared to the H1N1 control group. Once daily oral administration of dexamethasone at a dose of 1 mg/kg resulted in lower but not statistically significant total BAL cells, neutrophils, eosinophils, mononuclear cells (macrophages) and lymphocytes when compared to the H1N1 control group. Once daily oral administration of oseltamivir at a dose of 30 mg/kg resulted in statistically significantly ($p<0.01$) lower BAL total cells, neutrophils, eosinophils, lymphocytes, and mononuclear cells when compared to the H1N1 control group.

Figure 3A:
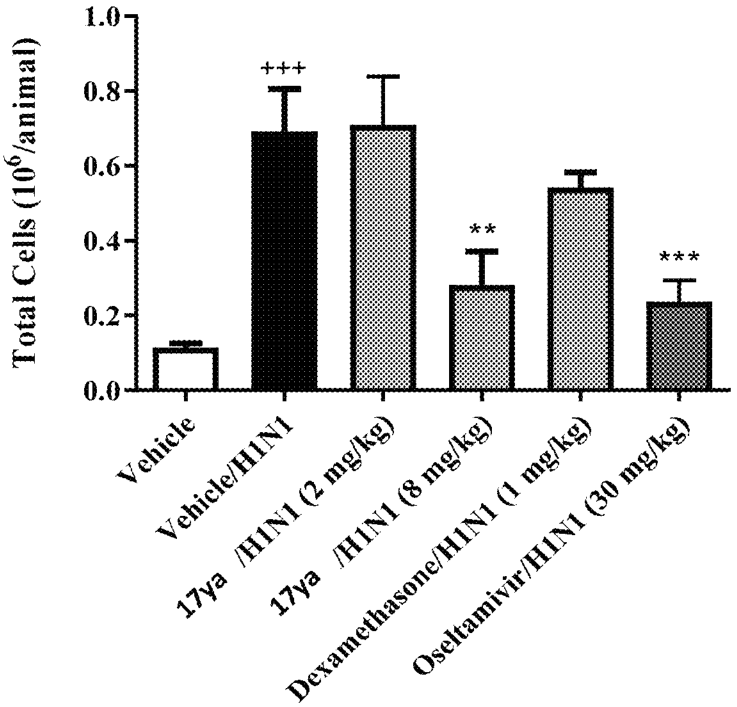
FIGS. 3A-3E illustrate the effect of Compound 17ya on BAL (bronchoaveolar lavage) total and differential cell counts in the H1N1 model for induced pulmonary inflammation at day 5.
Figure 3B:
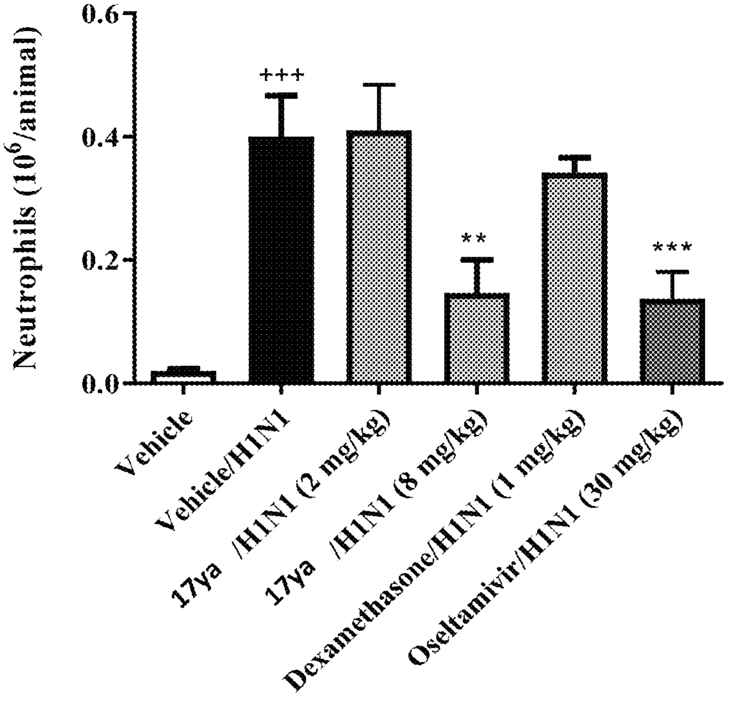
Figure 3C:
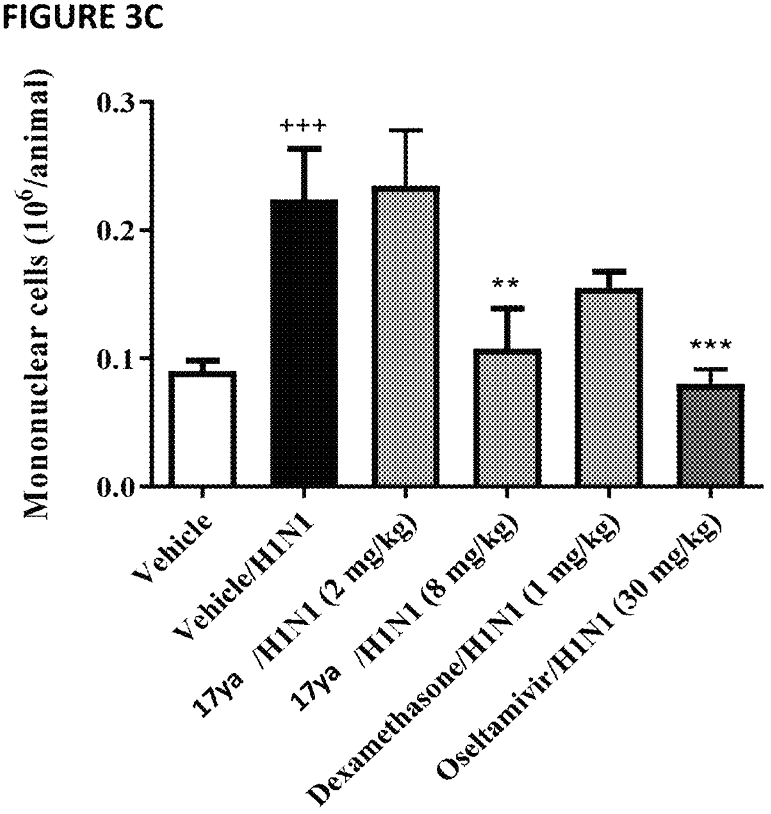
Figure 3D:
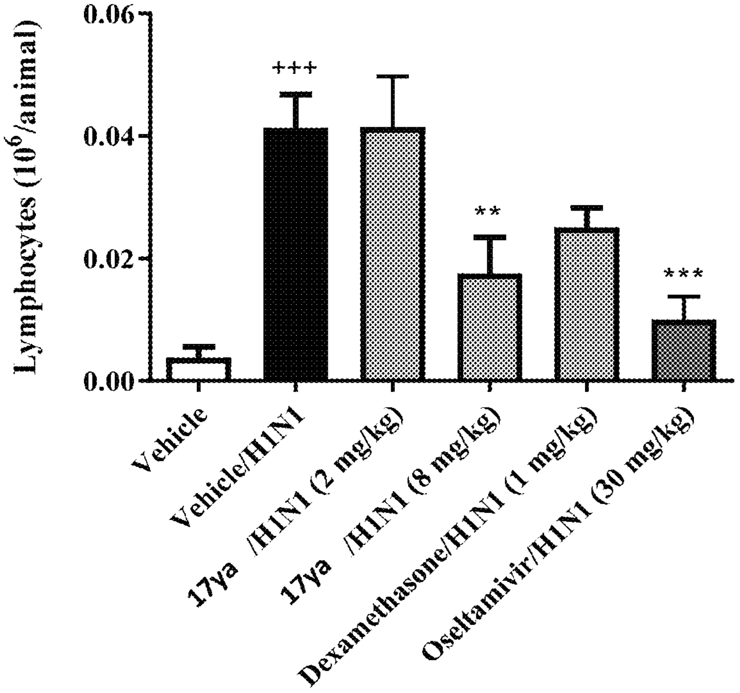
Figure 3E:
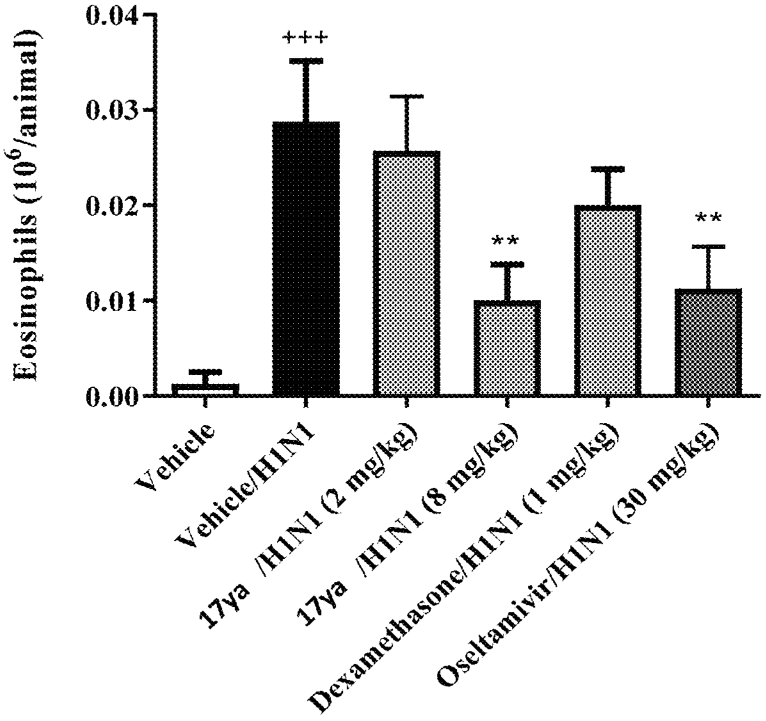

FIGS. 3A-3E illustrate the effect of Compound 17ya on BAL total and differential cell counts in the H1N1 model for induced pulmonary inflammation at day 5. FIG. 3A illustrates the effect on total cell count of Compound 17ya, vehicle, dexamethasone, and oseltamivir. FIG. 3B illustrates the effect on neutrophil count of Compound 17ya, vehicle, dexamethasone, and oseltamivir. FIG. 3C illustrates the effect on mononuclear cells of Compound 17ya, vehicle, dexamethasone, and oseltamivir. FIG. 3D illustrates the effect on lymphocytes of Compound 17ya, vehicle, dexamethasone, and oseltamivir. FIG. 3E illustrates the effect on eosinophils of Compound 17ya, vehicle, dexamethasone, and oseltamivir. The data is presented in Table 3 below.

TABLE 3

Effect of Compound 17ya on BAL total and differential cell counts.

| Group | Treatment | Cell counts (million/animal) Mean ± s.e.m. Totals | Neutrophils | Eosinophils | Lymphocytes | Mononuclear cells |
|---|---|---|---|---|---|---|
| 1 | Vehicle/Vehicle | 0.11 ± 0.01 | 0.02 ± 0.00 | 0.00 ± 0.00 | 0.09 ± 0.01 | 0.00 ± 0.00 |
| 2 | Vehicle/H1N1 challenge | 0.69+++ ± 0.11 | 0.40+++ ± 0.07 | 0.04+++ ± 0.01 | 0.22+++ ± 0.04 | 0.03+++ ± 0.01 |
| 3 | Compound 17ya 2 mg/kg/H1N1 challenge | 0.71 ± 0.13 | 0.41 ± 0.07 | 0.04 ± 0.01 | 0.23 ± 0.04 | 0.02 ± 0.01 |
| 4 | Compound 17ya 8 mg/kg/H1N1 challenge | 0.32** ± 0.09 | 0.17** ± 0.06 | 0.02** ± 0.01 | 0.12** ± 0.03 | 0.01** ± 0.00 |
| 5 | Dexamethasone 1 mg/kg/H1N1 challenge | 0.54 ± 0.04 | 0.34 ± 0.03 | 0.03 ± 0.00 | 0.15 ± 0.01 | 0.02 ± 0.00 |
| 6 | Oseltamivir 30 mg/kg/ H1N1 challenge | 0.27*** ± 0.06 | 0.15*** ± 0.04 | 0.01** ± 0.00 | 0.09*** ± 0.01 | 0.01*** ± 0.00 |

Values rounded, precision may not be as displayed.

s.e.m. Standard error of the mean.

**$p < 0.01$,

***$p < 0.001$ when compared to the vehicle/H1N1 challenged group.

+++$p < 0.001$ when compared to the vehicle/vehicle group.

Effect of Compound 17ya on BAL Cytokine Levels. On Day 5 post induction of inflammation, administration of H1N1 resulted in statistically significantly ($p<0.001$) higher TNFα, IFNγ, IL-6, KC, and IP-10 levels when compared to the saline control group. Once daily oral administration of Compound 17ya at a dose of 2 mg/kg resulted in statistically significantly ($p<0.05$) lower BAL IL-6 and IP-10 when compared to the H1N1 control group. Once daily oral administration of Compound 17ya at a dose of 2 mg/kg resulted in no statistically significant changes in TNFα, IFN-γ and KC when compared to the H1N1 control group. Once daily oral administration of Compound 17ya at a dose of 8 mg/kg resulted in statistically significantly ($p<0.05$) lower IFNγ, IL-6, IP-10, KC and TNFα when compared to the H1N1 control group. Once daily oral administration of dexamethasone at a dose of 1 mg/kg resulted in statistically significantly ($p<0.01$) lower BAL IL-6, KC and IFN-γ when compared to the H1N1 control group. Once daily oral administration of dexamethasone at a dose of 1 mg/kg resulted in no statistically significant changes in TNFα and IP-10 when compared to the H1N1 control group. Twice daily oral administration of oseltamivir at a dose of 30 mg/kg resulted in statistically significantly ($p<0.01$) lower TNFα, IFNγ, IL-6, KC, and IP-10 when compared to the H1N1 control group.

Figure 4A:
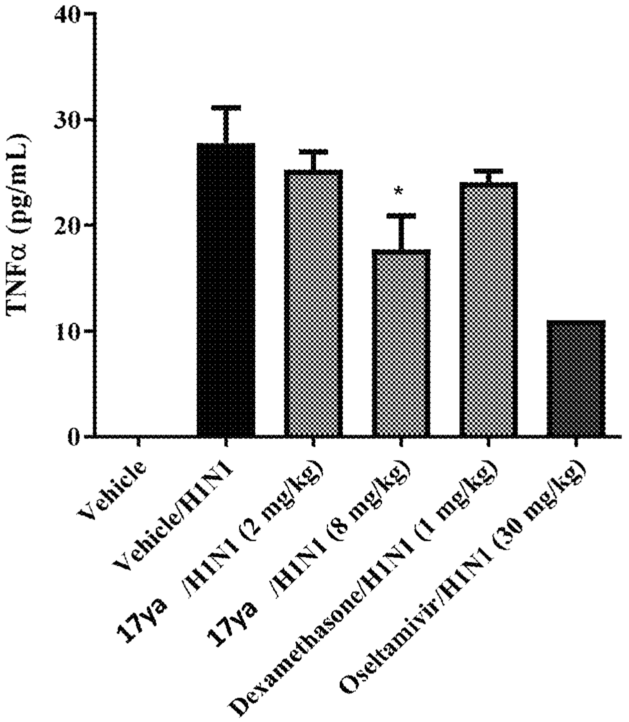
FIGS. 4A-4E illustrate the effect of Compound 17ya on BAL cytokine concentration in the H1N1 model for induced pulmonary inflammation at day 5.
Figure 4B:
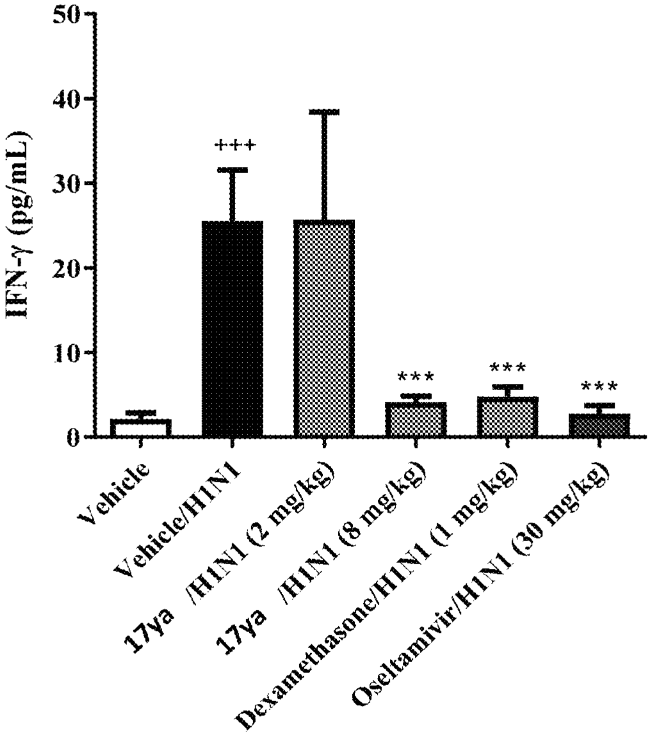
Figure 4C:
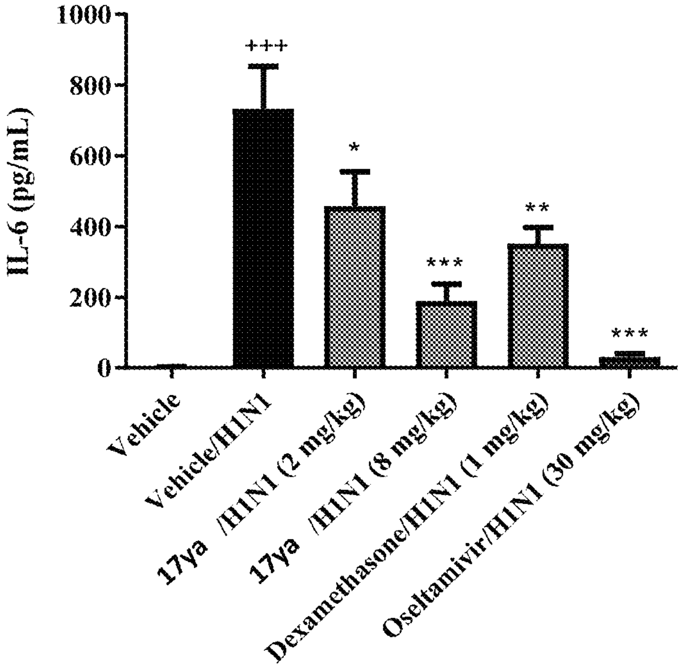
Figure 4D:
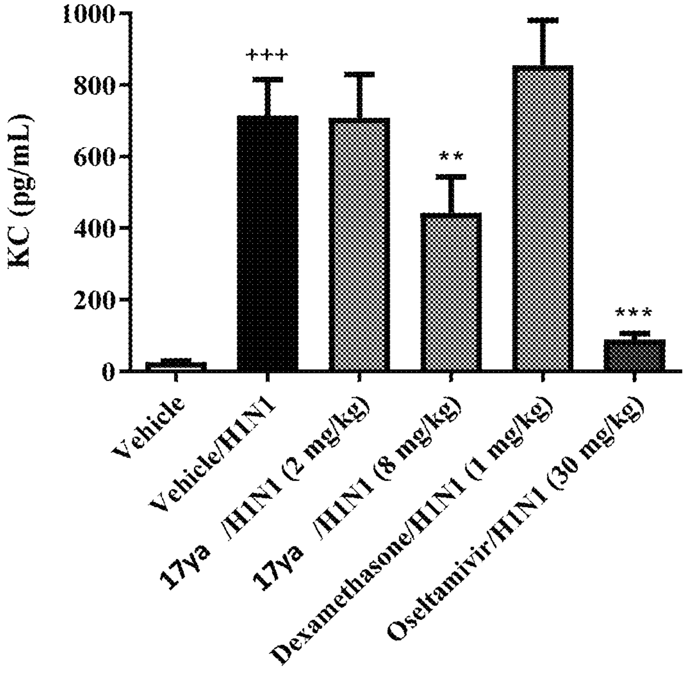
Figure 4E:
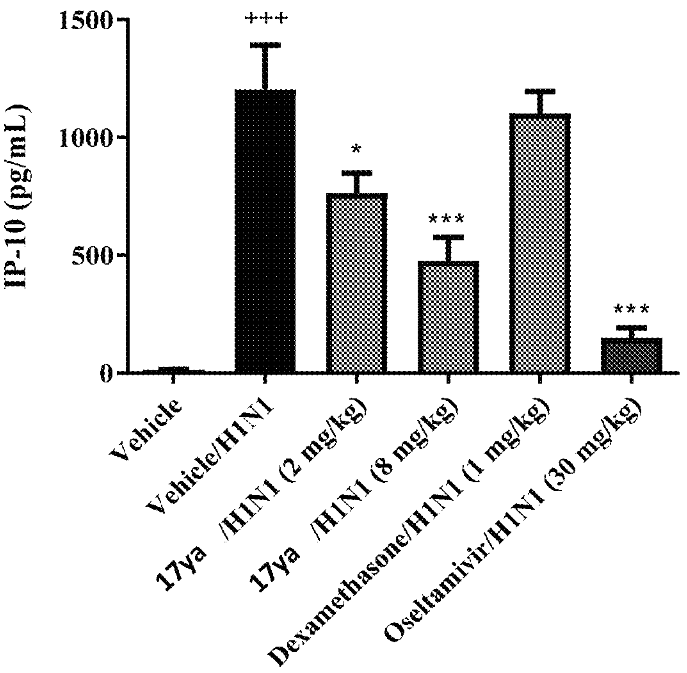

FIGS. 4A-4E illustrate the effect of Compound 17ya on BAL cytokine concentration in the H1N1 model for induced pulmonary inflammation at day 5. FIG. 4A illustrates the effect on TNFα (pg/mL) of Compound 17ya, vehicle, dexamethasone, and oseltamivir. FIG. 4B illustrates the effect on IFN-γ of Compound 17ya, vehicle, dexamethasone, and oseltamivir. FIG. 4C illustrates the effect on IL-6 of Compound 17ya, vehicle, dexamethasone, and oseltamivir. FIG. 4D illustrates the effect on KC of Compound 17ya, vehicle, dexamethasone, and oseltamivir. FIG. 4E illustrates the effect on IP-10 of Compound 17ya, vehicle, dexamethasone, and oseltamivir. Table 4 summarizes the data for the study.

TABLE 4

Effect of Compound 17ya on BAL cytokine concentrations

| Group | Treatment | BAL Cytokine level (pg/ml) Mean ± s.e.m. | | | | |
|---|---|---|---|---|---|---|
| | | TNF-α | IFN-γ | IP-10 | IL-6 | KC |
| 1 | Vehicle/Vehicle | NP<br>NP | 2.13 ±<br>0.71 | 13.33 ±<br>1.62 | 2.83 ±<br>0.92 | 25.38 ±<br>2.85 |
| 2 | Vehicle/H1N1 challenge | 27.78 ±<br>3.33 | 25.54+++ ±<br>6.03 | 1203.57+++ ±<br>189.10 | 732.74+++ ±<br>120.48 | 714.38+++ ±<br>100.91 |
| 3 | Compound 17ya 2 mg/kg/ H1N1 challenge | 25.24 ±<br>1.57 | 25.67 ±<br>12.74 | 764.15* ±<br>85.25 | 456.81* ±<br>98.77 | 707.41 ±<br>122.09 |
| 4 | Compound 17ya 8 mg/kg/ H1N1 challenge | 17.70* ±<br>2.26 | 4.11*** ±<br>0.74 | 475.93*** ±<br>99.23 | 189.87*** ±<br>46.92 | 442.21** ±<br>100.81 |
| 5 | Dexamethasone 1 mg/kg/ H1N1 challenge | 24.08 ±<br>1.06 | 4.80*** ±<br>1.05 | 1102.42 ±<br>93.39 | 351.37** ±<br>45.32 | 854.41 ±<br>126.38 |
| 6 | Oseltamivir 30 mg/kg/ H1N1 challenge | NP<br>NP | 2.78*** ±<br>0.95 | 147.64*** ±<br>43.66 | 31.01*** ±<br>9.28 | 88.29*** ±<br>17.35 |

NP Not processable.
Values rounded, precision may not be as displayed.
s.e.m. Standard error of the mean.
+++p < 0.001 when compared to the vehicle/vehicle group
*p < 0.05,
**p < 0.01,
***p < 0.001 when compared to the vehicle/H1N1 challenged group Effect of Compound 17ya on Histopathology. The administration of 2 or 8 mg/kg/day of Compound 17ya to Balb/c mice resulted in a reduction in the severity of lung inflammation considered to be related to the viral challenge of HIN1, when compared with the viral challenged vehicle control group. Reduced severity of lung inflammation was seen in animals administered dexamethasone when compared to the viral challenge control group. Reduced incidence and severity of inflammation were seen in animals administered oseltamivir when compared to the viral challenged control group. When comparing the efficacies of the two compounds, Compound 17ya and oseltamivir, in reducing lung inflammation, slightly less efficacy was recorded with Compound 17ya at 2 or 8 mg/kg/day when compared with oseltamivir.

Intranasal administration of H1N1 resulted in successful induction of pulmonary inflammation. This was demonstrated by lower bodyweight gain and lower body temperature when compared to the saline controls, as well as by higher wet lung weights (not shown here), total BAL, differential cell counts and BAL IFNγ, IL-6, IP-10 and KC BAL cytokine levels when compared to the saline controls. Changes in lung function were also observed including higher PenH on Days 5 and 7 when compared to the saline controls.

Oral administration of 2 mg/kg of Compound 17ya resulted in the reduction of the clinical signs and body weight loss associated with H1N1 infection. From Day 11, four out of seven animals displayed no clinical signs associated with the induction of H1N1 infection. The oral administration of 8 mg/kg Compound 17ya resulted in a slight exacerbation of the clinical signs or bodyweight loss associated with H1N1 infection, with one out of the seven animals in this group having to be culled for welfare reasons on Day 12. No animals were terminated early in the H1N1 vehicle control group.

Oral administration of 1 mg/kg dexamethasone resulted in no attenuation of the clinical signs or body weight loss associated with H1N1 infection. Three out of the seven animals in this group had to be culled for welfare reasons on Day 11, primarily as a result of exacerbated bodyweight loss. The oral administration of 30 mg/kg oseltamivir attenuated the clinical signs and bodyweight loss associated with H1N1 infection.

Intranasal administration of H1N1 resulted in no changes in minute volume, tidal volume, respiratory rate or Penh on Days 1 or 3. From Day 5 intranasal administration of H1N1 resulted in a higher PenH, a higher tidal and minute volume (Day 5 only) and a lower respiratory rate (Day 7 only) when compared to the saline controls.

On Day 5 oral administration of 2 mg/kg of Compound 17ya resulted in a lower PenH when compared to the H1N1 control group. On Day 7 once daily oral administration of 8 mg/kg of Compound 17ya resulted in a lower PenH when compared to the H1N1 control group. This effect on PenH appears to be dose dependent.

On Days 5 and 7, oral administration of 1 mg/kg dexamethasone resulted in a lower PenH and a higher tidal volume (Day 7 only) when compared to the H1N1 control group. Oral administration of 30 mg/kg oseltamivir completely attenuated H1N1 induced higher PenH on Days 5 and 7.

On Day 5 post induction of inflammation, administration of H1N1 resulted in higher total BAL cells, neutrophils, eosinophils, mononuclear cells (macrophages) and lymphocytes and higher BAL IFNγ, IL-6, IP-10, KC and TNFα levels when compared to the saline control group.

Oral administration of 2 mg/kg of Compound 17ya resulted in no changes in BAL cells or TNFα, IFN-γ and KC when compared to the H1N1 control group. However, oral administration of 2 mg/kg of Compound 17ya resulted in lower BAL IL-6 and IP-10. Oral administration of 8 mg/kg of Compound 17ya resulted in lower BAL total cells, neutrophils, eosinophils, lymphocytes, mononuclear cells BAL IFNγ, IL-6, IP-10, KC and TNFα when compared to the H1N1 control group.

Oral administration of 1 mg/kg of dexamethasone resulted in lower, but not statistically significant total BAL cells, neutrophils, eosinophils, mononuclear cells (macrophages) and lymphocytes when compared to the H1N1 control group. Once daily oral administration of dexamethasone resulted in lower BAL IL-6, KC and IFN-γ when compared to the H1N1 control group.

Oral administration of 30 mg/kg of oseltamivir resulted in statistically significantly lower BAL total cells, neutrophils, eosinophils, lymphocytes, mononuclear cells BAL IFNγ, IL-6, IP-10, KC and TNFα when compared to the HIN1 control group.

The administration of 2 or 8 mg/kg/day of Compound 17ya to Balb/c mice resulted in a reduction in the severity of lung inflammation considered to be related to the viral challenge of H1N1, when compared with the viral challenged control group. Reduced severity of lung tissue inflammation was recorded in animals administered dexamethasone, compared to the viral challenge control group. Reduced incidence and severity of lung tissue inflammation were recorded in animals administered oseltamivir when compared to the viral challenged control group.

Example 3

Preclinical Study Results Demonstrate that Compound 17ya Inhibits Pox Virus including inhibited the cell release and cell-to-cell spread of pox virus Results from a preclinical study evaluating the effects of Compound 17ya against prototypical *Orthopoxvirus*, vaccinia pox virus, demonstrated that Compound 17ya prevented both the release of pox virus from infected cells and spread of pox virus to healthy cells. The materials and methods are reported in Example 4, and this abstract reviews the data presented in more detail in Example 4. These preclinical study results expand the possible use of Compound 17ya as a treatment for the highly lethal smallpox virus infection in order to be prepared for a worldwide emergency outbreak as well as other infections caused by pox viruses which are a significant global public health issue.

Preclinical study background: The purpose of the study was to evaluate the mechanism of antiviral efficacy of Compound 17ya, a microtubule disruptor agent, against the prototypical vaccinia pox in cell culture. Vaccinia pox virus uses the host cell's microtubules for intracellular transport to reproduce, and to release out of the cell newly formed infectious viral particles called extracellular enveloped virus (EEV) which then spread to healthy cells to cause widespread virus infection.

Preclinical study results highlights: Treatment of BSC40 cells (African green monkey kidney cells) with different concentrations of Compound 17ya before being inoculated with vaccinia pox virus demonstrated a drug dose-dependent inhibition of infectious extracellular enveloped virus (EEV) release ($R^2$ value=0.9573) with an inhibition concentration of 50% and 90% at 24.3 nM and 37.8 nM concentrations of Compound 17ya, respectively. To assess the ability of Compound 17ya to slow or stop vaccina pox virus cell-to-cell spread, BSC40 cells were treated with different concentrations of Compound 17ya before being inoculated with vaccinia pox virus at a low multiplicity of infection. A clear drug dose-dependent inhibition of cell-to cell spread of vaccinia pox virus was observed ($R^2$=0.9464) with an inhibition concentration of 50% and 90% at 15.7 nM and 27 nM concentrations of Compound 17ya, respectively.

The concentrations of Compound 17ya required to inhibit vaccinia pox virus release from infected cells and to stop cell-to-cell spread may be achieved at the 9 mg daily dose of Compound 17ya as patients treated with 9 mg oral daily doses of Compound 17ya have an average blood concentration ($C_{avg}$) of about 32 nM Compound 17ya and peak concentration levels ($C_{max}$) of 171 nM Compound 17ya.

In this study, Compound 17ya by disrupting microtubules, was able to prevent the export and release of infectious vaccinia pox (EEV). These findings are consistent with Compound 17ya's mechanism of action as an indirect antiviral as it targets a component of the cell, microtubules, that viruses use to cause infection.

Compound 17ya, as a host targeted antiviral and broad anti-inflammatory agent, may be useful as a novel treatment not only against smallpox and other pox infections, but also the hyperactive immune response triggered by pox virus that is responsible for severe pneumonia, ARDS, multi-organ failure, and death.

Example 4

Antiviral Testing of 17Ya Hydrochloride Salt Against the Prototypical Poxvirus Vaccinia Background: *Orthopoxviruses* continue to represent a significant global public health issue. While naturally occurring variola virus, the causative agent of smallpox, has been eradicated, there are still credible concerns about its use as a bioterror agent. Monkeypox virus is an emerging infectious disease that is endemic in Africa. Last year the Democratic Republic of the Congo reported over 4,000 cases of Monkeypox with a fatality rate of ~4%. Currently, there is a global monkeypox outbreak with over 30,000 cases in the US and 28 deaths. In addition to monkeypox, other *Orthopoxvirus* outbreaks have recently occurred. A documented infection with an unknown *Orthopoxvirus* was recently discovered in the US. A feral vaccinia virus (VACV) in Brazil has led to sporadic outbreaks over the past few years with some infections leading to hospitalization.

Recent cases have occurred in Colombia, Argentina, and Uruguay indicating that the virus is spreading across South America and may be heading into Central America. These instances underscore the continued importance of *Orthopoxviruses* to public health and highlight the main reason that multiple *Orthopoxviruses* are listed as Category A priority pathogens and emerging infectious diseases by both NIH/NIAID and the WHO. While the current monkeypox outbreak is subsiding, it has highlighted the pandemic potential of the virus and underscores the need for additional vaccines and antivirals against these viruses.

Viruses are intracellular pathogens and as such are dependent on the host cell for multiple aspects of their replication. Amongst the many cellular systems commandeered by viruses, the cytoskeleton, which serves as the intracellular transportation system, is typically engaged at 2 separate stages of viral replication, entry and egress. Thus, targeting this essential system with indirect anti-viral compounds would potentially target both the beginning and ending stages of viral replication. In accordance with this, the *Orthopoxvirus* has been shown to engage the microtubule system at the beginning of cellular infection for transport of particles to the juxta-nuclear region where viral replication occurs and during morphogenesis to transport progeny virions out of the cell. Here we conducted experiments to determine if the microtubule targeting drug 17ya is capable of interfering with the replication cycle and spread of the prototypical *Orthopoxvirus* vaccinia.

Methods:

Reagents, cells and virus: 17ya hydrochloride salt was diluted to 8,000 μM in tissue culture grade dimethyl sulfoxide (DMSO), dispensed into 1 mL aliquots and stored at 4° C. CellTiter-Glo® was obtained from Promega. Before the initial use, CellTiter-Glo® reagents were mixed according to supplier's instructions, divided into 10 mL aliquots and frozen at −20° C. until used. African Green Monkey kidney cell line BSC40 was obtained from ATCC (CRL-2761) and maintained in Dulbecco's modified eagle media (DMEM) supplemented with 8% Cosmic Calf Serum® (Hyclone). The recombinant reporter vaccinia virus (VVEGIR), which expresses a green fluorescent protein (mNeonGreen) under an early promotor and a red fluorescent protein (mKate2) under an intermediate promoter, was created from the Western Reserve (WR) strain of vaccinia virus.

Determination of the concentration of 17ya that reduces proliferation of BSC40 cells by 50% ($CC_{50}$) and 90% ($CC_{90}$). $1\times10^4$ BSC40 cells were seeded into a 96 well plate and incubated overnight (o/n) at 37° C. The following day, cell media was removed and replaced with 100 μL of fresh media. 17ya hydrochloride salt was diluted to a concentration of 800 nM in DMEM and 100 μL was added to the first row of cells to give a starting concentration of 400 nM. 1:2 serial dilutions were performed in subsequent wells to give concentrations of 200, 100, 50, 25, and 12.5 nM in triplicate. To 3 wells, a concentration of DMSO was added equal to the concentration found in the 400 nM wells. Treated cells were incubated o/n at 37° C. The next day, cells were washed 1× in phosphate buffered saline (PBS). 100 μL of fresh DMEM was added followed by 100 μL of CellTiterGlo®. This was shaken for 2 minutes and then transferred to an opaque 96 well plate. Luminescence was read using a luminometer with a 1 second integration time. Luminescence is directly proportional to the number of viable cells. This assay was repeated twice with 3 replicates each time. Data was exported to MS Excel for analysis. Wells were averaged and compared to the DMSO treated cells. Linear regression was used to calculate $CC_{50}$ and $CC_{90}$.

High Multiplicity of Infection (MOI) Growth curve: $5\times10^5$ BSC40 cells were seeded into each well of 2, 12-well plates and incubated o/n at 37° C. The following day, cell media was removed and replaced with 1 mL of fresh media containing 20, 10, 5, 1, 0.5, 0.25, or 0 nM (DMSO) 17ya hydrochloride salt. 1 hour later, $2\times10^6$ plaque forming units (PFU) of VVEGIR was added and the cells were incubated at 37° C. for 2 hours. After, cells were washed 1 time in fresh DMEM and media containing the original concentration of drug was added. Cells were incubated o/n at 37° C. The following day, virus released into the supernatant was quantified (titered) by serial dilution and plaque assay on monolayers of BSC40 cells. To quantify virus associated with the cells, infected cells were harvested by scraping and transferred to a 1.5 mL screwcap tube. Virus in the cells were released by 3 freeze-thaw cycles and titered as above. Three days post infection monolayers were stained with crystal violet and the number of plaques in the well was counted. Data was analyzed using Microsoft Excel.

Low MOI Growth curve: $5\times10^5$ BSC40 cells were seeded into each well of 2, 12-well plates and incubated o/n at 37° C. The following day, cell media was removed and replaced with 1 mL of fresh media containing 30, 25, 20, 15, 10, 5, 1, or 0 nM (DMSO) 17ya hydrochloride salt. 1 hour later, $1\times10^3$ plaque forming units (PFU) of VVEGIR was added and the cells were incubated at 37° C. for 48 h at 37° C. 48 h post infection, cells in each well were harvested by scraping and transferred to a 1.5 mL screwcap tube. Virus in the cells were released by 3 freeze-thaw cycles and titered by serial dilution and plaque assay on monolayers of BSC40 cells. Data was analyzed using Microsoft Excel.

Results:

Cytotoxicity determination. Treatment of BSC40 cells with varying concentrations of 17ya hydrochloride (17ya HCl) showed a dose response for toxicity. BSC40 cells were treated overnight with various concentrations of drug. The following day, the amount of cells remaining was determined by CellTiterGlo® Assay. Results represent the average of 3 separate wells at each concentration for each trial and are shown as a percentage of cells treated with DMSO.

Figure 5:
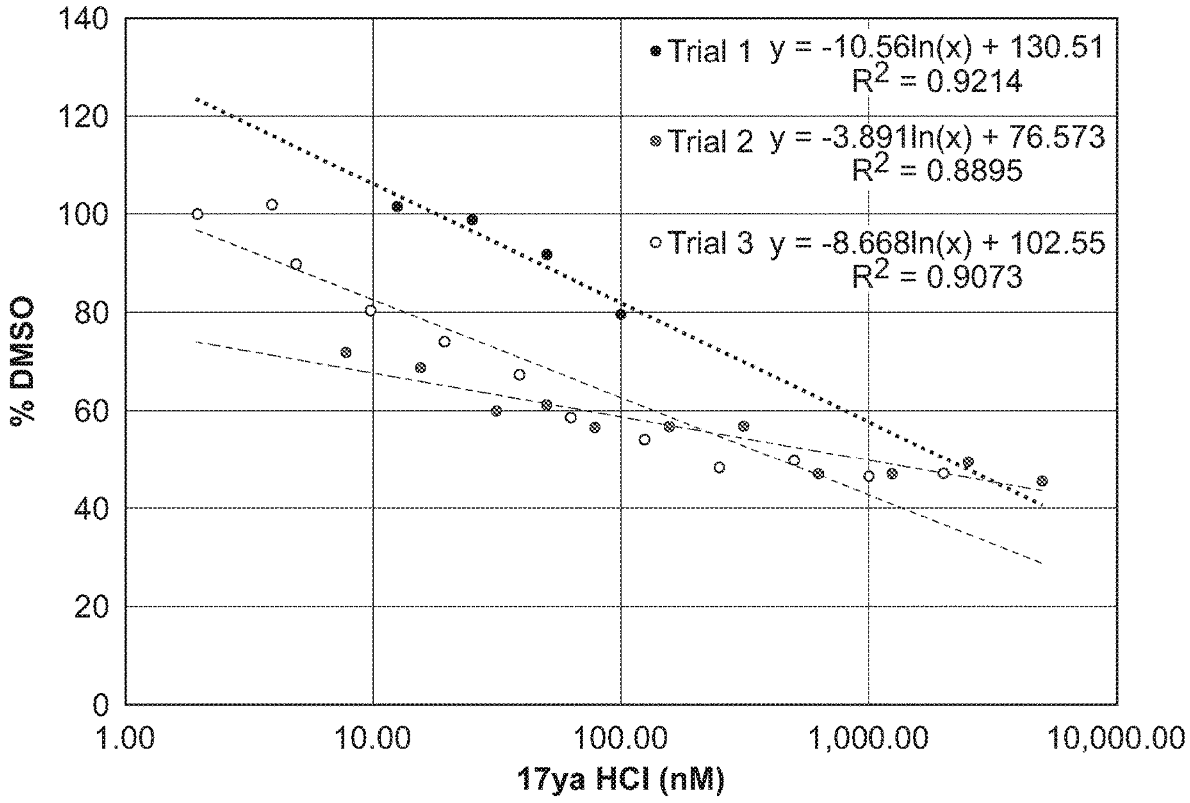
FIG. 5 illustrates the effect of various concentrations of 17ya hydrochloride salt on BSC40 cells. BSC40 cells were treated overnight with various concentrations of drug. The following day, the amount of cells remaining was determined by CellTiterGlo® Assay. Results represent the average of 3 separate wells at each concentration for each trial and are shown as a percentage of cells treated with DMSO.

Plotting out the relationship between concentrations of drug and % toxicity compared to DMSO treatment resulted in responses with $R^2$ values of 0.9214, 0.8895, and 0.9073 for trials 1, 2, and 3 respectively (FIG. 5). Using the equations determined for the best fit line for each trial, 50% toxicity values for Trials 1, 2, and 3 were calculated at 2,046.8, 924.6, and 429.5 nM, respectively. Furthermore, 90% toxicity for Trials 1, 2, and 3 were calculated at 90,393.9, 26,949,718.9 and 43,356.1 nM, respectively (FIG. 5).

Figure 6:
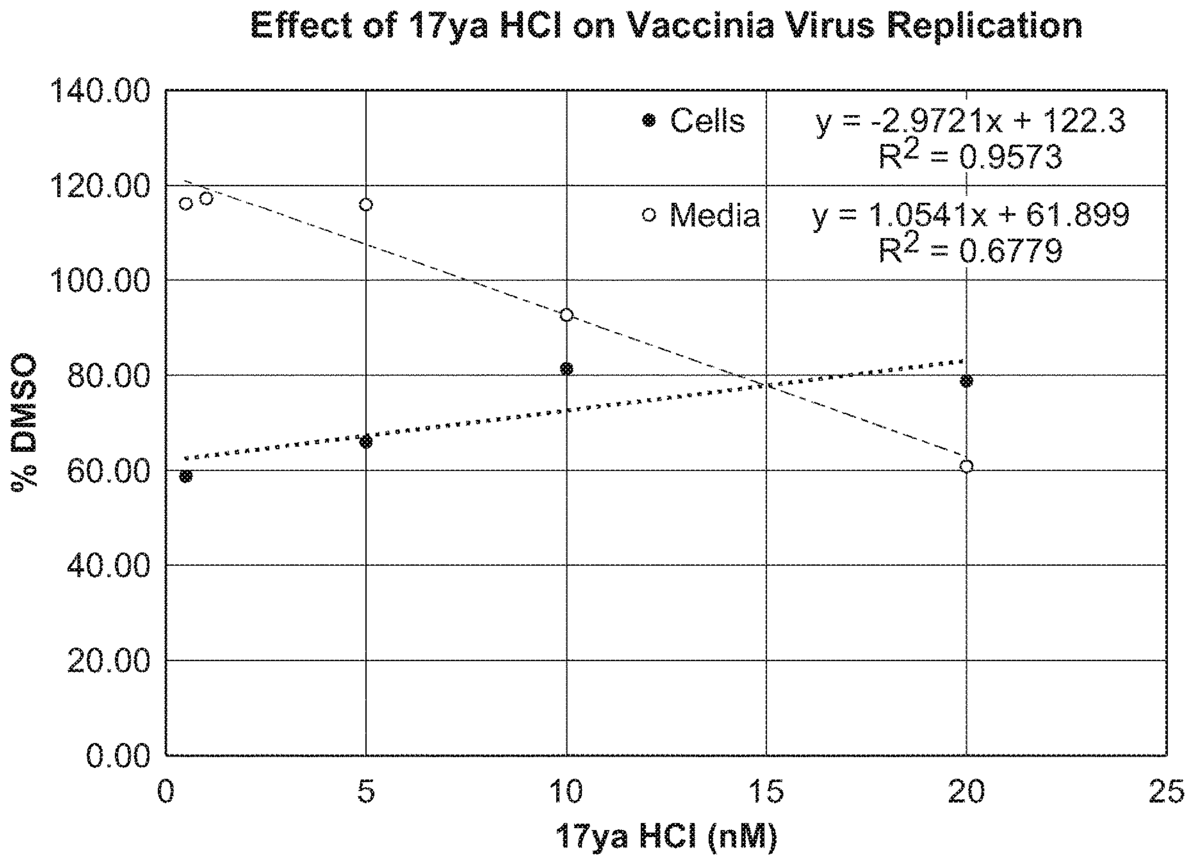
FIG. 6 illustrates the effect of 17ya hydrochloride salt on Vaccinia virus replication. Cells were treated with various concentrations of drug and then infected with a high multiplicity of infection (MOI) of virus. 24 hours later virus produced in both the cells and released into the media was quantified by plaque assay. Results represent the average of 3 replicates and are graphed compared to cells treated with DMSO.

Effect of 17ya hydrochloride salt on vaccinia virus replication. To determine if 17ya hydrochloride salt (17ya HCl) has an effect on vaccinia virus replication, cells were treated with different concentrations of the drug before being inoculated with a high multiplicity of infection (MOI) of vaccinia virus. After inoculation, unbound virus was washed off and media containing drug was added. After 24 h, virus replication was determined by measuring the amount of virus in the cells and released into the media (FIG. 6). For virus in the media (Media), which represents the extra-cellular enveloped form of the virus (EEV), there is a dose dependent inhibition of virus released in the presence of 17ya HCl with an $R^2$ value of 0.9573. Using linear regression an $IC_{50}$and $IC_{90}$ of 24.3 and 37.8 nM can be calculated. For the virus associated with the infected cells (Cells), which represent the intracellular mature form of the virus (IMV), there is not a good correlation between the amount of drug and the amount of virus produced.

Figure 7:
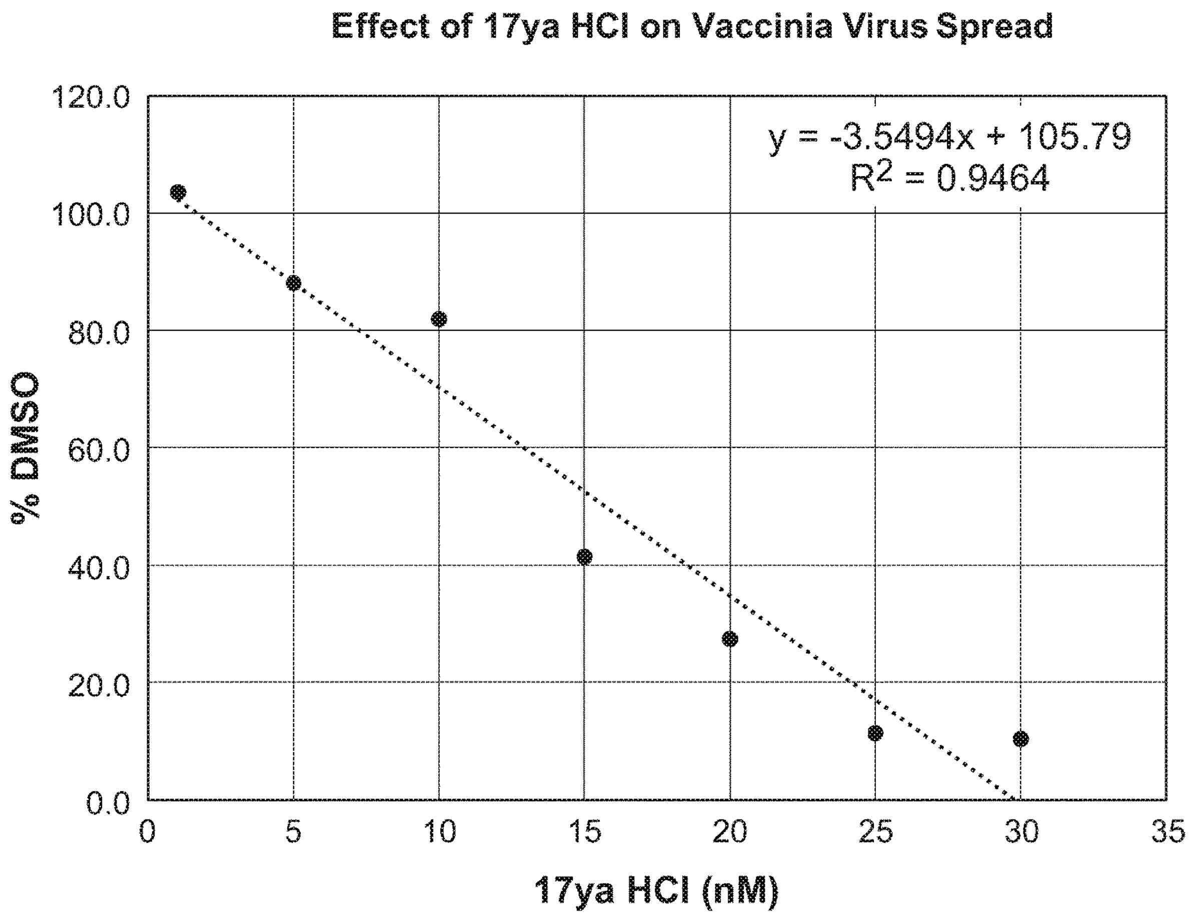
FIG. 7 illustrates the effect of 17ya hydrochloride salt on Vaccinia virus spread. Cells were treated with various concentrations of drug and then infected with a low MOI of virus. 48 hours later virus produced in the cells was quantified by plaque assay. Results represent the average of 3 replicates and are graphed compared to cells treated with DMSO.

Effect of 17ya hydrochloride salt on vaccinia virus cell-to-cell spread. To look at the ability of 17ya hydrochloride salt (17ya HCl) to slow or stop vaccinia virus cell-to-cell spread, cells were treated with different concentrations of the drug before being inoculated with a low multiplicity of infection (MOI) of vaccinia virus. After inoculation, unbound virus was washed off and media containing drug was added. After 48 h, virus replication was determined by measuring the amount of virus in the cells (FIG. 7). Graphing out the amount of virus produced vs. the concentration of 17ya HC shows a clear dose-dependent response with an $R^2$ value of 0.9464. Using linear regression an $IC_{50}$ and $IC_{90}$ of 15.7 and 27.0 nM were calculated.

Discussion

*Orthopoxviruses* such as vaccinia virus, variola virus and monkeypox virus produce two, antigenically distinct, forms of virus, the intracellular mature virus (IMV) and the extracellular enveloped (EEV). IMV represent the initial form made and are retained within the cells they are made in. EEV are derived from IMV but have an extra membrane derived from the trans Golgi network (TGN). IMV typically make up 90-99% of progeny virions while EEV make up the rest. Whereas IMV are held within infected cells, EEV utilize microtubules for active release from infected cells and are required for cell-to-cell spread and long-range transmission of infections. The results presented here show a clear effect of 17ya on the production of EEV by vaccinia virus. These results for 17ya, as a microtubule depolymerizing drug, were consistent with previous studies that suggest depolymerization of the microtubules may reduce viral trafficking to the plasma membrane preventing their release.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating an Orthomyxoviridae infection in a subject in need thereof by administering to the subject a formulation having a therapeutically effective amount of a compound of Formula (I):

(I)

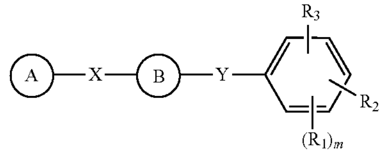

wherein

A is phenyl or indolyl, optionally substituted with at least one of $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino $(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$ alkyl, COOH, —C(O)Ph, C(O)O—$(C_1-C_4)$alkyl, C(O) H, —C(O)$NH_2$ or $NO_2$;

B is an imidazole optionally substituted with at least one of $(C_1-C_4)$alkyl, halo$(C_1-C_4)$alkyl, O—$(C_1-C_4)$alkyl, O-halo$(C_1-C_4)$alkyl, F, Cl, Br, I, CN, —$CH_2$CN, hydroxyl, or $NO_2$;

$R_1$, $R_2$ and $R_3$ are independently at least one of hydrogen, $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond;

Y is —C═O; and m is 1-3, or a pharmaceutically acceptable salt, hydrate, polymorph, or isomer thereof.

2. The method according to claim 1, wherein A is indolyl, optionally substituted with at least one of $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond;

Y is —C═O; and m is 1-3, or a pharmaceutically acceptable salt, hydrate, polymorph, or isomer thereof.

3. The method according to claim 1, wherein A is phenyl, optionally substituted with at least one of $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

X is a bond;

Y is —C═O; and m is 1-3, or a pharmaceutically acceptable salt, hydrate, polymorph, or isomer thereof.

4. The method according to claim 1, wherein A is indolyl, optionally substituted with at least one of $(C_1-C_4)$alkyl, halo$(C_1-C_4)$alkyl, O—$(C_1-C_4)$alkyl, O-halo$(C_1-C_4)$alkyl, $(C_1-C_4)$alkylamino, amino$(C_1-C_4)$alkyl, F, Cl, Br, I, CN, —$CH_2$CN, $NH_2$, hydroxyl, OC(O)$CF_3$, —$OCH_2$Ph, —NHCO—$(C_1-C_4)$alkyl, COOH, —C(O)Ph, C(O)O—$(C_1-C_4)$alkyl, C(O)H, —C(O)$NH_2$ or $NO_2$;

B is an imidazole, optionally substituted with at least one of $(C_1-C_4)$alkyl;

$R_1$, $R_2$ and $R_3$ are independently at least one of hydrogen, $(C_1\text{-}C_4)$alkyl, halo$(C_1\text{-}C_4)$alkyl, O—$(C_1\text{-}C_4)$alkyl, O-halo$(C_1\text{-}C_4)$alkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$;

X is a bond;

Y is —C═O; and m is 1-3, or a pharmaceutically acceptable salt, hydrate, polymorph, or isomer thereof.

5. A method of treating an Orthomyxoviridae infection in a subject in need thereof by administering to the subject a formulation having a therapeutically effective amount of a compound of the Formula VII:

(VII)

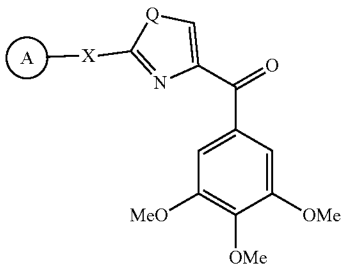

wherein

X is a bond;

Q is S or NH; and

A is a indolyl ring optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; or a pharmaceutically acceptable salt, hydrate, polymorph, or isomer thereof.

6. The method according to claim 5, wherein X is a bond; Q is NH; and A is an indolyl ring optionally substituted with at least one of $(C_1\text{-}C_4)$alkyl, halo$(C_1\text{-}C_4)$alkyl, O—$(C_1\text{-}C_4)$alkyl, O-halo$(C_1\text{-}C_4)$alkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; or a pharmaceutically acceptable salt, hydrate, polymorph, or isomer thereof.

7. A method of treating an Orthomyxoviridae infection in a subject in need thereof by administering to the subject a formulation having a therapeutically effective amount of a compound of the Formula VII(c):

VII(c)

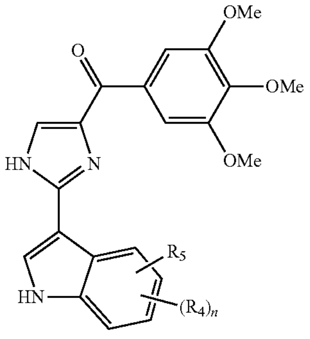

wherein $R_4$ and $R_5$ are independently hydrogen, $(C_1\text{-}C_4)$alkyl, halo$(C_1\text{-}C_4)$alkyl, O—$(C_1\text{-}C_4)$alkyl, O-halo$(C_1\text{-}C_4)$alkyl, $(C_1\text{-}C_4)$alkylamino, amino$(C_1\text{-}C_4)$alkyl, F, Cl, Br, I, CN, —$CH_2CN$, $NH_2$, hydroxyl, $OC(O)CF_3$, —$OCH_2Ph$, —NHCO—$(C_1\text{-}C_4)$alkyl, COOH, —C(O)Ph, C(O)O—$(C_1\text{-}C_4)$alkyl, C(O)H, —$C(O)NH_2$ or $NO_2$; and n is 1-4; or a pharmaceutically acceptable salt, hydrate, polymorph, or isomer thereof.

8. A method of treating an Orthomyxoviridae infection in a subject in need thereof by administering to the subject a formulation having a therapeutically effective amount of a compound 17ya represented:

(17ya)

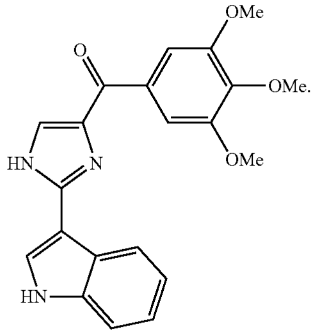

9. The method according to any one of claims 1-3, 4-5, or 6-8, wherein said Orthomyxoviridae infection is caused by an influenza virus.

10. The method according to any one of claims 1-3, 4-5, or 6-8, wherein said Orthomyxoviridae infection is caused by influenza A, influenza B, influenza C, or influenza D.

11. The method of claim 10, wherein said influenza A infection is caused by an H1N1 serotype virus.

12. The method according to claim 10, wherein the subject with an Orthomyxoviridae infection has pneumonia.

13. The method according to claim 1, further comprising a second therapy.

14. The method according to claim 13, wherein the second therapy is at least one of peramivir, zanamir, oseltamivir phosphate, baloxavir marboxil, amantadine, rimantadine, or ribavirin.

15. The method according to claim 1, wherein the compound is administered in an amount of about 1 mg to about 100 mg.

16. The method according to claim 1, wherein the compound is administered in an amount of about 4 mg to about 90 mg.

17. The method according to claim 1, wherein the compound is administered in an amount of about 4 mg to about 45 mg.

18. The method according to any one of claims 15-17 further comprising a pharmaceutically acceptable excipient.

* * * * *